(12) United States Patent
Reed et al.

(10) Patent No.: US 11,801,290 B2
(45) Date of Patent: Oct. 31, 2023

(54) **VACCINES COMPRISING *MYCOBACTERIUM LEPRAE* POLYPEPTIDES FOR THE PREVENTION, TREATMENT, AND DIAGNOSIS OF LEPROSY**

(71) Applicant: ACCESS TO ADVANCED HEALTH INSTITUTE, Seattle, WA (US)

(72) Inventors: Steven G. Reed, Seattle, WA (US); Malcolm S. Duthie, Seattle, WA (US)

(73) Assignee: ACCESS TO ADVANCED HEALTH INSTITUTE, Seattle, WA (US)

( * ) Notice: Subject to any disclaimer, the term of this patent is extended or adjusted under 35 U.S.C. 154(b) by 990 days.

(21) Appl. No.: 16/333,596

(22) PCT Filed: Sep. 15, 2017

(86) PCT No.: PCT/US2017/051824
§ 371 (c)(1),
(2) Date: Mar. 15, 2019

(87) PCT Pub. No.: WO2018/053294
PCT Pub. Date: Mar. 22, 2018

(65) Prior Publication Data
US 2020/0338180 A1    Oct. 29, 2020

Related U.S. Application Data

(60) Provisional application No. 62/396,074, filed on Sep. 16, 2016.

(51) Int. Cl.
*A61K 39/40* (2006.01)
*A61K 38/00* (2006.01)
*A61K 39/04* (2006.01)
*A61K 39/39* (2006.01)
*A61K 39/00* (2006.01)

(52) U.S. Cl.
CPC .............. *A61K 39/04* (2013.01); *A61K 39/39* (2013.01); *A61K 2039/55561* (2013.01); *A61K 2039/55566* (2013.01); *A61K 2039/55572* (2013.01); *A61K 2039/55577* (2013.01)

(58) Field of Classification Search
CPC .................................................... A61K 39/04
See application file for complete search history.

(56) References Cited

U.S. PATENT DOCUMENTS

| | | | |
|---|---|---|---|
| 4,235,877 A | 11/1980 | Fullerton | |
| 4,436,727 A | 3/1984 | Ribi | |
| 4,554,101 A | 11/1985 | Hopp | |
| 4,683,195 A | 7/1987 | Mullis et al. | |
| 4,751,180 A | 6/1988 | Cousens et al. | |
| 4,816,566 A | 3/1989 | Dechiara et al. | |
| 4,866,034 A | 9/1989 | Ribi | |
| 4,877,611 A | 10/1989 | Cantrell | |
| 4,912,094 A | 3/1990 | Myers et al. | |
| 4,935,233 A | 6/1990 | Bell et al. | |
| 5,278,302 A | 1/1994 | Caruthers et al. | |
| 5,350,681 A | 9/1994 | Iacobucci et al. | |
| 5,399,363 A | 3/1995 | Liversidge et al. | |
| 5,466,468 A | 11/1995 | Schneider et al. | |
| 5,543,158 A | 8/1996 | Gref et al. | |
| 5,641,515 A | 6/1997 | Ramtoola | |
| 5,666,153 A | 9/1997 | Copeland | |
| 5,725,871 A | 3/1998 | Illum | |
| 5,756,353 A | 5/1998 | Debs | |
| 5,780,045 A | 7/1998 | McQuinn et al. | |
| 5,804,212 A | 9/1998 | Illum | |
| 5,856,462 A | 1/1999 | Agrawal | |
| 6,113,918 A | 9/2000 | Johnson et al. | |
| 6,355,257 B1 | 3/2002 | Johnson et al. | |
| 6,544,518 B1 | 4/2003 | Friede et al. | |
| 6,583,266 B1 * | 6/2003 | Smith ................. C07K 14/35 530/350 |
| 7,189,522 B2 | 3/2007 | Esfandiari | |
| 7,538,206 B2 * | 5/2009 | Cole ................... C07K 14/345 424/234.1 |
| 2004/0197896 A1 * | 10/2004 | Cole ...................... A61P 31/08 435/252.3 |
| 2008/0131466 A1 | 6/2008 | Reed et al. | |
| 2011/0027348 A1 | 2/2011 | Feher | |
| 2011/0027349 A1 | 2/2011 | Sable et al. | |

FOREIGN PATENT DOCUMENTS

| | | |
|---|---|---|
| EP | 468520 A2 | 1/1992 |
| WO | 1994000153 A1 | 1/1994 |
| WO | 1995017210 A1 | 6/1995 |
| WO | 1995026204 A1 | 10/1995 |
| WO | 1996002555 A1 | 2/1996 |
| WO | 1996033739 A1 | 10/1996 |
| WO | 1998016247 A1 | 4/1998 |

(Continued)

OTHER PUBLICATIONS

US 6,008,200 A, 12/1999, Krieg (withdrawn)
Desbien et al., Eur. J. Immunol., 2015; 45:407-417 (Year: 2015).*
BR112019004913-4—Office Action, dated Oct. 19, 2021, 14 pages. (with English translation).
Monot, Marc, et al., "Comparative genomic and phylogeographic analysis *Mycobacterium leprae*", Nature Genetics, 2010, 11 pages.
Sampaio et al., "Immunologically reactive *M. leprae* antigens with relevance to diagnosis and vaccine development", BMC Infectious Diseases, vol. 11, No. 26, Jan. 26, 2011, pp. 1-11.
Merle et al., "BCG vaccination and leprosy protection: review of current evidence and status of BCG in leprosy control", Expert Rev Vaccines, vol. 9, Issue 2, 2010, pp. 209-222.

(Continued)

*Primary Examiner* — Brian Gangle
*Assistant Examiner* — Lakia J Jackson-Tongue
(74) *Attorney, Agent, or Firm* — Benjamin Keim; Newport IP, LLC

(57) ABSTRACT

Compositions and methods for preventing, treating and detecting leprosy are disclosed. The compositions generally comprise polypeptides comprising one or more *Mycobacterium leprae* antigens as well as polynucleotides encoding such polypeptides.

24 Claims, 11 Drawing Sheets

Specification includes a Sequence Listing.

(56) References Cited

FOREIGN PATENT DOCUMENTS

| WO | 1999033488 A2 | 7/1999 |
| --- | --- | --- |
| WO | 1999052549 A1 | 10/1999 |
| WO | 2000009159 A1 | 2/2000 |
| WO | 2011013097 A2 | 2/2011 |
| WO | 2014009438 A2 | 1/2014 |
| WO | 2018053294 A1 | 3/2018 |

OTHER PUBLICATIONS

Smith et al., "Comparison of biosequences", Advances in Applied Mathematics, vol. 2, Issue 4, Dec. 1981, pp. 482-489.

Ridley et al., "Classification of leprosy according to immunity. A five-group system", International journal of leprosy and other mycobacterial diseases, vol. 34, Issue 3, Jul.-Sep. 1966, pp. 255-273.

Goulart et al., "Risk and Protective Factors for Leprosy Development Determined by Epidemiological Surveillance of Household Contacts", Clinical and Vaccine Immunology, vol. 15, No. 1, Jan. 2008, pp. 101-105.

Chen et al., "T-Cells for Tumor Therapy Can Be Obtained from Antigen-loaded Sponge Implants" Cancer Research, vol. 54, Feb. 15, 1994, pp. 1065-1070.

Schirmbeck et al., "Antigenic Epitopes Fused to Cationic Peptide Bound to Oligonucleotides Facilitate Toll-Like Receptor 9-Dependent, but CD4+ T Cell Help-Independent, Priming of CD8+ T Cells", J. Immunol., vol. 171, Issue 10, Nov. 15, 2003, pp. 5198-5207.

Horsmans et al., "Isatoribine, an agonist of TLR7, reduces plasma virus concentration in chronic hepatitis C infection", vol. 42, Issue3, Sep. 2005, pp. 724-731.

Lee et al., "Activation of anti-hepatitis C virus responses via Toll-like receptor 7", Proc. Nat. Acad. Sci. USA, vol. 103, No. 6, Feb. 7, 2006, pp. 1828-1833.

Feuillet et al., "Involvement of Toll-like receptor 5 in the recognition of flagellated bacteria", Proc. Nat. Acad Sci. USA, vol. 103, No. 33, Aug. 15, 2006, pp. 12487-12492.

Gorden et al., "Synthetic TLR Agonists Reveal Functional Differences between Human TLR7 and TLR8", J. Immunol., vol. 174, 2005, pp. 1259-1268.

Nakao et al., "Surface-Expressed TLR6 Participates in the Recognition of Diacylated Lipopeptide and Peptidoglycan in Human Cells", J. Immunol., vol. 174, Issue 3, Feb. 1, 2005, pp. 1566-1573.

Soboll et al., "Expression of Toll-Like Receptors (TLR) and Responsiveness to TLR Agonists by Polarized Mouse Uterine Epithelial Cells in Culture", Biol. Reprod. 75, Jul. 1, 2006, pp. 131-139.

Chen et al., "Distinct Responses of Lung and Spleen Dendritic Cells to the TLR9 Agonist CpG Oligodeoxynucleotide", J. Immunol., vol. 177, Issue 4, Aug. 15, 2006, pp. 2373-2383.

Dayhoff et al., "A Model of Evolutionary Change in Proteins", Atlas of Protein Sequence and Structure, 1978, pp. 345-358.

Van Hoeven et al., "A Formulated TLR7/8 Agonist is a Flexible, Highly Potent and Effective Adjuvant for Pandemic Influenza Vaccines", Nature Scientific Reports 7, Article No. 46426, Apr. 21, 2017, pp. 1-15.

Fox et al., "Technology transfer of oil-in-water emulsion adjuvant manufacturing for pandemic influenza vaccine production in Romania", Vaccine, vol. 31, Issue 12, Oct. 13, 2012, pp. 1633-1640.

Myers et al., "Optimal alignments in linear space", CABIOS, vol. 4, No. 1, 1988, pp. 11-17.

Altschul et al., "Gapped BLAST and PSI-BLAST: a new generation of protein databases search programs" Nucleic Acids Research, vol. 25, No. 17, Jul. 16, 1997, pp. 3389-3402.

Altschul et al., "Basic Local Alignment Search Tool", J. Mol. Biol., vol. 215, Feb. 26, 1990, pp. 403-410.

Henikoff et al., "Amino acid substitution matrices from protein blocks", Proc. Natl. Acad. Sci. USA, vol. 89, Nov. 1992, pp. 10915-10919.

Deng et al., "CpG Oligodeoxynucleotides Stimulate Protective Innate Immunity against Pulmonary Klebsiella Infection", J. Immunol., vol. 173, Issue 8, Oct. 15, 2004, pp. 5148-5155.

Vollmer et al., "Immunopharmacology of CpG Oligodeoxynucleotides and Ribavirin", Antimicrob. Agents Chemother., vol. 48, Issue 6, Jun. 2004, pp. 2314-2317.

Heeke et al., "Expression of Human Asparagine Synthetase in *Escherichia coli*" The Journal of Biological Chemistry, vol. 264, No. 10, Aug. 1, 1988, pp. 5503-5509.

Cooper et al., "CPG 7909 adjuvant improves hepatitis B virus vaccine seroprotection in antiretroviral-treated HIV-infected adults", AIDS, vol. 19, Issue 14, Jun. 13, 2005, pp. 1473-1479.

Coruzzi et al., "Tissue-specific and light-regulated expression of a pea nuclear gene encoding the small subunit of ribulose-1,5-bisphosphate carboxylase" The EMBO Journal, vol. 3, No. 8, 1984, pp. 1671-1679.

Tsan et al., "Cytokine function of heat shock proteins", Am. J. Physiol. Cell Phsiol., vol. 286, Issue 4, Apr. 1, 2004, pp. C739-C744.

Tsan et al., "Endogenous ligands of Toll—like receptors", J. Leuk. Biol., vol. 76, Issue 3, Sep. 2004, pp. 514-519.

Datta et al., "A Subset of Toll-Like Receptor Ligands Induces Cross-presentation by Bone Marrow-Derived Dendritic Cells", J. Immunol., Apr. 15, 2003, vol. 170, Issue 8, pp. 4102-4110.

Engelhard et al., "The insect tracheal system: A conduit for the systemic spread of Autographa californica M nuclear polyhedrosis virus", Proc. Nati. Acad. Sci. USA, vol. 91, Apr. 1994, pp. 3224-3227.

Maddox et al., "Elevated serum levels in human pregnancy of a molecule immunochemically similar to eosinophil granule major basic protein", J. Exp. Med, vol. 158, Oct. 1983, pp. 1211-1226.

Armant et al., "Toll-like receptors: a family of pattern-recognition receptors in mammals", Genome Biology, vol. 3, No. 8, Jul. 29, 2002, pp. 3011.1-3011.6.

Lien et al. "Adjuvants and their signaling pathways: beyond TLRs", Nat. Immunol., vol. 4, No. 12, Dec. 1, 2003, pp. 1162-1164.

Murphy et al., "Genetic construction, expression, and melanoma-selective cytotoxicity of a diphtheria toxin-related a-melanocyte-stimulating hormone fusion protein", Proc. Natl. Acad. Sci. USA, vol. 83, Nov. 1986, pp. 8258-8262.

Takamatsu et al., "Expression of bacterial chloramphenicol acetyltransferase gene in tobacco plants mediated by TMV-RNA", The EMBO Journal, vol. 6, No. 2, 1987, pp. 307-311.

International search report & Written opinion dated Mar. 22, 2018 for Application No. PCT/US2017/051824, pp. 11.

Misquith et al., "In vitro evaluation of TLR4 agonist activity: Formulation effects", Colloids and Surfaces B: Biointerfaces vol. 113, Jan. 1, 2014, pp. 312-319.

Logan et al., "Adenovirus tripartite leader sequence enhances translation of mRNAs late after infection", Proc. Natl. Acad. Sci. USA, vol. 81, Jun. 1984, pp. 3655-3659.

Wigler et al., "Transformation of mammalian cells with an amplifiable dominant-acting gene", Proc. Natl. Acad. Sci. USA, vol. 77, No. 6, Jun. 1980, pp. 3567-3570.

Hartman et al., "Two dominant-acting selectable markers for gene transfer studies in mammalian cells", Proc. Nati. Acad. Sci. USA, vol. 85, Nov. 1988, pp. 8047-8051.

Scollard D M, "Classification of leprosy: a full color spectrum, or black and white?", International Journal of Leprosy and Other Mycobacterial Diseases, vol. 72, Issue 2, Jun. 1, 2004, pp. 166-168.

Takeda et al., "Toll-like receptors in innate immunity", International Immunology, vol. 17, No. 1, 2005, pp. 1-14.

India Intellectual Property Office First Examination Report No. 201917009596, dated Jan. 11, 2023, 6 pages.

Philippines Intelectual Property Office Substantive Examination Report dated Dec. 2, 2022, 6 pages.

First Substantive Official Action, Mexican Patent Application M/a/2019/003035, dated Jan. 13, 2023, 3 pages (English translation).

\* cited by examiner

SEQUENCE LISTING

<160> NUMBER OF SEQ ID NOS: 12

<210> SEQ ID NO 1
<211> LENGTH: 981
<212> TYPE: DNA
<213> ORGANISM: Mycobacterium leprae

<400> SEQUENCE: 1

```
atgattgacg tgagcgggaa gatccgagcc tgggggcgct ggcttttggt gggtgcagct      60
gcgactctgc cgagcctaat cagccttgct ggcggagcgg cgaccgcaag cgcgttctca     120
cgaccaggcc tacccgtcga gtacctacag gtgccgtcga aggcgatggg cgcagcatc     180 aaggtgcagt ttcaaaacgg cggaaacggc tctccggcgg tgtatctgct ggatggtttg     240
cgtgcgcagg acgactataa cggctgggac atcaacacct ccgcattcga gtggtactat     300
cagtcgggac tctcggtcgt gatgccggtc ggtgggcaat ccagcttcta cagcgactgg     360
tacagcccag cgtgcggcaa ggcaggttgc acgacctaca gtgggaaac attccttact     420 agcgagctgc taaatggct atccgccaat aggagtgtca atccaccgg cagcgccgtg     480 gtcggcctct cgatggccgg ttcctcggcc ctaatactgg cagcttatca ccccgatcag     540
```

```
ttcatctatg ctggctcgtt gtcggcgctg atggactcct cccagggat agaaccccag    600 ctaatcggct tggcgatggg tgatgctggt ggctacaagg ccgcggacat gtggggacca    660
ccaaatgacc cggcctggca cgaaacgac cccattctgc aggctgggaa gctggtcgcc    720
aacaacaccc acctatgggt ttactgtggt aacggcacac cgtcagagtt gggtggaacc    780
aacgtacccg cggaattcct ggagaacttc gtgcacggca gcaacctaaa gttccaggac    840
gcctacaacg tgctggtgg ccacaacgct gtgttcaacc tcaatgccga cggaacgcac    900
agctgggagt actggggagc ccagctcaac gccatgaagc ccgacctaca gaacaccttg    960
atggctgtac cccgcagcgg t                                             981
```

<210> SEQ ID NO 2
<211> LENGTH: 327
<212> TYPE: PRT
<213> ORGANISM: Mycobacterium leprae

<400> SEQUENCE: 2

Met Ile Asp Val Ser Gly Lys Ile Arg Ala Trp Gly Arg Trp Leu Leu
1               5                   10                  15

Val Gly Ala Ala Ala Thr Leu Pro Ser Leu Ile Ser Leu Ala Gly Gly
            20                  25                  30

Ala Ala Thr Ala Ser Ala Phe Ser Arg Pro Gly Leu Pro Val Glu Tyr
        35                  40                  45

Leu Gln Val Pro Ser Glu Ala Met Gly Arg Ser Ile Lys Val Gln Phe
    50                  55                  60

Gln Asn Gly Gly Asn Gly Ser Pro Ala Val Tyr Leu Leu Asp Gly Leu
65                  70                  75                  80

Arg Ala Gln Asp Asp Tyr Asn Gly Trp Asp Ile Asn Thr Ser Ala Phe
                85                  90                  95

Glu Trp Tyr Tyr Gln Ser Gly Leu Ser Val Val Met Pro Val Gly Gly
            100                 105                 110

Gln Ser Ser Phe Tyr Ser Asp Trp Tyr Ser Pro Ala Cys Gly Lys Ala
        115                 120                 125

Gly Cys Thr Thr Tyr Lys Trp Glu Thr Phe Leu Thr Ser Glu Leu Pro
    130                 135                 140

Lys Trp Leu Ser Ala Asn Arg Ser Val Lys Ser Thr Gly Ser Ala Val
145                 150                 155                 160

Val Gly Leu Ser Met Ala Gly Ser Ser Ala Leu Ile Leu Ala Ala Tyr
                165                 170                 175

His Pro Asp Gln Phe Ile Tyr Ala Gly Ser Leu Ser Ala Leu Met Asp
            180                 185                 190

Ser Ser Gln Gly Ile Glu Pro Gln Leu Ile Gly Leu Ala Met Gly Asp
        195                 200                 205

Ala Gly Gly Tyr Lys Ala Ala Asp Met Trp Gly Pro Pro Asn Asp Pro
    210                 215                 220

Ala Trp Gln Arg Asn Asp Pro Ile Leu Gln Ala Gly Lys Leu Val Ala
225                 230                 235                 240

Asn Asn Thr His Leu Trp Val Tyr Cys Gly Asn Gly Thr Pro Ser Glu
                245                 250                 255

Leu Gly Gly Thr Asn Val Pro Ala Glu Phe Leu Glu Asn Phe Val His
            260                 265                 270

Gly Ser Asn Leu Lys Phe Gln Asp Ala Tyr Asn Gly Ala Gly Gly His
        275                 280                 285

Asn Ala Val Phe Asn Leu Asn Ala Asp Gly Thr His Ser Trp Glu Tyr

```
                290             295             300
Trp Gly Ala Gln Leu Asn Ala Met Lys Pro Asp Leu Gln Asn Thr Leu
305                 310                 315                 320

Met Ala Val Pro Arg Ser Gly
                325
```

<210> SEQ ID NO 3
<211> LENGTH: 867
<212> TYPE: DNA
<213> ORGANISM: Mycobacterium leprae

<400> SEQUENCE: 3

```
ttctcacgac caggcctacc cgtcgagtac ctacaggtgc cgtcggaggc gatgggcgc     60
agcatcaagg tgcagtttca aaacggcgga aacggctctc cggcggtgta tctgctggat   120
ggtttgcgtg cgcaggacga ctataacggc tgggacatca cacctccgc attcgagtgg    180
tactatcagt cgggactctc ggtcgtgatg ccggtcggtg gcaatccag cttctacagc    240
gactggtaca gcccagcgtg cggcaaggca ggttgcacga cctacaagtg gaaacattc    300
cttactagcg agctgcctaa atggctatcc gccaatagga gtgtcaaatc caccggcagc   360
gccgtggtcg gcctctcgat ggccggttcc tcggccctaa tactggcagc ttatcacccc   420
gatcagttca tctatgctgg ctcgttgtcg gcgctgatgg actcctccca ggggatagaa   480
ccccagctaa tcggcttggc gatgggtgat gctggtggct acaaggccgc ggacatgtgg   540
ggaccaccaa tgacccggc ctggcaacga acgaccccca ttctgcaggc tgggaagctg    600
gtcgccaaca cacccacct atgggtttac tgtggtaacg gcacaccgtc agagttgggt    660
ggaaccaacg tacccgcgga attcctggag aacttcgtgc acggcagcaa cctaaagttc   720
caggacgcct acaacggtgc tggtggccac aacgctgtgt caacctcaa tgccgacgga   780
acgcacagct gggagtactg gggagcccag ctcaacgcca tgaagcccga cctacagaac   840
accttgatgg ctgtacccg cagcggt                                        867
```

<210> SEQ ID NO 4
<211> LENGTH: 289
<212> TYPE: PRT
<213> ORGANISM: Mycobacterium leprae

<400> SEQUENCE: 4

```
Phe Ser Arg Pro Gly Leu Pro Val Glu Tyr Leu Gln Val Pro Ser Glu
1               5                   10                  15

Ala Met Gly Arg Ser Ile Lys Val Gln Phe Gln Asn Gly Gly Asn Gly
                20                  25                  30

Ser Pro Ala Val Tyr Leu Leu Asp Gly Leu Arg Ala Gln Asp Asp Tyr
            35                  40                  45

Asn Gly Trp Asp Ile Asn Thr Ser Ala Phe Glu Trp Tyr Tyr Gln Ser
    50                  55                  60

Gly Leu Ser Val Val Met Pro Val Gly Gly Gln Ser Ser Phe Tyr Ser
65                  70                  75                  80

Asp Trp Tyr Ser Pro Ala Cys Gly Lys Ala Gly Cys Thr Thr Tyr Lys
                85                  90                  95

Trp Glu Thr Phe Leu Thr Ser Glu Leu Pro Lys Trp Leu Ser Ala Asn
                100                 105                 110

Arg Ser Val Lys Ser Thr Gly Ser Ala Val Val Gly Leu Ser Met Ala
            115                 120                 125

Gly Ser Ser Ala Leu Ile Leu Ala Ala Tyr His Pro Asp Gln Phe Ile
```

```
                130           135              140
Tyr Ala Gly Ser Leu Ser Ala Leu Met Asp Ser Ser Gln Gly Ile Glu
145                 150                 155                 160

Pro Gln Leu Ile Gly Leu Ala Met Gly Asp Ala Gly Gly Tyr Lys Ala
                165                 170                 175

Ala Asp Met Trp Gly Pro Pro Asn Asp Pro Ala Trp Gln Arg Asn Asp
            180                 185                 190

Pro Ile Leu Gln Ala Gly Lys Leu Val Ala Asn Asn Thr His Leu Trp
        195                 200                 205

Val Tyr Cys Gly Asn Gly Thr Pro Ser Glu Leu Gly Gly Thr Asn Val
    210                 215                 220

Pro Ala Glu Phe Leu Glu Asn Phe Val His Gly Ser Asn Leu Lys Phe
225                 230                 235                 240

Gln Asp Ala Tyr Asn Gly Ala Gly Gly His Asn Ala Val Phe Asn Leu
                245                 250                 255

Asn Ala Asp Gly Thr His Ser Trp Glu Tyr Trp Gly Ala Gln Leu Asn
            260                 265                 270

Ala Met Lys Pro Asp Leu Gln Asn Thr Leu Met Ala Val Pro Arg Ser
        275                 280                 285

Gly

<210> SEQ ID NO 5
<211> LENGTH: 861
<212> TYPE: DNA
<213> ORGANISM: Mycobacterium leprae

<400> SEQUENCE: 5
atgaatcagg ttgacctgga ctcgacacat cgcaaaggat tgtgggcgat actggcgatt    60
gccgtggtgg ccagcgccag tgcctttacg atgccgttgc ctgcggccgc caacgccgat   120
cccgcgcccc tgccgccatc gacggctacg gcagctccct cacctgcgca ggagatcatt   180 acacccttc caggcgcccc tgtctcgtcc gaagcccaac cgggtgatcc caatgcgccg    240
tcgctcgatc cgaatgcacc atacccactt gcagtcgatc ccaacgccgg ccgaatcacc   300
aacgctgtcg gtggatttag cttcgtcctt cctgccggtt gggtggagtc agaggcttca   360
catcttgact acggttcggt gctgctcagc aaagccatcg agcagccgcc cgtgcttggt   420
cagccgacgg tggtcgctac cgacacccgt atagtgctcg gccggctgga ccaaaagctc   480
tacgccagtg ccgaagccga acattaag gccgcggtcc gactgggctc ggatatgggt    540
gagttctacc tgccataccc cggtacgcgg atcaaccaag aaaccattcc gctccacgcc   600
aacgggatag ctggaagcgc ctcctactac gaggtcaaat tcagcgatcc aataagcca    660 attggccaaa tatgtacgag cgtagtcggc tcgccagcgg cgagtacccc tgacgtgggg   720
ccctcgcagc gttggtttgt ggtatggctc ggaacctcga ataacccggt ggacaagggc   780
gcagccaaag agctggctga gtctataccg tcagagatgg ctccgatccc ggcgtcggtt   840
tccgctccgg cacctgttgg a                                             861

<210> SEQ ID NO 6
<211> LENGTH: 287
<212> TYPE: PRT
<213> ORGANISM: Mycobacterium leprae

<400> SEQUENCE: 6

Met Asn Gln Val Asp Leu Asp Ser Thr His Arg Lys Gly Leu Trp Ala
1               5                   10                  15
```

```
Ile Leu Ala Ile Ala Val Val Ala Ser Ala Ser Ala Phe Thr Met Pro
            20                  25                  30

Leu Pro Ala Ala Ala Asn Ala Asp Pro Ala Pro Leu Pro Pro Ser Thr
        35                  40                  45

Ala Thr Ala Ala Pro Ser Pro Ala Gln Glu Ile Ile Thr Pro Leu Pro
    50                  55                  60

Gly Ala Pro Val Ser Ser Glu Ala Gln Pro Gly Asp Pro Asn Ala Pro
65                  70                  75                  80

Ser Leu Asp Pro Asn Ala Pro Tyr Pro Leu Ala Val Asp Pro Asn Ala
                85                  90                  95

Gly Arg Ile Thr Asn Ala Val Gly Gly Phe Ser Phe Val Leu Pro Ala
            100                 105                 110

Gly Trp Val Glu Ser Glu Ala Ser His Leu Asp Tyr Gly Ser Val Leu
        115                 120                 125

Leu Ser Lys Ala Ile Glu Gln Pro Pro Val Leu Gly Gln Pro Thr Val
    130                 135                 140

Val Ala Thr Asp Thr Arg Ile Val Leu Gly Arg Leu Asp Gln Lys Leu
145                 150                 155                 160

Tyr Ala Ser Ala Glu Ala Asp Asn Ile Lys Ala Ala Val Arg Leu Gly
                165                 170                 175

Ser Asp Met Gly Glu Phe Tyr Leu Pro Tyr Pro Gly Thr Arg Ile Asn
            180                 185                 190

Gln Glu Thr Ile Pro Leu His Ala Asn Gly Ile Ala Gly Ser Ala Ser
        195                 200                 205

Tyr Tyr Glu Val Lys Phe Ser Asp Pro Asn Lys Pro Ile Gly Gln Ile
    210                 215                 220

Cys Thr Ser Val Val Gly Ser Pro Ala Ala Ser Thr Pro Asp Val Gly
225                 230                 235                 240

Pro Ser Gln Arg Trp Phe Val Val Trp Leu Gly Thr Ser Asn Asn Pro
                245                 250                 255

Val Asp Lys Gly Ala Ala Lys Glu Leu Ala Glu Ser Ile Arg Ser Glu
            260                 265                 270

Met Ala Pro Ile Pro Ala Ser Val Ser Ala Pro Ala Pro Val Gly
        275                 280                 285
```

<210> SEQ ID NO 7
<211> LENGTH: 459
<212> TYPE: DNA
<213> ORGANISM: Mycobacterium leprae

<400> SEQUENCE: 7

```
atgtctcggc tgagcaccag cctatgtaaa ggtgctgttt ttctcgtttt cggtatcatt     60
cctgtggcat ttccgacgac cgccgttgcc gatggttcca cggaggattt tccgatcccc    120
cgcaggcaaa tcgccaccac ctgtgatgca gagcagtatt tggcggccgt cagggatacc    180
agcccgatct actaccagcg gtacatgatc gatatgcaca acaagccgac tgacatccag    240
caggccgcgg tcaatcgtat ccattggttc tattccttga gccccaccga ccgtaggcag    300
tattccgagg acaccgctac aaacgtctac tacgagcaga tggccacgca ttggggaaac    360
tgggcgaaga ttttcttcaa taacaagggc gttgtcgcca aagccaccga ggtttgcaac    420
cagtaccagg ccggagacat gtcggtgtgg aactggccg                           459
```

<210> SEQ ID NO 8
<211> LENGTH: 153

```
<212> TYPE: PRT
<213> ORGANISM: Mycobacterium leprae

<400> SEQUENCE: 8

Met Ser Arg Leu Ser Thr Ser Leu Cys Lys Gly Ala Val Phe Leu Val
1               5                   10                  15

Phe Gly Ile Ile Pro Val Ala Phe Pro Thr Thr Ala Val Ala Asp Gly
                20                  25                  30

Ser Thr Glu Asp Phe Pro Ile Pro Arg Arg Gln Ile Ala Thr Thr Cys
            35                  40                  45

Asp Ala Glu Gln Tyr Leu Ala Ala Val Arg Asp Thr Ser Pro Ile Tyr
        50                  55                  60

Tyr Gln Arg Tyr Met Ile Asp Met His Asn Lys Pro Thr Asp Ile Gln
65                  70                  75                  80

Gln Ala Ala Val Asn Arg Ile His Trp Phe Tyr Ser Leu Ser Pro Thr
                    85                  90                  95

Asp Arg Arg Gln Tyr Ser Glu Asp Thr Ala Thr Asn Val Tyr Tyr Glu
                100                 105                 110

Gln Met Ala Thr His Trp Gly Asn Trp Ala Lys Ile Phe Phe Asn Asn
            115                 120                 125

Lys Gly Val Val Ala Lys Ala Thr Glu Val Cys Asn Gln Tyr Gln Ala
        130                 135                 140

Gly Asp Met Ser Val Trp Asn Trp Pro
145                 150

<210> SEQ ID NO 9
<211> LENGTH: 288
<212> TYPE: DNA
<213> ORGANISM: Mycobacterium leprae

<400> SEQUENCE: 9
atgacacaga ttatgtacaa ctacccggca atgttggacc acgccgggaa tatgtcagcc      60
tgcgccggcg ctttgcaggg ggtgggcatc gacatcgctg ccgagcaagc tgcgttgcaa     120
gcttgctggg gggcgatac  tgggattagt tatcaggcct ggcaggtgca gtggaaccag     180
gccacggaag agatggtgcg tgcctaccat gcaatggcca cactcaccag aaacaacact     240
ttggctatgc tcacccgcga ccaagctgaa gccgccaaat ggggcggc                  288

<210> SEQ ID NO 10
<211> LENGTH: 96
<212> TYPE: PRT
<213> ORGANISM: Mycobacterium leprae

<400> SEQUENCE: 10

Met Thr Gln Ile Met Tyr Asn Tyr Pro Ala Met Leu Asp His Ala Gly
1               5                   10                  15

Asn Met Ser Ala Cys Ala Gly Ala Leu Gln Gly Val Gly Ile Asp Ile
                20                  25                  30

Ala Ala Glu Gln Ala Ala Leu Gln Ala Cys Trp Gly Gly Asp Thr Gly
            35                  40                  45

Ile Ser Tyr Gln Ala Trp Gln Val Gln Trp Asn Gln Ala Thr Glu Glu
        50                  55                  60

Met Val Arg Ala Tyr His Ala Met Ala Asn Thr His Gln Asn Asn Thr
65                  70                  75                  80

Leu Ala Met Leu Thr Arg Asp Gln Ala Glu Ala Ala Lys Trp Gly Gly
                    85                  90                  95
```

<210> SEQ ID NO 11
<211> LENGTH: 2493
<212> TYPE: DNA
<213> ORGANISM: Artificial Sequence
<220> FEATURE:
<223> OTHER INFORMATION: Synthetic Construct

<400> SEQUENCE: 11

| | | | | | |
|---|---|---|---|---|---|
| atgacacaga | ttatgtacaa | ctacccggca | atgttggacc | acgccgggaa | tatgtcagcc | 60 |
| tgcgccggcg | ctttgcaggg | ggtgggcatc | gacatcgctg | ccgagcaagc | tgcgttgcaa | 120 |
| gcttgctggg | ggggcgatac | tgggattagt | tatcaggcct | ggcaggtgca | gtggaaccag | 180 |
| gccacggaag | agatggtgcg | tgcctaccat | gcaatggcca | acactcacca | aaacaacact | 240 |
| ttggctatgc | tcacccgcga | ccaagctgaa | gccgccaaat | ggggcggcgg | atccatgtct | 300 |
| cggctgagca | ccagcctatg | taaaggtgct | gttttctcg | ttttcggtat | cattcctgtg | 360 |
| gcatttccga | cgaccgccgt | tgccgatggt | tccacggagg | attttccgat | ccccgcagg | 420 |
| caaatcgcca | ccacctgtga | tgcagagcag | tatttggcgg | ccgtcaggga | taccagcccg | 480 |
| atctactacc | agcggtacat | gatcgatatg | cacaacaagc | cgactgacat | ccagcaggcc | 540 |
| gcggtcaatc | gtatccattg | gttctattcc | ttgagcccca | ccgaccgtag | gcagtattcc | 600 |
| gaggacaccg | ctacaaacgt | ctactacgag | cagatggcca | cgcattgggg | aaactgggcg | 660 |
| aagattttct | tcaataacaa | gggcgttgtc | gccaaagcca | ccgaggtttg | caaccagtac | 720 |
| caggccggag | acatgtcggt | gtggaactgg | ccggagctca | tgaatcaggt | tgacctggac | 780 |
| tcgacacatc | gcaaaggatt | gtgggcgata | ctggcgattg | ccgtggtggc | cagcgccagt | 840 |
| gcctttacga | tgccgttgcc | tgcggccgcc | aacgccgatc | ccgcgcccct | gccgccatcg | 900 |
| acggctacgg | cagctccctc | acctgcgcag | gagatcatta | cacccttcc | aggcgcccct | 960 |
| gtctcgtccg | aagcccaacc | gggtgatccc | aatgcgccgt | cgctcgatcc | gaatgcacca | 1020 |
| tacccacttg | cagtcgatcc | caacgccggc | cgaatcacca | acgctgtcgg | tggatttagc | 1080 |
| ttcgtccttc | ctgccggttg | ggtggagtca | gaggcttcac | atcttgacta | cggttcggtg | 1140 |
| ctgctcagca | aagccatcga | gcagccgccc | gtgcttggtc | agccgacggt | ggtcgctacc | 1200 |
| gacacccgta | tagtgctcgg | ccggctggac | caaaagctct | acgccagtgc | cgaagccgac | 1260 |
| aacattaagg | ccgcggtccg | actgggctcg | gatatgggtg | agttctacct | gccataccc | 1320 |
| ggtacgcgga | tcaaccaaga | aaccattccg | ctccacgcca | acgggatagc | tggaagcgcc | 1380 |
| tcctactacg | aggtcaaatt | cagcgatccc | aataagccaa | ttggccaaat | atgtacgagc | 1440 |
| gtagtcggct | cgccagcggc | gagtacccct | gacgtggggc | cctcgcagcg | ttggtttgtg | 1500 |
| gtatggctcg | gaacctcgaa | taacccggtg | gacaagggcg | cagccaaaga | gctggctgag | 1560 |
| tctatccggt | cagagatggc | tccgatcccg | gcgtcggttt | ccgctccggc | acctgttgga | 1620 |
| gtcgacttct | cacgaccagg | cctacccgtc | gagtacctac | aggtgccgtc | ggaggcgatg | 1680 |
| gggcgcagca | tcaaggtgca | gtttcaaaac | ggcggaaacg | gctctccggc | ggtgtatctg | 1740 |
| ctggatggtt | tgcgtgcgca | ggacgactat | aacggctggg | acatcaacac | ctccgcattc | 1800 |
| gagtggtact | atcagtcggg | actctcggtc | gtgatgccgg | tcgtgggca | atccagcttc | 1860 |
| tacagcgact | ggtacagccc | agcgtgcggc | aaggcaggtt | gcacgaccta | caagtgggaa | 1920 |
| acattcctta | ctagcgagct | gcctaaatgg | ctatccgcca | ataggagtgt | caaatccacc | 1980 |
| ggcagcgccg | tggtcggcct | ctcgatggcc | ggttcctcgg | ccctaatact | ggcagcttat | 2040 |
| caccccgatc | agttcatcta | tgctggctcg | ttgtcggcgc | tgatggactc | ctcccagggg | 2100 |

```
atagaacccc agctaatcgg cttggcgatg ggtgatgctg gtggctacaa ggccgcggac    2160
atgtggggac caccaaatga cccggcctgg caacgaaacg accccattct gcaggctggg    2220
aagctggtcg ccaacaacac ccacctatgg gtttactgtg gtaacggcac accgtcagag    2280
ttgggtggaa ccaacgtacc cgcggaattc ctggagaact tcgtgcacgg cagcaaccta    2340
aagttccagg acgcctacaa cggtgctggt ggccacaacg ctgtgttcaa cctcaatgcc    2400
gacggaacgc acagctggga gtactgggga gcccagctca acgccatgaa gcccgaccta    2460
cagaacacct tgatggctgt accccgcagc ggt                                 2493
```

<210> SEQ ID NO 12
<211> LENGTH: 831
<212> TYPE: PRT
<213> ORGANISM: Artificial Sequence
<220> FEATURE:
<223> OTHER INFORMATION: Synthetic Construct

<400> SEQUENCE: 12

```
Met Thr Gln Ile Met Tyr Asn Tyr Pro Ala Met Leu Asp His Ala Gly
1               5                   10                  15

Asn Met Ser Ala Cys Ala Gly Ala Leu Gln Gly Val Gly Ile Asp Ile
            20                  25                  30

Ala Ala Glu Gln Ala Ala Leu Gln Ala Cys Trp Gly Gly Asp Thr Gly
        35                  40                  45

Ile Ser Tyr Gln Ala Trp Gln Val Gln Trp Asn Gln Ala Thr Glu Glu
    50                  55                  60

Met Val Arg Ala Tyr His Ala Met Ala Asn Thr His Gln Asn Asn Thr
65                  70                  75                  80

Leu Ala Met Leu Thr Arg Asp Gln Ala Glu Ala Ala Lys Trp Gly Gly
                85                  90                  95

Gly Ser Met Ser Arg Leu Ser Thr Ser Leu Cys Lys Gly Ala Val Phe
            100                 105                 110

Leu Val Phe Gly Ile Ile Pro Val Ala Phe Pro Thr Thr Ala Val Ala
        115                 120                 125

Asp Gly Ser Thr Glu Asp Phe Pro Ile Pro Arg Arg Gln Ile Ala Thr
    130                 135                 140

Thr Cys Asp Ala Glu Gln Tyr Leu Ala Ala Val Arg Asp Thr Ser Pro
145                 150                 155                 160

Ile Tyr Tyr Gln Arg Tyr Met Ile Asp Met His Asn Lys Pro Thr Asp
                165                 170                 175

Ile Gln Gln Ala Ala Val Asn Arg Ile His Trp Phe Tyr Ser Leu Ser
            180                 185                 190

Pro Thr Asp Arg Arg Gln Tyr Ser Glu Asp Thr Ala Thr Asn Val Tyr
        195                 200                 205

Tyr Glu Gln Met Ala Thr His Trp Gly Asn Trp Ala Lys Ile Phe Phe
    210                 215                 220

Asn Asn Lys Gly Val Val Ala Lys Ala Thr Glu Val Cys Asn Gln Tyr
225                 230                 235                 240

Gln Ala Gly Asp Met Ser Val Trp Asn Trp Pro Glu Leu Met Asn Gln
                245                 250                 255

Val Asp Leu Asp Ser Thr His Arg Lys Gly Leu Trp Ala Ile Leu Ala
            260                 265                 270

Ile Ala Val Val Ala Ser Ala Ser Ala Phe Thr Met Pro Leu Pro Ala
        275                 280                 285
```

-continued

```
Ala Ala Asn Ala Asp Pro Ala Pro Leu Pro Pro Ser Thr Ala Thr Ala
    290                 295                 300
Ala Pro Ser Pro Ala Gln Glu Ile Ile Thr Pro Leu Pro Gly Ala Pro
305                 310                 315                 320
Val Ser Ser Glu Ala Gln Pro Gly Asp Pro Asn Ala Pro Ser Leu Asp
                325                 330                 335
Pro Asn Ala Pro Tyr Pro Leu Ala Val Asp Pro Asn Ala Gly Arg Ile
            340                 345                 350
Thr Asn Ala Val Gly Gly Phe Ser Phe Val Leu Pro Ala Gly Trp Val
        355                 360                 365
Glu Ser Glu Ala Ser His Leu Asp Tyr Gly Ser Val Leu Leu Ser Lys
370                 375                 380
Ala Ile Glu Gln Pro Pro Val Leu Gly Gln Pro Thr Val Val Ala Thr
385                 390                 395                 400
Asp Thr Arg Ile Val Leu Gly Arg Leu Asp Gln Lys Leu Tyr Ala Ser
                405                 410                 415
Ala Glu Ala Asp Asn Ile Lys Ala Ala Val Arg Leu Gly Ser Asp Met
            420                 425                 430
Gly Glu Phe Tyr Leu Pro Tyr Pro Gly Thr Arg Ile Asn Gln Glu Thr
        435                 440                 445
Ile Pro Leu His Ala Asn Gly Ile Ala Gly Ser Ala Ser Tyr Tyr Glu
450                 455                 460
Val Lys Phe Ser Asp Pro Asn Lys Pro Ile Gly Gln Ile Cys Thr Ser
465                 470                 475                 480
Val Val Gly Ser Pro Ala Ala Ser Thr Pro Asp Val Gly Pro Ser Gln
                485                 490                 495
Arg Trp Phe Val Val Trp Leu Gly Thr Ser Asn Asn Pro Val Asp Lys
            500                 505                 510
Gly Ala Ala Lys Glu Leu Ala Glu Ser Ile Arg Ser Glu Met Ala Pro
        515                 520                 525
Ile Pro Ala Ser Val Ser Ala Pro Ala Pro Val Gly Val Asp Phe Ser
530                 535                 540
Arg Pro Gly Leu Pro Val Glu Tyr Leu Gln Val Pro Ser Glu Ala Met
545                 550                 555                 560
Gly Arg Ser Ile Lys Val Gln Phe Gln Asn Gly Gly Asn Gly Ser Pro
                565                 570                 575
Ala Val Tyr Leu Leu Asp Gly Leu Arg Ala Gln Asp Asp Tyr Asn Gly
            580                 585                 590
Trp Asp Ile Asn Thr Ser Ala Phe Glu Trp Tyr Tyr Gln Ser Gly Leu
        595                 600                 605
Ser Val Val Met Pro Val Gly Gly Gln Ser Ser Phe Tyr Ser Asp Trp
610                 615                 620
Tyr Ser Pro Ala Cys Gly Lys Ala Gly Cys Thr Thr Tyr Lys Trp Glu
625                 630                 635                 640
Thr Phe Leu Thr Ser Glu Leu Pro Lys Trp Leu Ser Ala Asn Arg Ser
                645                 650                 655
Val Lys Ser Thr Gly Ser Ala Val Val Gly Leu Ser Met Ala Gly Ser
            660                 665                 670
Ser Ala Leu Ile Leu Ala Ala Tyr His Pro Asp Gln Phe Ile Tyr Ala
        675                 680                 685
Gly Ser Leu Ser Ala Leu Met Asp Ser Ser Gln Gly Ile Glu Pro Gln
690                 695                 700
Leu Ile Gly Leu Ala Met Gly Asp Ala Gly Gly Tyr Lys Ala Ala Asp
```

-continued

```
705                 710                 715                 720

Met Trp Gly Pro Pro Asn Asp Pro Ala Trp Gln Arg Asn Asp Pro Ile
                725                 730                 735

Leu Gln Ala Gly Lys Leu Val Ala Asn Asn Thr His Leu Trp Val Tyr
            740                 745                 750

Cys Gly Asn Gly Thr Pro Ser Glu Leu Gly Gly Thr Asn Val Pro Ala
        755                 760                 765

Glu Phe Leu Glu Asn Phe Val His Gly Ser Asn Leu Lys Phe Gln Asp
    770                 775                 780

Ala Tyr Asn Gly Ala Gly Gly His Asn Ala Val Phe Asn Leu Asn Ala
785                 790                 795                 800

Asp Gly Thr His Ser Trp Glu Tyr Trp Gly Ala Gln Leu Asn Ala Met
                805                 810                 815

Lys Pro Asp Leu Gln Asn Thr Leu Met Ala Val Pro Arg Ser Gly
            820                 825                 830
```

VACCINES COMPRISING *MYCOBACTERIUM LEPRAE* POLYPEPTIDES FOR THE PREVENTION, TREATMENT, AND DIAGNOSIS OF LEPROSY

CROSS-REFERENCE TO RELATED APPLICATIONS

This application claims the benefit of U.S. Provisional Application No. 62/396,074, filed Sep. 16, 2016, which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 712192004040SEQLIST.txt, date recorded: Sep. 14, 2017, size: 25 KB).

BACKGROUND

Technical Field

The present disclosure relates generally to compositions and methods for preventing, treating and detecting leprosy in patients. More particularly, the disclosure relates to compositions and methods comprising *Mycobacterium leprae* antigens and fusion polypeptides, as well as polynucleotides encoding such antigens and fusion polypeptides.

Description of the Related Arts

Leprosy (Hansen's disease) is an infectious peripheral neurological disorder caused by *Mycobacterium leprae*. Nerve involvement in leprosy patients can present as sensory and/or motor neuron damage and can advance to cause disability and disfigurement. Nerve damage likely involves a complicated interplay of both host immunity and mycobacterial infection-mediated events (1, 2). Although bacterial cure can be achieved by multidrug therapy (MDT), which the World Health Organization (WHO) provides free of charge for registered leprosy patients, leprosy remains as a public health problem in many regions. Declines in global incidence prompted by the introduction of MDT and drive toward 'elimination' as a global health problem by the year 2000 have now levelled off. More worryingly, it is widely believed that a large number of cases go unreported {Smith, 2015 #4604}. Recent new case incidence rates indicate that transmission continues and the disease is slowly re-emerging in many regions that previously reported elimination.

The current pursuit of preventative measures against leprosy involves provision of MDT for patients or chemoprophylaxis within high risk populations. These strategies, however, are limited. Unlike drug treatment, vaccines could be used to potentially provide active and sustained protection in both uninfected and infected individuals. Multibacillary (MB) leprosy patients present with many disseminated skin lesions and large bacterial burdens, indicating that the strong humoral immune responses that they classically exhibit are not protective. Replication and dissemination of *M. leprae* is limited in paucibacillary (PB) leprosy patients, however, suggesting the potent cellular immune response they develop is associated with limited or localized disease. In addition, despite presumed exposure to *M. leprae*, the vast majority of healthy household contacts (HHC) of MB patients appear to develop effective immunity. Understanding the targets of the immune response of these individuals is likely the key to generating an effective vaccine.

By promoting a lasting adaptive immune response, a vaccine, unlike drug treatment, has the potential to provide active and sustained protection. The current standard—and only administered— vaccine against *M. leprae* is the BCG vaccine, originally developed for use in tuberculosis. The persistence of leprosy in countries where BCG is implemented suggests its effectiveness is limited. (Goulart I M, *Clin Vaccine Immunol* 2008; 15(1): 101-5.) The degree of protection afforded by BCG against leprosy has varied dramatically between studies. Systematic meta-analyses indicate that BCG has a wide-ranging protective efficacy with an average around 50% and protection appears to be better against the MB than PB forms. (Setia M S et al., *Lancet Infect Dis* 2006; 6(3): 162-70; Merle C S, *Expert review of vaccines*. 2010; 9(2): 209-22) Furthermore, BCG vaccination has been shown to precipitate paucibacillary (PB) leprosy in some instances, negating its limited usefulness.

*M. leprae* itself as an immunogen has been assessed in various trials, often to see if it can add to the protective effect of BCG. Large-scale studies in Venezuela, Malawi and India testing the use of killed *M. leprae* in combination with BCG have been largely inconclusive, with wide discrepancies in results. (Convit J et al., *Lancet* 1992; 339(8791): 446-50; Karonga Prevention Trial Group, *Lancet* 1996; 348(9019): 17-24) As a practical matter, production of a vaccine using killed *M. leprae* would be enormously constrained by the difficulties associated with mass production.

Accordingly, there remains a significant need for compositions and vaccines that can effectively prevent, treat and/or diagnose leprosy in humans and other mammals. The present disclosure fulfills these needs and offers other related advantages.

BRIEF SUMMARY

The present disclosure provides compositions, kits and methods for preventing, treating and detecting leprosy.

In one aspect the disclosure provides compositions comprising at least two *Mycobacterium leprae* (*M. leprae*) antigens selected from the group consisting of ML2028, ML2055, and ML2380, or at least two *M. leprae* antigens each having at least 90% amino acid sequence identity to ML2028, ML2055, or ML2380. In some embodiments, the composition comprises ML2028 and ML2055; or an *M. leprae* antigen having at least 90% amino acid identity to ML2028 and an *M. leprae* antigen having at least 90% amino acid identity to ML2055. In some embodiments, the composition comprises ML2028 and ML2380; or an *M. leprae* antigen having at least 90% amino acid identity to ML2028 and an *M. leprae* antigen having at least 90% amino acid identity to ML2380. In some embodiments, the composition comprises ML2055 and ML2380; or an *M. leprae* antigen having at least 90% amino acid identity to ML2055 and an *M. leprae* antigen having at least 90% amino acid identity to ML2380. In some embodiments, the composition comprises ML2028, ML2055, and ML2380; or an *M. leprae* antigen having at least 90% amino acid identity to ML2028, an *M. leprae* antigen having at least 90% amino acid identity to ML2055, and an *M. leprae* antigen having at least 90% amino acid identity to ML2380. In some embodiments, the composition further comprises ML2531 or a *M. leprae* antigen having at least 90% amino acid sequence identity to ML2531.

In another aspect the disclosure provides fusion polypeptides comprising at least two *Mycobacterium leprae* (*M. leprae*) antigens selected from the group consisting of ML2028, ML2055, and ML2380, or at least two *M. leprae* antigens each having at least 90% amino acid sequence identity to ML2028, ML2055, or ML2380. In some embodiments, the fusion polypeptide comprises ML2028 and ML2055; or an *M. leprae* antigen having at least 90% amino acid identity to ML2028 and an *M. leprae* antigen having at least 90% amino acid identity to ML2055. In some embodiments, the fusion polypeptide comprises ML2028 and ML2380; or an *M. leprae* antigen having at least 90% amino acid identity to ML2028 and an *M. leprae* antigen having at least 90% amino acid identity to ML2380. In some embodiments, the fusion polypeptide comprises ML2055 and ML2380; or an *M. leprae* antigen having at least 90% amino acid identity to ML2055 and an *M. leprae* antigen having at least 90% amino acid identity to ML2380. In some embodiments, the fusion polypeptide comprises ML2028, ML2055, and ML2380; or an *M. leprae* antigen having at least 90% amino acid identity to ML2028, an *M. leprae* antigen having at least 90% amino acid identity to ML2055, and an *M. leprae* antigen having at least 90% amino acid identity to ML2380. In some embodiments, the fusion polypeptide further comprises *M. leprae* antigen ML2S31. In some embodiments, the fusion polypeptide comprises the sequence of SEQ ID NO: 12, or a sequence having 90% sequence identity thereto.

In another aspect, the disclosure provides isolated polynucleotides encoding the fusion polypeptides of the disclosure.

In another aspect, the disclosure provides compositions comprising a fusion polypeptide of the disclosure.

In some embodiments of the above aspects, ML2028 comprises the sequence of SEQ ID NO: 2. In some embodiments, ML2028 comprises the sequence of SEQ ID NO: 4. In some embodiments, ML2055 comprises the sequence of SEQ ID NO: 6. In some embodiments, ML2380 comprises the sequence of SEQ ID NO: 8. In some embodiments, ML2531 comprises the sequence of SEQ ID NO: 10.

In some embodiments of compositions of the disclosure, the composition further includes an immunostimulant. In some embodiments, the immunostimulant is selected from the group consisting of a CpG-containing oligonucleotide, synthetic lipid A, MPL™, 3D-MPL™, saponins, saponin mimetics, AGPs, Toll-like receptor agonists, or a combination thereof. In some embodiments, the immunostimulant is selected from the group consisting of a TLR4 agonist, a TLR7/8 agonist and a TLR9 agonist. In some embodiments, the immunostimulant is selected from the group consisting of GLA, CpG-containing oligonucleotide, imiquimod, gardiquimod and resiquimod.

In some embodiments the immunostimulant is GLA, having the following structure:

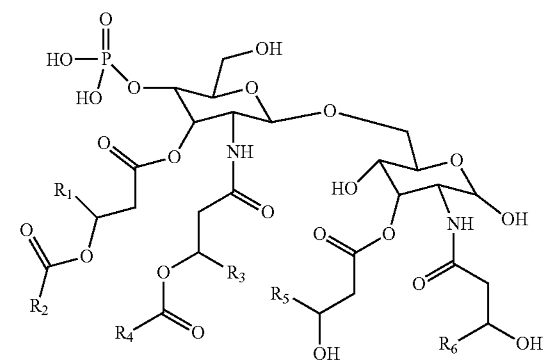

wherein $R^1$, $R^3$, $R^5$ and $R^6$ are $C_{11}$-$C_{20}$ alkyl; and $R^2$ and $R^4$ are $C_9$-$C_{20}$ alkyl. In some embodiments, $R^1$, $R^3$, $R^5$ and $R^6$ are $C_{11-14}$ alkyl; and $R^2$ and $R^4$ are $C_{12-15}$ alkyl. In some embodiments, $R^1$, $R^3$, $R^5$ and $R^6$ are $C_{11}$ alkyl; and $R^2$ and $R^4$ are $C_{13}$ alkyl. In some embodiments, $R^1$, $R^3$, $R^5$ and $R^6$ are $C_{11}$ alkyl; and $R^2$ and $R^4$ are $C_9$ alkyl.

In some embodiments, the immunostimulant has the following structure:

In some embodiments, the immunostimulant has the following structure:
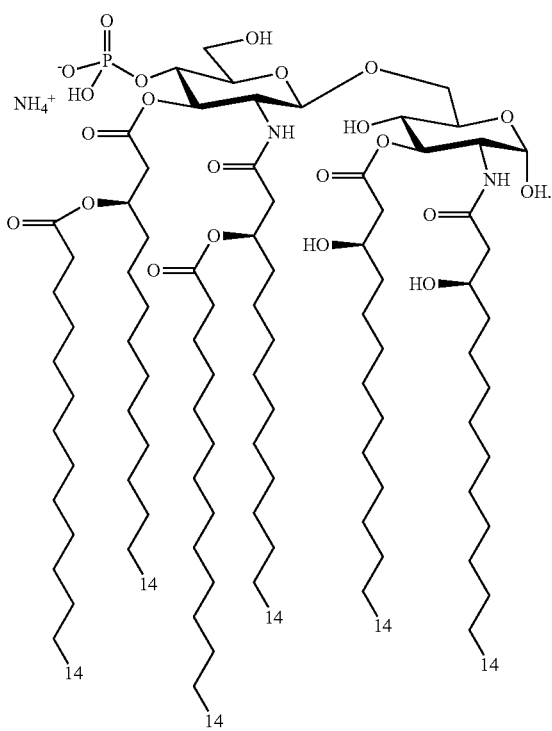

In another aspect, the disclosure provides methods for stimulating an immune response against *M. leprae* in a mammal comprising administering to a mammal in need thereof a composition of the disclosure. In some embodiments, the method further comprises administering to the mammal *M. bovis* BCG vaccine. In some embodiments, *M. bovis* BCG vaccine was previously administered to the mammal. In some embodiments, the mammal has not been exposed to *M. leprae*. In some embodiments, the mammal has been exposed to *M. leprae*. In some embodiments, the mammal is a human healthy household contact of a human identified as being infected with *M. leprae*. In some embodiments, the mammal has been infected by *M. leprae*. In some embodiments, the mammal exhibits signs or symptoms of infection by *M. leprae*.

In another aspect, the disclosure provides methods for stimulating an immune response against a tuberculosis-causing *mycobacterium* in a mammal comprising administering to a mammal in need thereof a composition of the disclosure.

In another aspect, the disclosure provides methods for treating an *M. leprae* infection in a mammal, the method comprising administering to a mammal having an *M. leprae* infection a composition of the disclosure. In some embodiments, the method further comprises administering to the mammal one or more chemotherapeutic agents. In some embodiments, the one or more chemotherapeutic agents comprise one or more agents selected from the group consisting of dapsone, rifampicin, clofazimine, ofloxacin, minocycline, gatifloxacin, linezolid, and PA 824. In some embodiments, the mammal is first administered one or more chemotherapeutic agents over a period of time and subsequently administered the composition. In some embodiments, the mammal is first administered the composition and subsequently administered one or more chemotherapeutic agents over a period of time. In some embodiments, administration of the one or more chemotherapeutic agents and the composition is concurrent. In some embodiments, the method further comprises administering the composition to the mammal one or more subsequent times. In some embodiments, the method further comprises administering to the mammal *M. bovis* BCG vaccine. In some embodiments, *M. bovis* BCG vaccine was previously administered to the mammal. In some embodiments, the mammal does not exhibit signs or symptoms of infection by *M. leprae*. In some embodiments, the mammal has indeterminate or tuberculoid presentation. In some embodiments, the mammal has paucibacillary leprosy. In some embodiments, the mammal has multibacillary leprosy. In some embodiments, the mammal has lepromatous leprosy. In some embodiments, the mammal has borderline lepromatous leprosy. In some embodiments, the mammal has mid-borderline leprosy. In some embodiments, the mammal has borderline tuberculoid leprosy. In some embodiments, the mammal has tuberculoid leprosy. In some embodiments, the mammal is infected with a multidrug resistant *M. leprae*.

In another aspect, the disclosure provides methods for reducing the time course of chemotherapy against an *M. leprae* infection, the method comprising administering to a mammal having an *M. leprae* infection a composition of the disclosure in conjunction with the chemotherapy, where the composition induces an immune response against *M. leprae*, thereby providing for a reduced time course of the chemotherapy against an *M. leprae* infection. In some embodiments, the time course of chemotherapy is shortened to no more than about 3 months, about 5 months, or about 7 months.

In some embodiments of the methods of the disclosure, the mammal is a human.

In another aspect, the disclosure provides a method for detecting *M. leprae* infection in a biological sample, comprising: (a) contacting a biological sample with a polypeptide (including a fusion polypeptide) as described herein; and (b) detecting in the biological sample the presence of antibodies that bind to the fusion polypeptide, thereby detecting *M. leprae* infection in a biological sample. Any suitable biological sample type may be analyzed by the method, illustrative examples of which may include, for example, sera, blood, saliva, skin, and nasal secretion.

In certain embodiments of the disclosed diagnostic methods, the polypeptide (including a fusion polypeptide) is bound to a solid support. Accordingly, the present disclosure further provides diagnostic reagents comprising a polypeptide (including a fusion polypeptide) as described herein, immobilized on a solid support.

Diagnostic kits for detecting *M. leprae* infection in a biological sample are also provided, generally comprising a polypeptide (including a fusion polypeptide) as described herein and a detection reagent. It will be understood that the kit may employ a polypeptide (including a fusion polypeptide) of the disclosure in any of a variety of assay formats known in the art, including, for example, a lateral flow test strip assay, a dual path platform (DPP) assay and an ELISA assay. These kits and compositions of the disclosure can offer valuable point of care diagnostic information. Furthermore, the kits and compositions can also be advantageously used as test-of-cure kits for monitoring the status of infection in an infected individual over time and/or in response to treatment.

Treatment kits for treating an *M. leprae* infection in a mammal are also provided, generally comprising a composition of the disclosure.

It is to be understood that one, some, or all of the properties of the various embodiments described herein may be combined to form other embodiments of the present disclosure. These and other aspects of the present disclosure will become apparent upon reference to the following detailed description and attached drawings. All references disclosed herein are hereby incorporated by reference in their entirety as if each was incorporated individually.

Figure 1A:
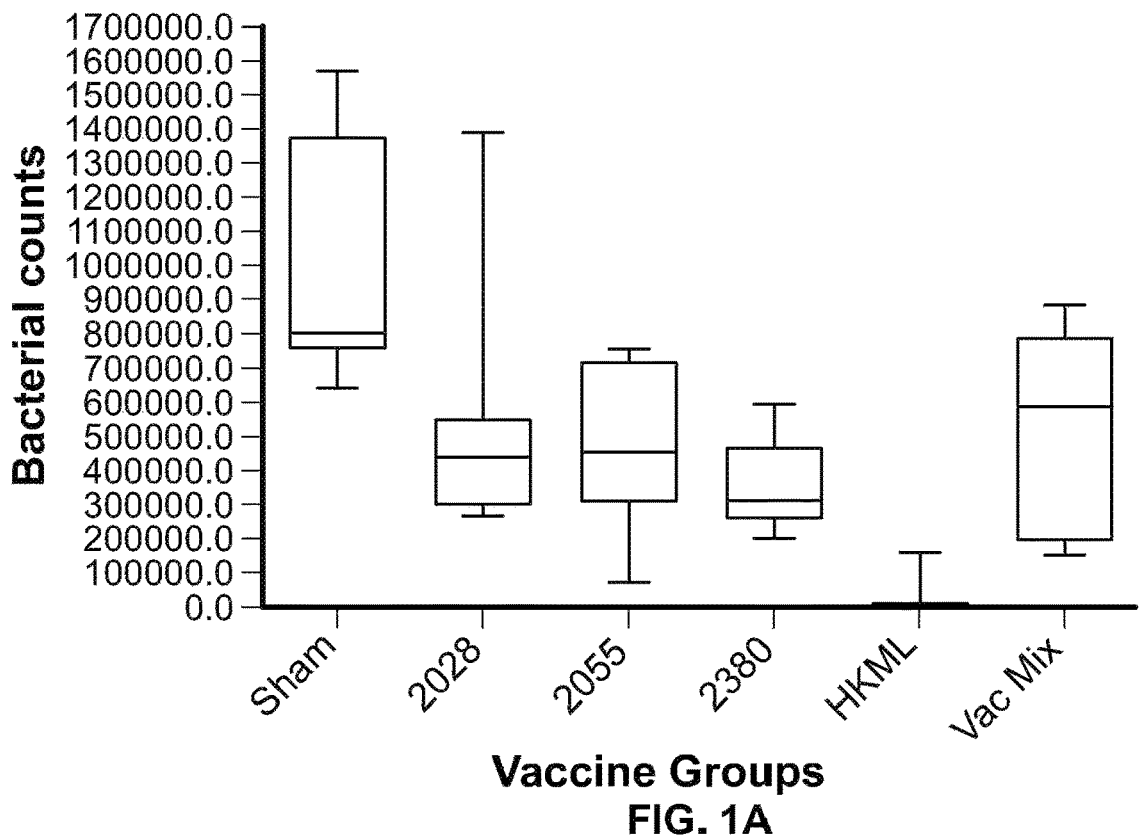
FIG. 1A shows the antigens, ML2028, ML2055 and ML2380, administered individually compared to the sham treatment and heat-killed M. leprae.
Figure 1B:
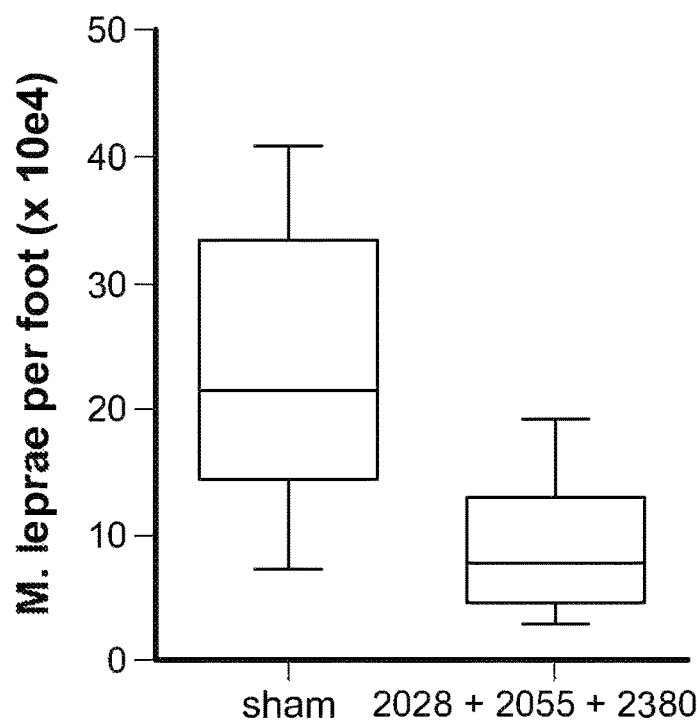
FIG. 1B shows the results of administ other embodiments, using the polypeptides including fusion polypeptides described herein in methods of treating mammals having an *M. leprae* infection. The present disclosure also contemplates, in other embodiments, using the polypeptides including fusion polypeptides described herein in diagnostic applications, including, but not limited to, diagnosis and whole blood assays, preferably in a format amenable to providing rapid, point of care diagnostic results, such as a lateral flow assay or a dual path platform assay.
Figure 1C:
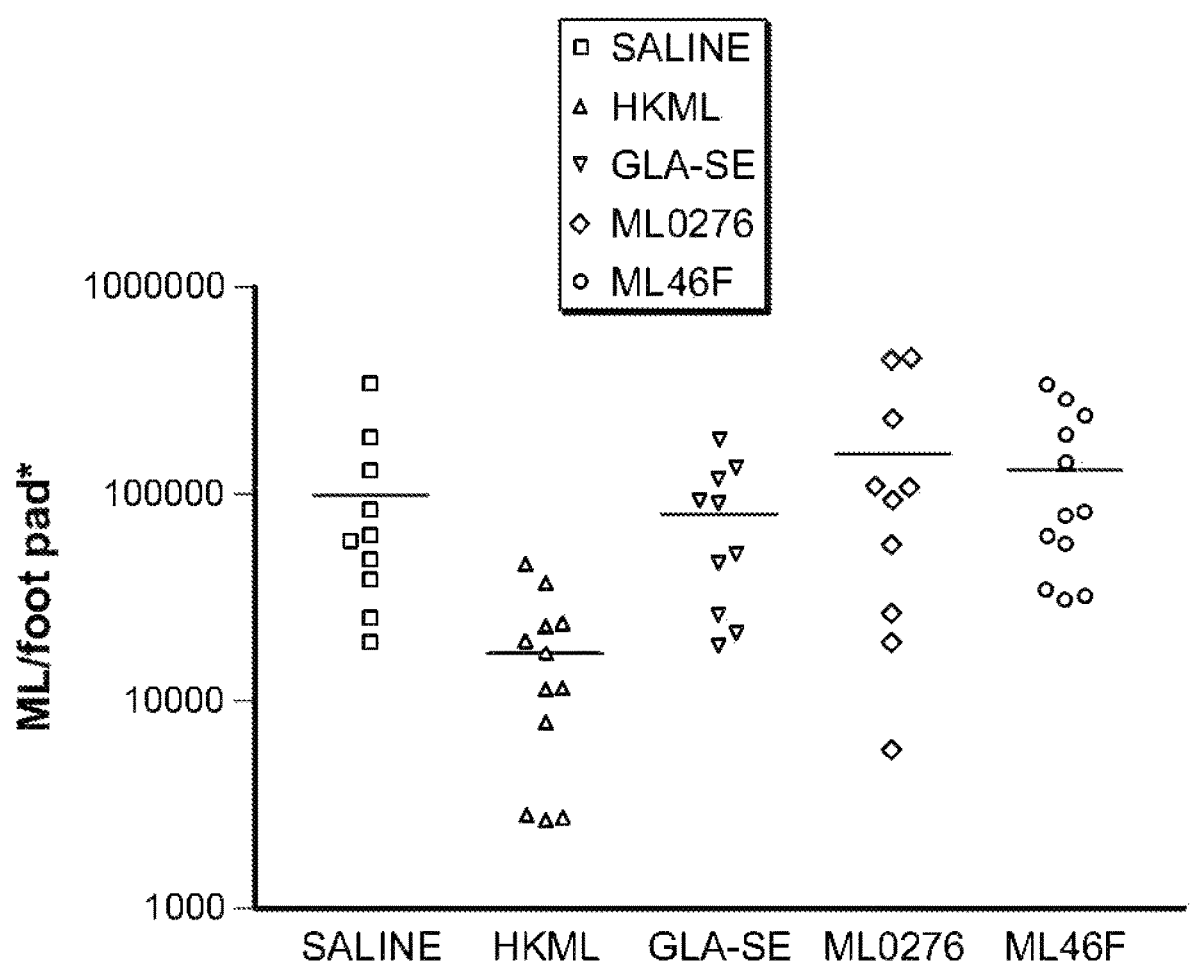
FIG. 1: Immunization with recombinant antigens formulated in GLA-SE reduce M. leprae burden. Mice were injected s.c. with antigens/GLA-SE at biweekly intervals, for a total of 3 immunizations. One month after the last immunization mice were infected with $1 \times 10^4$ M. leprae in each foot, and bacterial burdens determined 12 months later. Results are shown as mean and SE. Mann-Whitney test was used to calculate p-values between each group; n=6 per group.
Figure 2A:
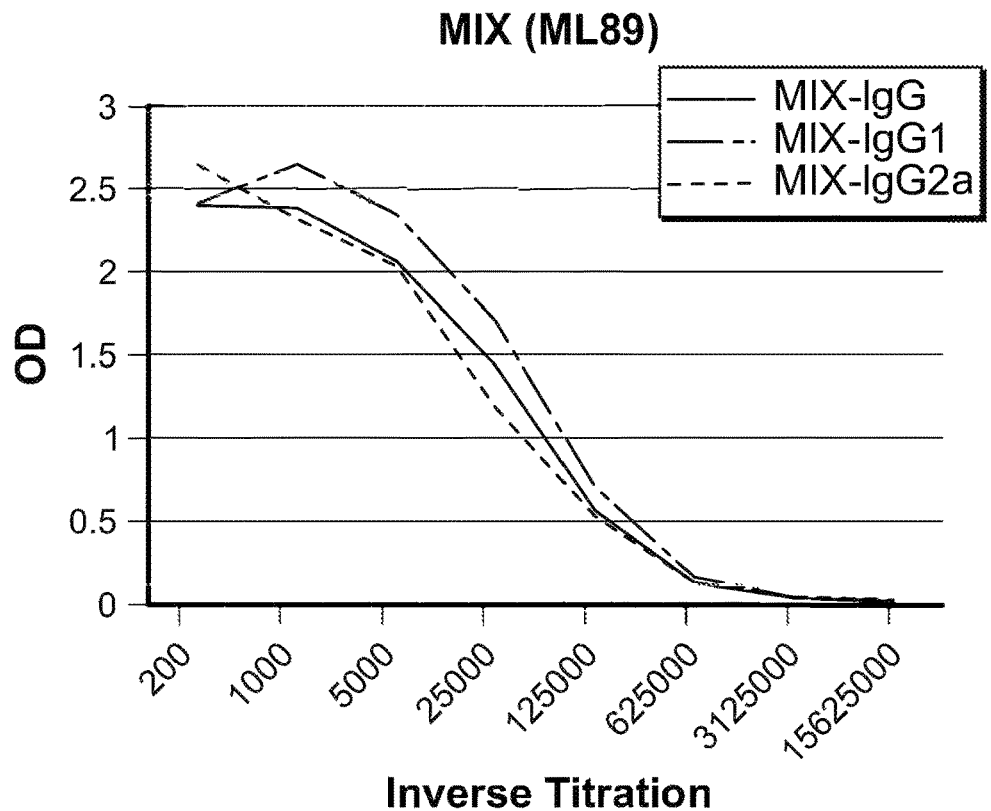
Figure 2B:
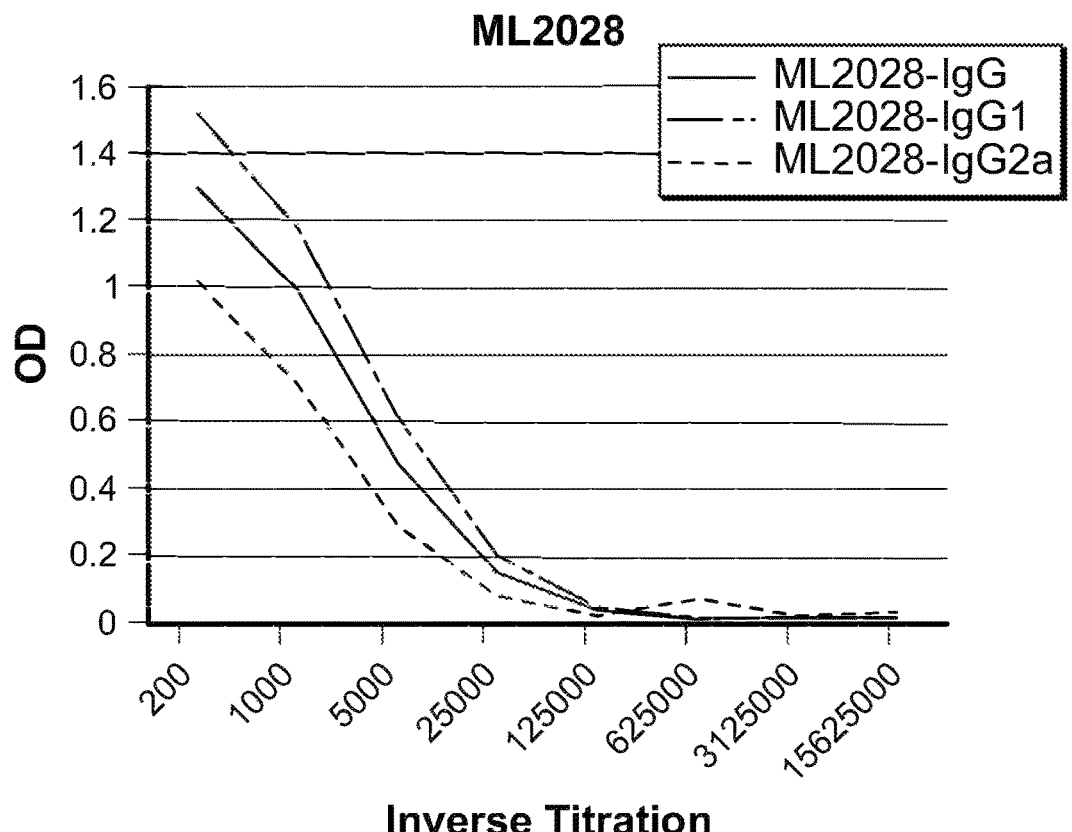
Figure 2C:
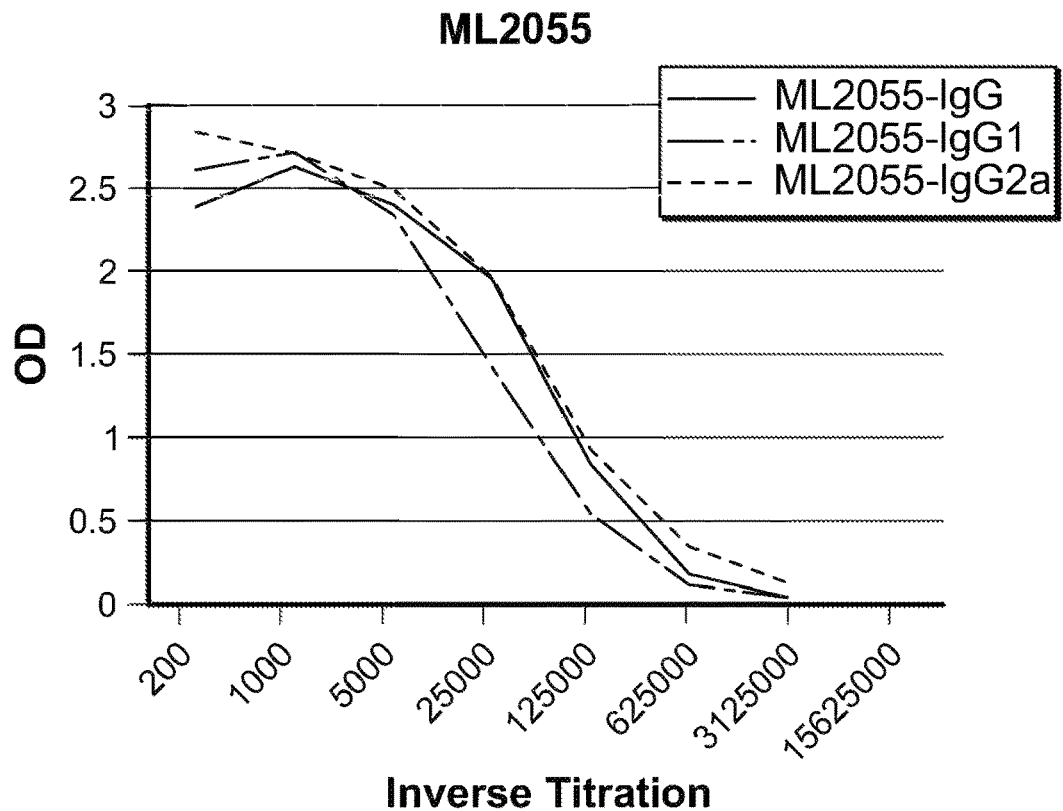
Figure 2D:
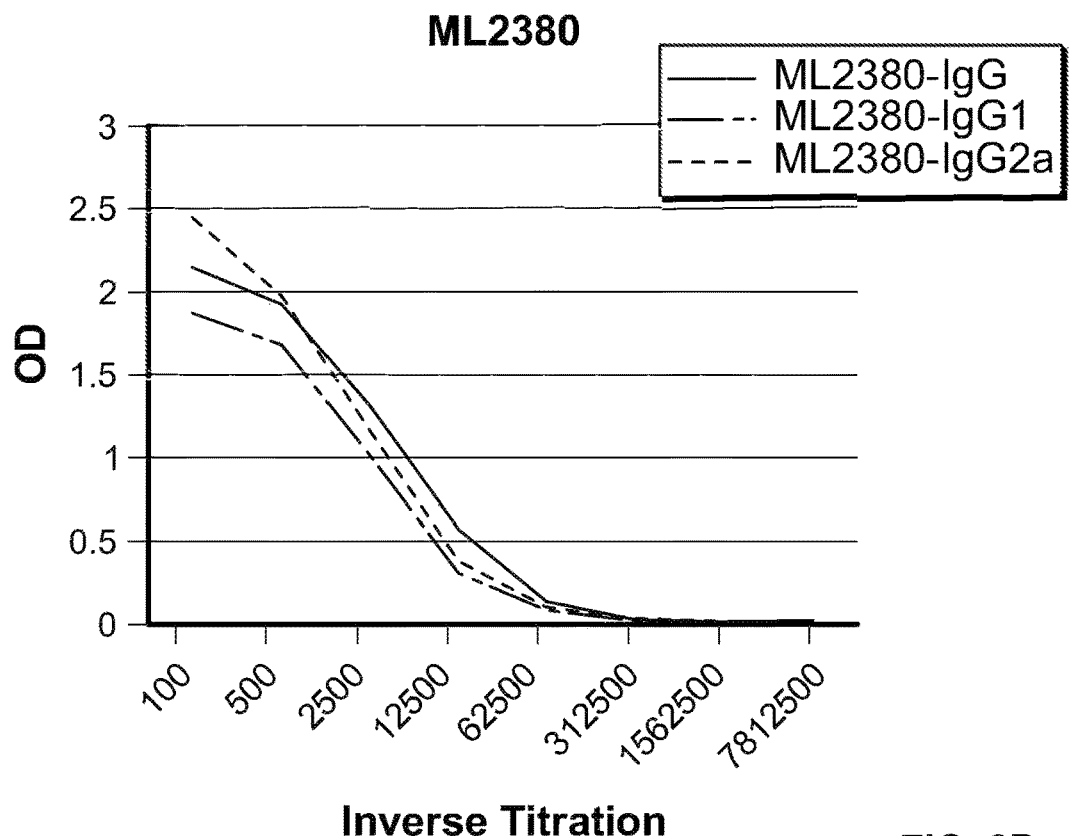
Figure 3A:
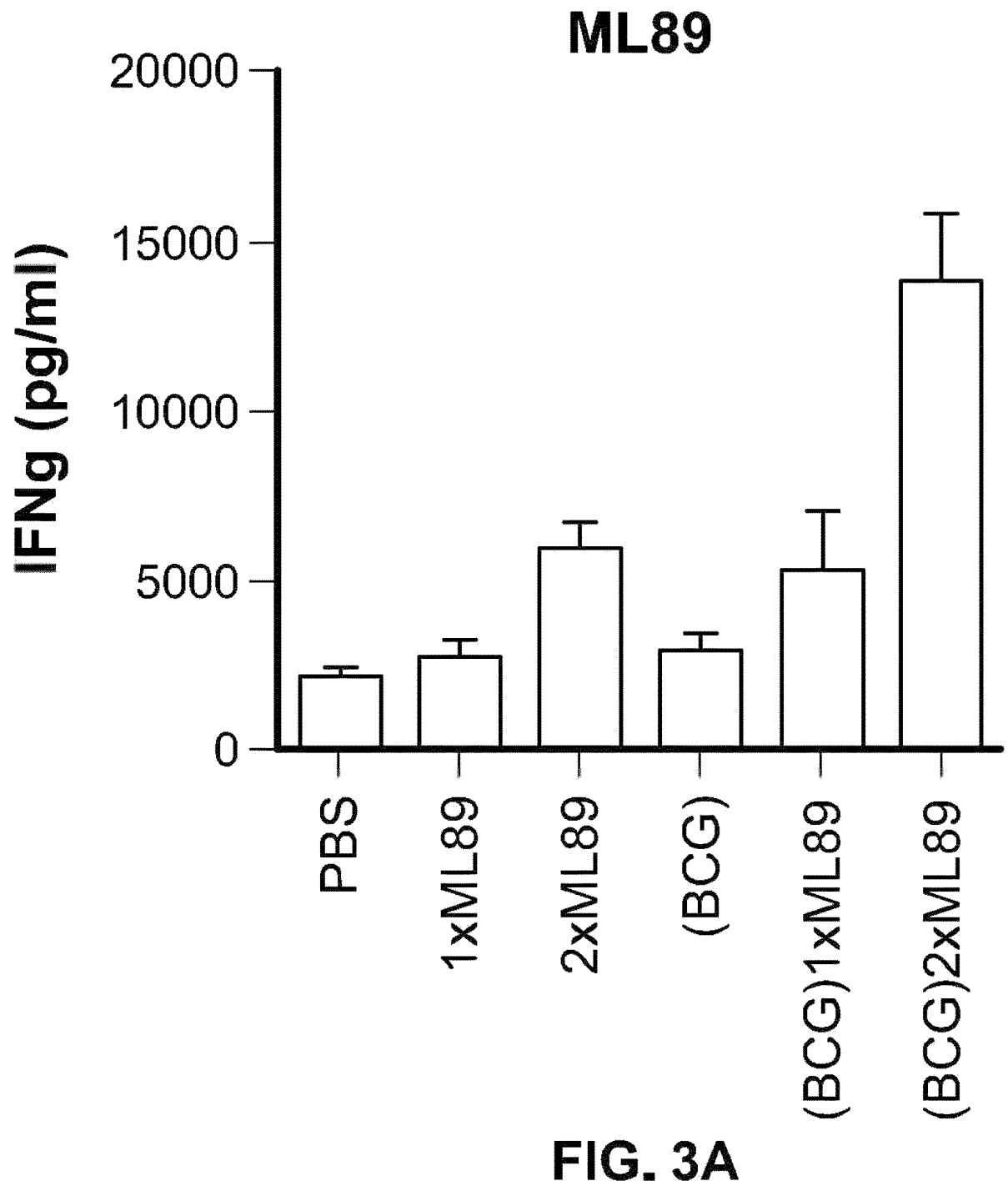
Figure 3B:
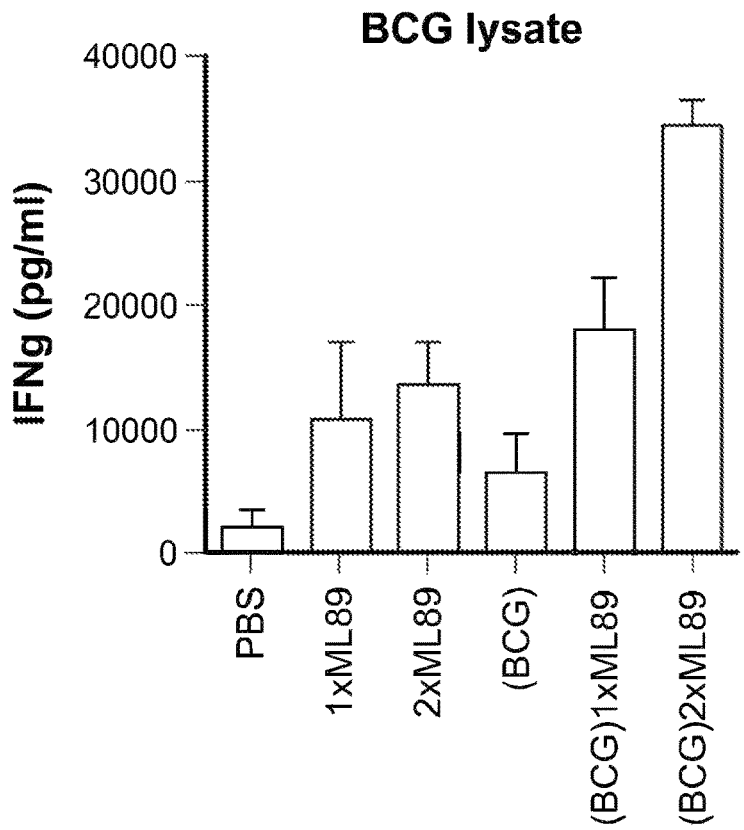
Figure 3C:
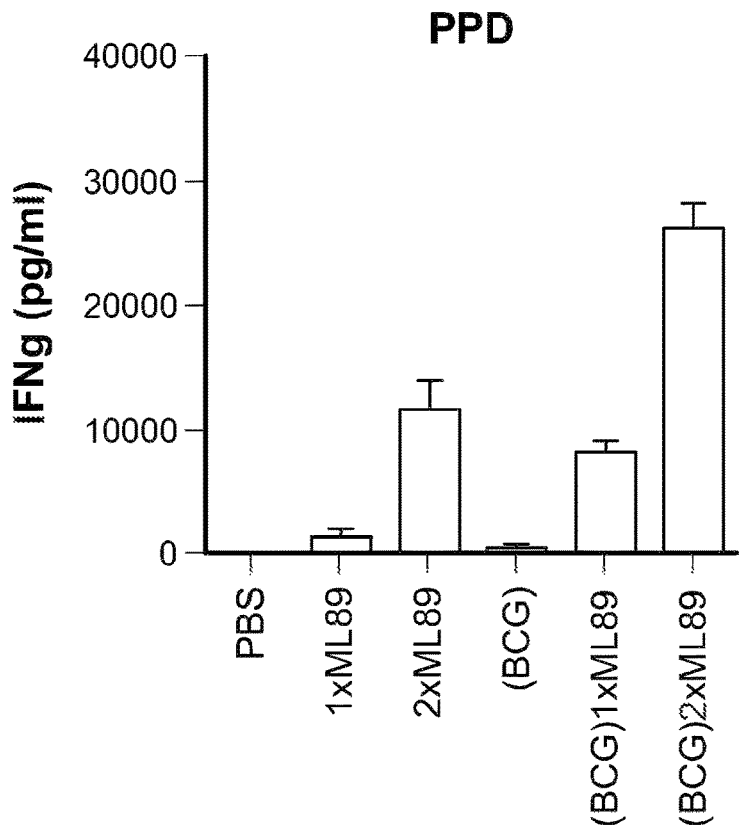
Figure 3D:
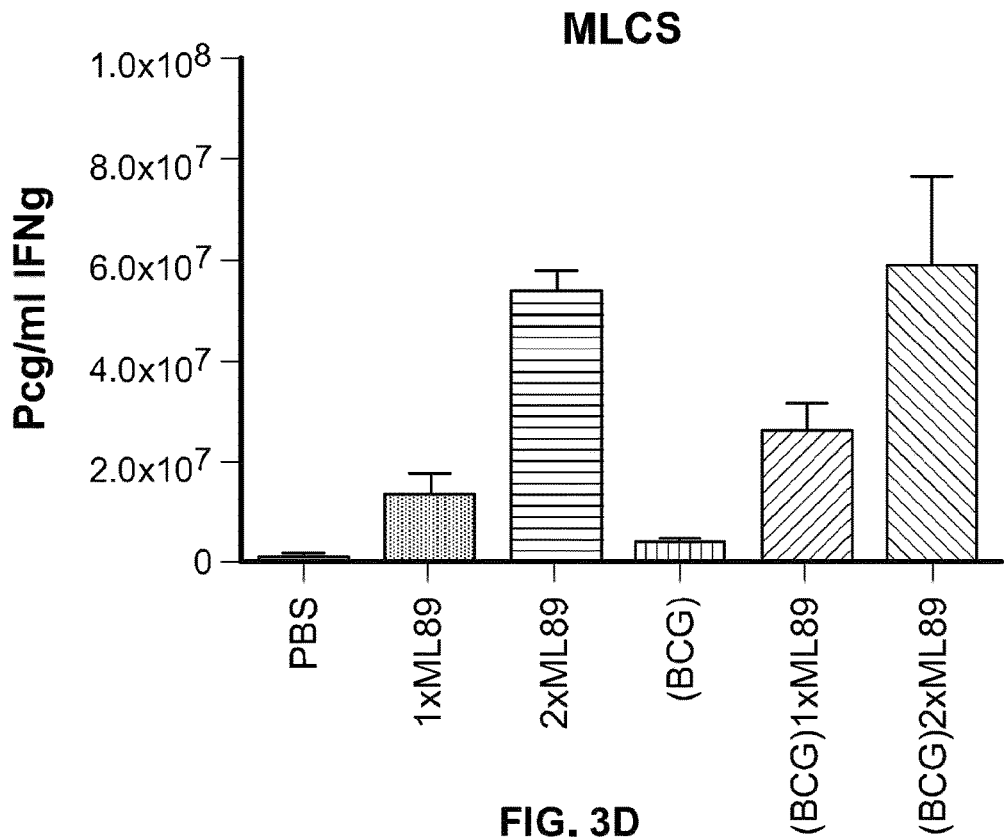
Figure 3E:
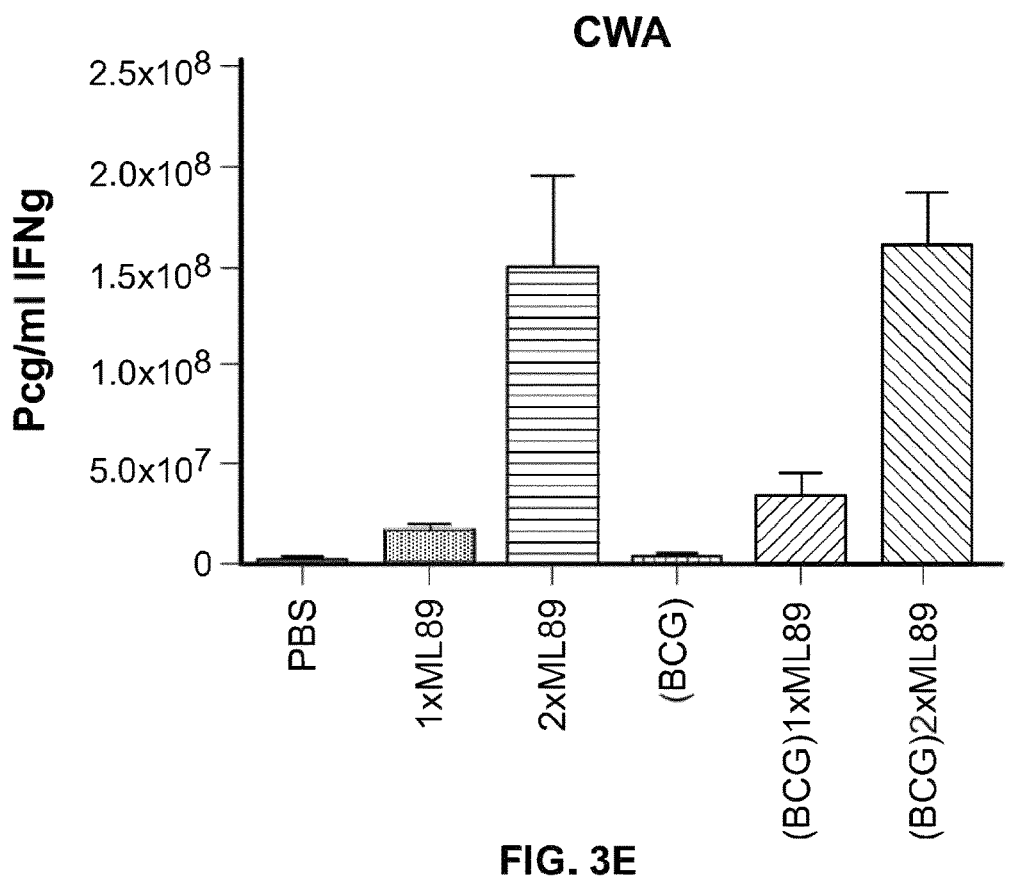
Figure 4A:
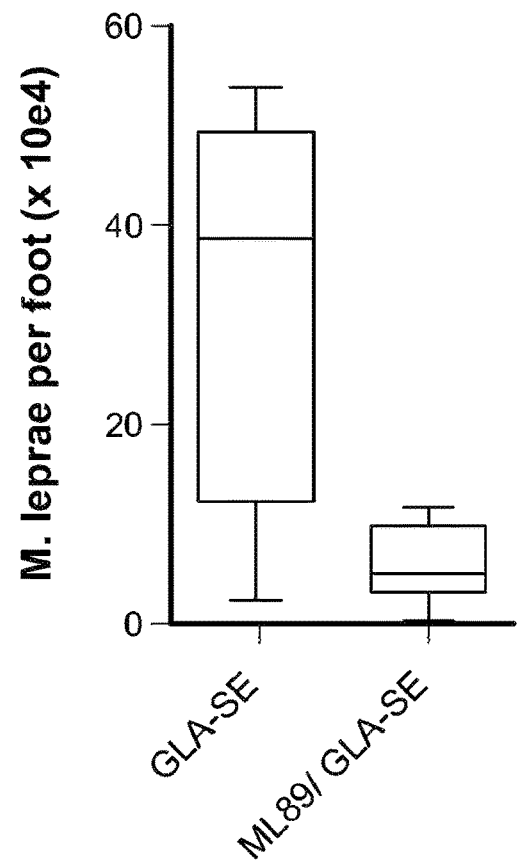
Figure 4B:
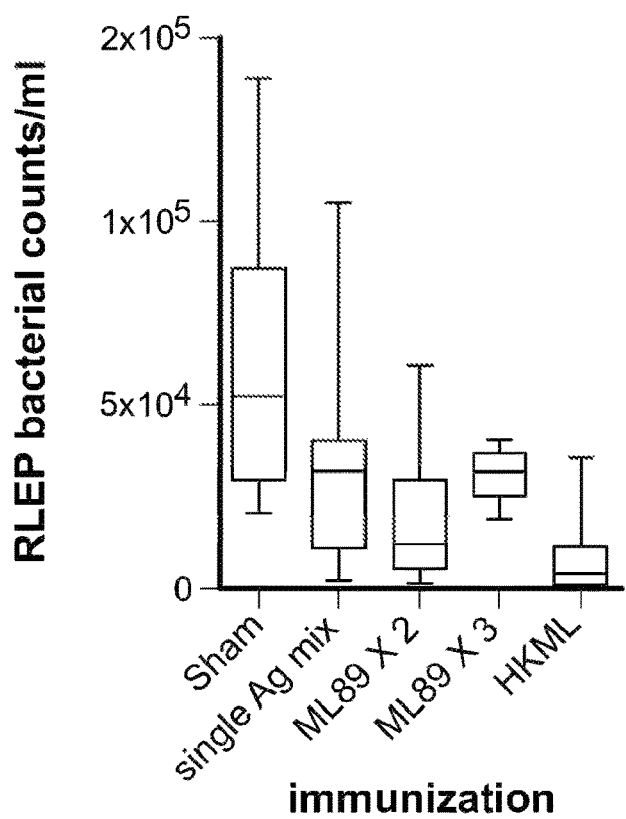

*M. Leprae* Antigens and Fusion Polypeptides and Uses Therefor

In a general aspect, the present disclosure provides *M. leprae* antigens, as described herein, including fusion polypeptides and compositions containing the same.

In some embodiments the disclosure provides compositions comprising at least two *Mycobacterium leprae* (*M. leprae*) antigens selected from the group consisting of ML2028, ML2055, and ML2380, or at least two *M. leprae* antigens each having at least 90% amino acid sequence identity to ML2028, ML2055, or ML2380. In some embodiments, the composition comprises ML2028 and ML2055; or an *M. leprae* antigen having at least 90% amino acid identity to ML2028 and an *M. leprae* antigen having at least 90% amino acid identity to ML2055. In some embodiments, the composition comprises ML2028 and ML2380; or an *M. leprae* antigen having at least 90% amino acid identity to ML2028 and an *M. leprae* antigen having at least 90% amino acid identity to ML2380. In some embodiments, the composition comprises ML2055 and ML2380; or an *M. leprae* antigen having at least 90% amino acid identity to ML2055 and an *M. leprae* antigen having at least 90% amino acid identity to ML2380. In some embodiments, the composition comprises ML2028, ML2055, and ML2380; or an *M. leprae* antigen having at least 90% amino acid identity to ML2028, an *M. leprae* antigen having at least 90% amino acid identity to ML2055, and an *M. leprae* antigen having at least 90% amino acid identity to ML2380. In some embodiments, the composition further comprises ML2531 or an *M. leprae* antigen having at least 90% amino acid sequence identity to ML2531.

In some embodiments the disclosure provides fusion polypeptides comprising at least two *Mycobacterium leprae* (*M. leprae*) antigens selected from the group consisting of ML2028, ML2055, and ML2380, or at least two *M. leprae* antigens each having at least 90% amino acid sequence identity to ML2028, ML2055, or ML2380. In some embodiments, the fusion polypeptide comprises ML2028 and ML2055; or an *M. leprae* antigen having at least 90% amino acid identity to ML2028 and an *M. leprae* antigen having at least 90% amino acid identity to ML2055. In some embodiments, the fusion polypeptide comprises ML2028 and ML2380; or an *M. leprae* antigen having at least 90% amino acid identity to ML2028 and an *M. leprae* antigen having at least 90% amino acid identity to ML2380. In some embodiments, the fusion polypeptide comprises ML2055 and ML2380; or an *M. leprae* antigen having at least 90% amino acid identity to ML2055 and an *M. leprae* antigen having at least 90% amino acid identity to ML2380. In some embodiments, the fusion polypeptide comprises ML2028, ML20SS, and ML2380; or an *M. leprae* antigen having at least 90% amino acid identity to ML2028, an *M. leprae* antigen having at least 90% amino acid identity to ML2055, and an *M. leprae* antigen having at least 90% amino acid identity to ML2380. In some embodiments, the fusion polypeptide further comprises *M. leprae* antigen ML2531. In some embodiments, the fusion polypeptide comprises the sequence of SEQ ID NO: 12, or a sequence having 90% sequence identity thereto.

In some embodiments, compositions comprising antigens and fusion polypeptides described herein can generate an immune response or an effective immune response to *M. leprae*. The immune response may have one or more of the following characteristics: 1) a reduction in bacterial burden in immunized hosts upon challenge with an *M. leprae* infection; 2) secretion of IFNγ in in vitro spleen cell cultures from mice immunized with the compositions of the disclosure upon incubation with the matched fusion polypeptide or individual antigens of the fusion polypeptide; 3) IFNγ secretion in vitro spleen cell cultures from mice immunized with the compositions of the disclosure following incubation with crude *M. leprae,* 4) generation of antigen-specific multifunctional Th1 cells, for example CD4 T cells that produce multiple cytokines indicative of a Th1 phenotype such as the combined production of IFNγ, TNF and IL-2 or IFNγ and TNF; or 5) improvement or enhancement of the immune recognition of one or more antigen(s), when presented in the context of a fusion polypeptide, as measured for example by the secretion of cytokines such IFNγ, or the titer of presence of antibodies or cellular responses to the antigen. Methods for testing one or more of the above immune responses are known in the art and are described in detail in Examples.

Different *M. leprae* antigens in the fusion polypeptides may be arranged in the fusion polypeptide in any order. For example, any particular polypeptide of the fusion polypeptide may be located towards the C-terminal end of the fusion polypeptide or the N-terminal end of the polypeptide or in the center of the fusion polypeptide {i.e., located in between at least two other polypeptides in the fusion polypeptide). Different *M. leprae* antigens may be linked by a linker sequence of any length (e.g., 2-20 amino acids).

In one embodiment, the fusion polypeptide consists of four *M. leprae* antigens: ML2531 (ESAT-6-like protein EsxR), ML2380 (hypothetical protein), ML2055 (cell surface protein associated with virulence), and ML2028$_{39-327}$ (antigen 85B, mature chain without signal sequence). The full native sequence of ML2531, ML2380, ML2055 are present, while ML2028$_{39-327}$ represents the mature chain without the signal sequence residues 1 through 38. There is a two-residue linker sequence inserted between each of the antigens to improve expression and recovery. The resulting 831 amino acid fusion protein has a predicted molecular weight of 89,062 Da. The polynucleotide sequence encoding the fusion polypeptide is SEQ ID NO: 11, and the amino acid sequence of the fusion polypeptide is SEQ ID NO: 12. Such fusion polypeptide may be referred to as LEP-F1, ML89, or LepVax.

A schematic of one embodiment of the fusion polypeptide is below.

| ML2531 | ML2380 | ML2055 | ML2028$_{39-327}$ |
| --- | --- | --- | --- |
| 10 kDa | 17 kDa | 30 kDa | 31 kDa |

As used herein, the term "polypeptide" or "protein" encompasses amino acid chains of any length, including full length proteins, wherein the amino acid residues are linked by covalent bonds. An antigen is a polypeptide comprising an immunogenic portion of a *M. leprae* polypeptide or protein and may consist solely of an immunogenic portion, may contain two or more immunogenic portions and/or may contain additional sequences. The additional sequences may be derived from a native *M. leprae* polypeptide or protein or may be heterologous, and such heterologous sequences may (but need not) be immunogenic.

An "isolated polypeptide" is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. One of ordinary skill in the art would appreciate that antigenic polypeptide fragments could also be obtained from those already available in the art. Polypeptides of the disclosure, antigenic/immunogenic fragments thereof, and other variants may be prepared using conventional recombinant and/or synthetic techniques.

The *M. leprae* antigens used in a fusion polypeptide of the present disclosure can be full length, substantially full length polypeptides, or variants thereof as described herein. Alternatively, a fusion polypeptide or composition of the disclosure can comprise or consist of immunogenic portions or fragments of a full length *M. leprae* polypeptide, or variants thereof.

In certain embodiments, an immunogenic portion of a *M. leprae* polypeptide is a portion that is capable of eliciting an immune response (i.e., cellular and/or humoral) in a presently or previously *M. leprae*-infected patient (such as a human or a mammal (e.g., an armadillo)) and/or in cultures of spleen cells, lymph node cells or peripheral blood mononuclear cells (PBMC) isolated from presently or previously *M. leprae*-infected individuals. The cells in which a response is elicited may comprise a mixture of cell types or may contain isolated component cells (including, but not limited to, T-cells, NK cells, macrophages, monocytes and/or B cells). In a particular embodiment, immunogenic portions of a fusion polypeptide of the disclosure are capable of inducing T-cell proliferation and/or a predominantly Th1-type cytokine response (e.g., IL-2, IFN-γ, and/or TNFα production by T-cells and/or NK cells, and/or IL-12 production by monocytes, macrophages and/or B cells). Immunogenic portions of the polypeptides described herein may generally be identified using techniques known to those of ordinary skill in the art, including the representative methods summarized in Paul, Fundamental Immunology, 5th ed., Lippincott Williams & Wilkins, 2003 and references cited therein. Such techniques include screening fusion polypeptides for the ability to react with antigen-specific antibodies, antisera and/or T cell lines or clones. As used herein, antisera and antibodies are "antigen-specific" if they specifically bind to an antigen (i.e., they react with the protein in an immunoassay, and do not react detectably with unrelated proteins). Such antisera and antibodies may be prepared as described herein and using well-known techniques.

Immunogenic portions of an *M. leprae* polypeptide can be essentially any length; provided they retain one or more of the immunogenic regions that are responsible for or contribute to the in vivo protection provided against leprosy by one or more antigens of fusion polypeptides of the disclosure, as disclosed herein. In one embodiment, the ability of an immunogenic portion to react with antigen-specific antisera may be enhanced or unchanged, relative to the native protein, or may be diminished by less than 50%, and preferably less than 20%, relative to the native protein. Illustrative portions will generally be at least 10, 15, 25, 50, 150, 200, 250, 300, or 350 amino acids in length, or more, up to and including full length *M. leprae* polypeptide.

In some embodiments, a *M. leprae* antigen described herein includes ML2028, ML2055, ML2380, and ML2531. In some embodiments, these *M. leprae* antigens include any naturally occurring variants.

As would be recognized by the skilled artisan, a composition of the disclosure may also comprise one or more polypeptides that are immunologically reactive with T cells and/or antibodies generated against a polypeptide of the disclosure, particularly a polypeptide having an amino acid sequence disclosed herein, or to an immunogenic fragment or variant thereof. In a specific embodiment, the polypeptide is a fusion polypeptide, as described herein.

As noted, in various embodiments of the present disclosure, fusion polypeptides generally comprise at least an immunogenic portion or variant of the *M. leprae* polypeptides described herein. In some instances, preferred immunogenic portions will be identified that have a level of immunogenic activity greater than that of the corresponding full-length polypeptide, e.g., having greater than about 100% or 150% or more immunogenic activity. In particular embodiments, the immunogenicity of the full-length fusion polypeptide will have additive, or greater than additive immunogenicity contributed by of each of the antigenic/immunogenic portions contained therein.

In another aspect, fusion polypeptides of the present disclosure may contain multiple copies of polypeptide fragments, repeats of polypeptide fragments, or multimeric polypeptide fragments, including antigenic/immunogenic fragments, such as *M. leprae* polypeptides comprising at least about 1, 2, 3, 4, 5, 6, 7, 8, 9, 10 or more contiguous fragments of a *M. leprae* polypeptide, in any order, and including all lengths of a polypeptide composition set forth herein, or those encoded by a polynucleotide sequence set forth herein.

In some embodiments, the ML2028 antigen comprises the sequence of SEQ ID NO: 2 or SEQ ID NO: 4, or a sequence having at least 90% identity (e.g., at least 90%, at least 91%, at least 92%, at least 93%, at least 94%, at least 95%, at least 96%, at least 97%, at least 98%, or at least 99%) to SEQ ID NO: 2 or to SEQ ID NO: 4. In some embodiments, the ML2055 antigen comprises the sequence of SEQ ID NO: 6, or a sequence having at least 90% identity (e.g., at least 90%, at least 91%, at least 92%, at least 93%, at least 94%, at least 95%, at least 96%, at least 97%, at least 98%, or at least 99%) to SEQ ID NO: 6. In some embodiments, the ML2380 antigen comprises the sequence of SEQ ID NO: 8, or a sequence having at least 90% identity (e.g., at least 90%, at least 91%, at least 92%, at least 93%, at least 94%, at least 95%, at least 96%, at least 97%, at least 98%, or at least 99%) to SEQ ID NO: 8. In some embodiments, the ML2531 antigen comprises the sequence of SEQ ID NO: 10, or a sequence having at least 90% identity (e.g., at least 90%, at least 91%, at least 92%, at least 93%, at least 94%, at least 95%, at least 96%, at least 97%, at least 98%, or at least 99%) to SEQ ID NO: 10.

In another aspect, the disclosure provides a fusion polypeptide comprising, consisting of, or consisting essentially of the amino acid sequence set forth in SEQ ID NO: 12, or a sequence having at least 90% identity thereto (e.g., at least 90%, at least 91%, at least 92%, at least 93%, at least 94%, at least 95%, at least 96%, at least 97%, at least 98%, or at least 99% identity thereto).

In yet another aspect, the present disclosure provides fusion polypeptides comprising one or more variants of the *M. leprae* antigens described herein. Polypeptide variants generally encompassed by the present disclosure will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequence set forth herein.

In other related embodiments, a polypeptide "variant," includes polypeptides that differ from a native protein in one or more substitutions, deletions, additions and/or insertions, such that the desired immunogenicity of the variant polypeptide is not substantially diminished relative to a native polypeptide.

For example, certain variants of the disclosure include polypeptides of the disclosure that have been modified to replace one or more cysteine residues with alternative residues. Such polypeptides are referred to hereinafter as cysteine-modified polypeptides or cysteine-modified fusion polypeptides. Preferably, the modified polypeptides retain substantially the same or similar immunogenic properties as the corresponding unmodified polypeptides. In a more specific embodiment, cysteine residues are replaced with serine residues because of the similarity in the spatial arrangement of their respective side chains. However, it will be apparent to one skilled in the art that any amino acid that is incapable of interchain or intrachain disulfide bond formation can be used as a replacement for cysteine. When all or substantially all of the cysteine residues in a polypeptide or fusion polypeptide of this disclosure are replaced, the resulting cysteine-modified variant may be less prone to aggregation and thus easier to purify, more homogeneous, and/or obtainable in higher yields following purification.

In one embodiment, the ability of a variant to react with antigen-specific antisera may be enhanced or unchanged, relative to the native protein, or may be diminished by less than 50%, and preferably less than 20%, relative to a corresponding native or control polypeptide. In a particular embodiment, a variant of an *M. leprae* polypeptide is one capable of providing protection against *M. leprae* infection.

In particular embodiments, a fusion polypeptide of the present disclosure comprises at least 1, at least 2, at least 3, at least 4, at least 5, at least 6, at least 7, at least 8, at least 9, or at least 10 or more substitutions, deletions, additions and/or insertions within a *M. leprae* polypeptide, where the fusion polypeptide is capable of providing protection against an *M leprae* infection.

In related embodiments, a fusion polypeptide of the present disclosure comprises at least 1, at least 2, at least 3, at least 4, at least 5, at least 6, at least 7, at least 8, at least 9, or at least 10 or more substitutions, deletions, additions and/or insertions within a *M. leprae* polypeptide, where the fusion polypeptide is capable of serodiagnosis of *M. leprae*.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present disclosure and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the disclosure, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAG | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA CUC CUG CUU | |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA CGC CGG CGU | |
| Serine | Ser | S | AGC | AGU | UCA UCC UCG UCU | |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-Histidine tag (6×His), GST, MBP, TAP/TAG, FLAG epitope, MYC epitope, V5 epitope, VSV-G epitope, etc.), or to enhance binding of the polypeptide to a solid support. For example, a polypeptide may be conjugated to an immunoglobulin Fc region.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Alignment of sequences for comparison may be conducted using, for example, the Megalign program in the Lasergene suite of bioinformatics software (DNASTAR, Inc., Madison, WI), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-"645 Methods in Enzymology vol. 183, Academic Press, Inc., San Diego, CA; Higgins, D. G. and Sharp, P. M. (1989) CABIOS 5:151-153; Myers, E. W. and Muller W. (1988) CABIOS 4: 11-17; Robinson, E. D. (1971) Comb. Theor 11: 105; Santou, N. Nes, M. (1987) MoL Biol. Evol. 4:406-425; Sneath, P. H. A. and Sokal, R. R. (1973) Numerical Taxonomy—the Principles and Practice of Numerical Taxonomy, Freeman Press, San Francisco, CA; Wilbur, W. J. and Lipman, D. J. (1983) Proc. Natl. Acad., Sci. USA 80:726-730.

Alternatively, alignment of sequences for comparison may be conducted by the local identity algorithm of Smith and Waterman (1981) Add. APL. Math 2:482, by the identity alignment algorithm of Needleman and Wunsch (1970) J. MoL Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

One example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, as noted above, the present disclosure encompasses polynucleotide and polypeptide sequences having substantial identity to the sequences disclosed herein, for example those comprising at least 70%, 75%, 80%, 85%, 90%, 95%, 96%, 97%, 98%, or 99% or higher, sequence identity compared to a polynucleotide or polypeptide sequence of this disclosure (e.g., as set out in SEQ ID NOs: 1-12) using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like. Furthermore, it would be understood by of ordinary skill in the art that fusion polypeptides of the present disclosure may comprise at least 2, at least 3, or at least 4 or more antigenic/immunogenic portions or fragments of a polypeptide comprising at least 70%, 75%, 80%, 85%, 90%, 95%, 96%, 97%, 98%, or 99% or higher, sequence identity to a M. leprae polypeptide that is capable of providing protection against M. leprae infection, or serodiagnosis of M. leprae.

In another aspect of the disclosure, fusion polypeptides are provided that comprise at least an immunogenic portion of a polypeptide and further comprise a heterologous fusion partner, as well as polynucleotides encoding such fusion polypeptides. For example, in one embodiment, a fusion polypeptide comprises one or more immunogenic portions or fragments of a M. leprae polypeptide and one or more additional immunogenic M. leprae sequences, which are joined via a peptide linkage into a single amino acid chain.

In another embodiment, a fusion polypeptide may comprise multiple M. leprae antigenic portions. In some embodiments, at least one of the portions in the fusion polypeptide is from ML2028, ML2055, or ML2380. In some embodiments, an immunogenic portion is a portion of an antigen that reacts with blood samples from M. leprae-infected individuals (i.e. an epitope is specifically bound by one or more antibodies and/or T-cells present in such blood samples).

In certain embodiments, a fusion polypeptide may further comprise at least one heterologous fusion partner having a sequence that assists in providing T helper epitopes (an immunological fusion partner), preferably T helper epitopes recognized by humans, or that assists in expressing the protein (an expression enhancer) at higher yields than the native recombinant protein. Certain preferred fusion partners include both immunological and expression-enhancing fusion partners. Other fusion partners may be selected so as to increase the solubility of the protein or to enable the protein to be targeted to desired intracellular compartments. Still further fusion partners include affinity tags, such as V5, 6×HIS, MYC, FLAG, and GST, which facilitate purification of the protein. It would be understood by one having ordinary skill in the art that those unrelated sequences may, but need not, be present in a fusion polypeptide used in accordance with the present disclosure. In another particular embodiment, an immunological fusion partner comprises an amino acid sequence derived from the protein known as LYTA, or a portion thereof (preferably a C-terminal portion). LYTA is derived from Streptococcus pneumoniae, which synthesizes an N-acetyl-L-alanine amidase known as amidase LYTA (encoded by the LytA gene; Gene 43:265-292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of E. coli C-LYTA expressing plasmids useful for expression of fusion proteins. Purification of hybrid proteins containing the C-LYTA fragment at the amino terminus has been described (see Biotechnology 10:795-798 (1992)). Within a particular embodiment, a repeat portion of LYTA may be incorporated into a fusion protein. A repeat portion is found in the C-terminal region starting at residue 178. A more particular repeat portion incorporates residues 188-305.

Fusion sequences may be joined directly (i.e., with no intervening amino acids) or may be joined by way of a linker sequence (e.g., Gly-Cys-Gly) that does not significantly diminish the immunogenic properties of the component polypeptides. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. Fusion polypeptides or fusion proteins can also include conservatively modified variants, polymorphic variants, alleles, mutants, subsequences, interspecies homologs, and immunogenic fragments of the antigens that make up the fusion protein.

Fusion polypeptides may generally be prepared using standard techniques, including recombinant technology, chemical conjugation and the like. For example, DNA sequences encoding the polypeptide components of a fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in frame. This permits translation into a single fusion polypeptide that retains or in some cases exceeds the biological activity of the component polypeptides.

A peptide linker sequence may be employed to separate the fusion components by a distance sufficient to ensure that each polypeptide folds into its desired secondary and/or tertiary structures. Such a peptide linker sequence may be incorporated into the fusion polypeptide using standard techniques well known in the art. Suitable peptide linker sequences may be chosen, for example, based on one or more of the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Certain preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

In addition to recombinant fusion polypeptide expression, *M. leprae* polypeptides, immunogenic portions, variants and fusions thereof may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (Merrifield, J. Am. Chem. Soc. 85:2149-2146, 1963). Equipment for automated synthesis of polypeptides is commercially available from suppliers such as Perkin Elmer/Applied BioSystems Division, Foster City, CA, and may be operated according to the manufacturer's instructions. Thus, for example, *M. leprae* antigens, or portions thereof, may be synthesized by this method.

Recombinant polypeptides containing portions and/or variants of a native *M. leprae* polypeptide may be readily prepared from a DNA sequence encoding the antigen, using well known and established techniques. In particular embodiments, a fusion polypeptide comprising *M. leprae* antigens may be readily prepared from a DNA sequence encoding the cloned fused antigens. For example, supernatants from suitable host/vector systems which secrete recombinant protein into culture media may be first concentrated using a commercially available filter. Following concentration, the concentrate may be applied to a suitable purification matrix such as an affinity matrix, a size exclusion chromatography matrix or an ion exchange resin.

Alternatively, any of a variety of expression vectors known to those of ordinary skill in the art may be employed to express recombinant polypeptides of this disclosure. Expression may be achieved in any appropriate host cell that has been transformed or transfected with an expression vector containing a polynucleotide that encodes a recombinant polypeptide. Preferably, the host cells are *E. coli*, yeast, an insect cell line (such as *Spodoptera* or *Trichoplusia*) or a mammalian cell line, including (but not limited to) CHO, COS, HEK-293T and NS-1. The DNA sequences expressed in this manner may encode naturally occurring proteins, and fusion proteins comprising *M. leprae* antigens, such as those described herein, portions thereof, and repeats or other variants of such proteins. Expressed fusion polypeptides of this disclosure are generally isolated in substantially pure form. Preferably, the fusion polypeptides are isolated to a purity of at least 80% by weight, more preferably, to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography.

Regardless of the method of preparation, the polypeptides or fusion polypeptides produced as described above are preferably immunogenic. In certain embodiments, for example, the polypeptides (or immunogenic portions thereof) are capable of eliciting an immune response in cultures of lymph node cells and/or peripheral blood mononuclear cells (PBMC) isolated from presently or previously *M. leprae*-infected individuals. More specifically, in certain embodiments, the antigens, and immunogenic portions thereof, have the ability to induce T-cell proliferation and/or to elicit a dominantly Th1-type cytokine response (e.g., IL-2, IFN-y, and/or TNF-a production by T-cells and/or NK cells; and/or IL-12 production by monocytes, macrophages and/or B cells) in cells isolated from presently or previously *M. leprae*-infected individuals. A *M. leprae*-infected individual may be afflicted with a form of leprosy (such as paucibacillary (PB), multibacillary (MB), lepromatous leprosy (LL), borderline lepromatous (BL), mid-borderline (BB), borderline tuberculoid (BT), or tuberculoid leprosy (TT)) or may be asymptomatic. Such individuals may be identified using methods known to those of ordinary skill in the art. Individuals with leprosy may be identified based on clinical findings associated with, for example, at least one of the following: appearance of hypopigmented or reddish lesion with hypoesthesia, presence of acid fast bacilli in lymph node smears and compatible skin lesion histopathology. Asymptomatic individuals are infected individuals who have no signs or symptoms of the disease. Such individuals can be identified, for example, based on a positive serological test and/or skin test.

The term "PBMC," which refers to a preparation of nucleated cells consisting primarily of lymphocytes and monocytes that are present in peripheral blood, encompasses both mixtures of cells and preparations of one or more purified cell types. PBMC may be isolated by methods known to those in the art. For example, PBMC may be isolated by density centrifugation through, for example, Ficoll™ (Winthrop Laboratories, New York). Lymph node cultures may generally be prepared by immunizing BALB/c mice (e.g., in the rear foot pad) with promastigotes emulsified in complete Freund's adjuvant. The draining lymph nodes may be excised following immunization and T-cells may be purified in an anti-mouse Ig column to remove the B cells, followed by a passage through a Sephadex G10 column to remove the macrophages. Similarly, lymph node cells may be isolated from a human following biopsy or surgical removal of a lymph node.

The ability of a fusion polypeptide of the disclosure to induce a response in PBMC or lymph node cell cultures may be evaluated, for example, by contacting the cells with the polypeptide and measuring a suitable response. In general, the amount of polypeptide that is sufficient for the evaluation of about $2\times10^5$ cells ranges from about 10 ng to about 100 ug or 100 ng to about 50 ug, and preferably is about 1 ug, to 10 ug. The incubation of polypeptide (e.g., a fusion polypeptide) with cells is typically performed at 37° C. for about 1-3 days. Following incubation with polypeptide, the cells are assayed for an appropriate response. If the response is a proliferative response, any of a variety of techniques well known to those of ordinary skill in the art may be employed. For example, the cells may be exposed to a pulse of radioactive thymidine and the incorporation of label into cellular DNA measured. In general, a polypeptide that results in at least a three fold increase in proliferation above background (i.e., the proliferation observed for cells cultured without polypeptide) is considered to be able to induce proliferation.

Alternatively, the response to be measured may be the secretion of one or more cytokines (such as interferon-y (IFN-y), interleukin-4 (IL-4), interleukin-12 (p70 and/or p40), interleukin-2 (IL-2) and/or tumor necrosis factor-a (TNF-a)) or the change in the level of mRNA encoding one or more specific cytokines. For example, the secretion of interferon-y, interleukin-2, tumor necrosis factor-a and/or interleukin-12 is indicative of a Th1 response, which contributes to the protective effect against M. leprae. Assays for any of the above cytokines may generally be performed using methods known to those of ordinary skill in the art, such as an enzyme-linked immunosorbent assay (ELISA). Suitable antibodies for use in such assays may be obtained from a variety of sources such as Chemicon, Temucula, CA and PharMingen, San Diego, CA, and may generally be used according to the manufacturer's instructions. The level of mRNA encoding one or more specific cytokines may be evaluated by, for example, amplification by polymerase chain reaction (PCR). In general, a polypeptide that is able to induce, in a preparation of about $1-3\times10^5$ cells, the production of 30 pg/mL of IL-12, IL-4, IFN-y, TNF-a or IL-12 p40, or 10 pg/mL of IL-12 p70, is considered able to stimulate production of a cytokine.

Polynucleotide Compositions

The present disclosure also provides isolated polynucleotides, particularly those encoding the polypeptide combinations and/or fusion polypeptides of the disclosure, as well as compositions comprising such polynucleotides. As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this disclosure can include genomic sequences, extra-genomic and plasmid-encoded sequences and smaller engineered gene segments that express, or may be adapted to express, proteins, fusion polypeptides, peptides and the like. Such segments may be naturally isolated, recombinant, or modified synthetically by the hand of man.

As will be recognized by the skilled artisan, polynucleotides may be single-stranded (coding or anti sense) or double-stranded, and may be DNA (genomic, cDNA or synthetic) or RNA molecules. Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine. Additional coding or non-coding sequences may, but need not, be present within a polynucleotide of the present disclosure, and a polynucleotide may, but need not, be linked to other molecules and/or support materials.

Polynucleotides may comprise a native sequence (i.e., an endogenous sequence that encodes a M. leprae antigen or a portion thereof) or may comprise a variant, or a biological or antigenic functional equivalent of such a sequence. In particular embodiments, polynucleotides may encode for two or more antigenic/immunogenic portions, fragments, or variants derived from the M. leprae antigens described herein. In some embodiments, polynucleotides of the present disclosure comprise a sequence encoding any of the immunogenic portions described herein. In some embodiments, the polynucleotide comprises the sequence of SEQ ID NO: 1, 3, 5, 7, 9, or 11. Of course, portions of these sequences and variant sequences sharing identity to these sequences may also be employed (e.g., those having at least about any of 80%, 85%, 90%, 91%, 92%, 93%, 94%, 95%, 96%, 97%, 98%, or 99% thereto).

Polynucleotide variants may contain one or more substitutions, additions, deletions and/or insertions, as further described below, preferably such that the immunogenicity of the encoded polypeptide is not diminished, relative to the native protein. The effect on the immunogenicity of the encoded polypeptide may generally be assessed as described herein.

For example, in certain embodiments, variants of the disclosure include cysteine-modified polynucleotides in which the cysteine-encoding codons are replaced with codons encoding other amino acids not capable of forming intrachain or interchain disulfide bonds. In more specific embodiments, some or all of the replacement codons encode serine because of the spatial similarity of the serine sidechain to the cysteine sidechain in the resulting polypeptide. In another specific embodiment, some or all of the replacement codons encode alanine. Illustrative methods of replacing cysteine and other codons within a polynucleotide are well known (e.g., U.S. Pat. No. 4,816,566, the contents of which are incorporated herein by reference, and Proc Natl Acad Sci 97 (15): 8530, 2000).

The term "variants" also encompasses homologous genes of xenogenic origin.

In additional embodiments, isolated polynucleotides of the present disclosure comprise various lengths of contiguous stretches of sequence identical to or complementary to the sequence encoding *M. leprae* polypeptides, such as those sequences disclosed herein. For example, polynucleotides are provided by this disclosure that comprise at least about 15, 20, 30, 40, 50, 75, 100, 150, 200, 300, 400, 500 or 1000 or more contiguous nucleotides of two or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

The polynucleotides of the present disclosure, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed; with the total length preferably being limited by the ease of preparation and use in the intended recombinant DNA protocol.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure, for example polynucleotides that are optimized for human and/or primate codon selection. Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

*M. leprae* polynucleotides and fusions thereof may be prepared, manipulated and/or expressed using any of a variety of well established techniques known and available in the art. In particular embodiments, fusions comprise two or more polynucleotide sequences encoding *M. leprae* polypeptides.

For example, polynucleotide sequences or fragments thereof which encode polypeptides of the disclosure, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide of the present disclosure.

As will be understood by those of skill in the art, it may be advantageous in some instances to produce fusion polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present disclosure can be engineered using methods generally known in the art in order to alter fusion polypeptide encoding sequences for a variety of reasons, including but not limited to, alterations which modify the cloning, processing, expression and/or immunogenicity of the gene product.

In order to express a desired fusion polypeptide comprising two or more antigenic/immunogenic fragments or portions of *M. leprae* polypeptides, a nucleotide sequence encoding the fusion polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (2001), and Ausubel et al., Current Protocols in Molecular Biology (January 2008, updated edition).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast (such as *Saccharomyces* or *Pichia*) transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRJPT phagemid (Stratagene, La Jolla, Calif.) or PSPORTI plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional *E. coli* cloning and expression vectors such as PBLUESCRIPT (Stratagene), in which the sequence encoding the polypeptide of interest may be ligated into the vector in frame with sequences for the amino-terminal Met and the subsequent 7 residues of B-galactosidase so that a hybrid protein is produced; pIN vectors (Van Heeke & Schuster, J. Biol. Chem. 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al., Methods Enzymol. 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, EMBO J. 6:307-311 (1987)). Alternatively, plant promoters such as the small subunit of RUBISCO or heat shock promoters may be used (Coruzzi et EMBO J. 3:1671-1680 (1984); Broglie et al., Science 224:838-843 (1984); and Winter et al., Results Probl. Cell Differ. 17:85-105 (1991)). These constructs can be introduced into plant cells by direct DNA transformation or pathogen-mediated transfection. Such techniques are described in a number of generally available reviews (see, e.g., Hobbs in McGraw Hill, Yearbook of Science and Technology, pp. 191-196 (1992)).

An insect system may also be used to express a polypeptide of interest. For example, in one such system, Autographa californica nuclear polyhedrosis virus (AcNPV) is used as a vector to express foreign genes in Spodoptera frugiperda cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, S. frugiperda cells or Trichoplusia larvae in which the polypeptide of interest may be expressed (Engelhard et al., Proc. Natl. Acad. Sci. U.S.A. 91:3224-3227 (1994)).

In mammalian host cells, a number of viral-based expression systems are generally available. For example, in cases where an adenovirus is used as an expression vector, sequences encoding a polypeptide of the present disclosure may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, Proc. Natl. Acad. Sci. U.S.A. 81:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a fusion polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., Results ProbL Cell Differ. 20:125-162 (1994)).

In addition, a host cell strain may be chosen for its ability to modulate the expression of the inserted sequences or to process the expressed fusion protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a fusion polynucleotide of the present disclosure may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., Cell 11:223-232 (1977)) and adenine phosphoribosyltransferase (Lowy et al., Cell 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., Proc. Natl. Acad. Sci. U.S.A. 77:3567-70 (1980)); npt, which confers resistance to the aminoglycosides, neomycin and G-418 (Colbere-Garapin et al., J. Mol. Biol. 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, Proc. Natl. Acad. Sci. U.S.A. 85:8047-51 (1988)). The use of visible markers has gained popularity with such markers as anthocyanins, B-glucuronidase and its substrate GUS, and luciferase and its substrate luciferin, being widely used not only to identify transformants, but also to quantify the amount of transient or stable protein expression attributable to a specific vector system (Rhodes et al., Methods MoL Biol. 55:121-131 (1995)).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., Serological Methods, a Laboratory Manual (1990) and Maddox et al., J. Exp. Med. 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the disclosure may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. In addition to recombinant production methods, fusion polypeptides of the disclosure, and fragments thereof, may be produced by direct peptide synthesis using solid-phase techniques (Merrifield, J. Am. Chem. Soc. 85:2149-2154 (1963)). Protein synthesis may be performed using manual techniques or by automation. Automated synthesis may be achieved, for example, using Applied Biosystems 431 A Peptide Synthesizer (Perkin Elmer). Alternatively, various fragments, for example, immunogenic fragments from *M. leprae* polypeptides, may be chemically synthesized separately and combined using chemical methods to produce the full length molecule.

Pharmaceutical and Vaccine Compositions

In certain aspects, the polypeptides, antigens, polynucleotides, portions, variants, fusion polypeptides, etc., as described herein, are incorporated into pharmaceutical compositions or vaccines. Pharmaceutical compositions generally comprise one or more polypeptides, antigens, polynucleotides, portions, variants, fusion polypeptides, etc., as described herein, in combination with a physiologically acceptable carrier. Vaccines, also referred to as immunogenic compositions, generally comprise one or more of the polypeptides, antigens, polynucleotides, portions, variants, fusion proteins, etc., as described herein, in combination with an immunostimulant, such as an adjuvant. In particular embodiments, the compositions comprise fusion polypeptides containing *M. leprae* antigens (or portions or variants thereof) that are capable of providing protection against *M. leprae*. In some embodiments, the compositions comprise fusion polypeptides containing *M. leprae* antigens (or portions or variants thereof) that are capable of providing protection against a tuberculosis-causing *mycobacterium*.

An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., Vaccine Design (the subunit and adjuvant approach) (1995).

Any of a variety of immunostimulants may be employed in the vaccines of this disclosure. For example, an adjuvant may be included. Many adjuvants contain a substance designed to protect the antigen from rapid catabolism, such as aluminum hydroxide or mineral oil, and a stimulator of immune responses, such as lipid A (natural or synthetic), *Bordetella pertussis* or *Mycobacterium* species or *Mycobacterium*-derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (GlaxoSmithKline Beecham, Philadelphia, Pa.); CWS, TDM, LeIF, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quit A. Cytokines, such as GM-CSF or interleukin-2, -7, or -12, may also be used as adjuvants.

Certain embodiments of the present disclosure contemplate vaccine and pharmaceutical compositions that include one or more toll-like receptor agonists (TLR agonist). In more specific embodiments, for example, the compositions of the disclosure include Toll-like receptor agonists, such as TLR7 agonists and TLR7/8 agonists. In certain embodiments the TLR agonist is capable of delivering a biological signal by interacting with at least one TLR that is selected from TLR-2, TLR-3, TLR-4, TLR-5, TLR-6, TLR-7, TLR-8 and TLR-9.

Toll-like receptors (TLR) include cell surface transmembrane receptors of the innate immune system that confer early-phase recognition capability to host cells for a variety of conserved microbial molecular structures such as may be present in or on a large number of infectious pathogens, (e.g., Armant et al., 2002 Genome Biol. 3(8): reviews 3011.1-3011.6; Fearon et al., 1996 Science 272:50; Medzhitov et al., 1997 Curr. Opin. Immunol. 9:4; Luster 2002 Curr. Opin. Immunol. 14:129; Lien et al. 2003 Nat. Immunol. 4:1162; Medzhitov, 2001 Nat. Rev. Immunol. 1:135; Takeda et al., 2003 Ann Rev Immunol. 21:335; Takeda et al. 2005 Inf. Immunol. 17:1; Kaisho et al., 2004 Microbes Infect. 6:1388; Datta et al., 2003 J. Immunol. 170:4102).

Induction of TLR-mediated signal transduction to potentiate the initiation of immune responses via the innate immune system may be effected by TLR agonists, which engage cell surface TLR or cytoplasmic TLR. For example, lipopolysaccharide (LPS) may be a TLR agonist through TLR2 or TLR4 (Tsan et al., 2004 J. Leuk. Biol. 76:514; Tsan et al., 2004 Am. J. Physiol. Cell Phsiol. 286:C739; Lin et al., 2005 Shock 24:206); poly(inosine-cytidine) (polyI:C) may be a TLR agonist through TLR3 (Salem et al., 2006 Vaccine 24:5119); CpG sequences (oligodeoxynucleotides containing unmethylated cytosine-guanosine or "CpG" dinucleotide motifs, e.g., CpG 7909, Cooper et al., 2005 AIDS 19:1473; CpG 10101 Bayes et al. Methods Find Exp Clin Pharmacol 27:193; Vollmer et al. Expert Opinion on Biological Therapy 5:673; Vollmer et al., 2004 Antimicrob. Agents Chemother. 48:2314; Deng et al., 2004 J. Immunol. 173:5148) may be TLR agonists through TLR9 (Andaloussi et a., 2006 Glia 54:526; Chen et al., 2006 J. Immunol. 177:2373); peptidoglycans may be TLR2 and/or TLR6 agonists (Soboll et al., 2006 Biol. Reprod. 75:131; Nakao et al., 2005 J. Immunol. 174:1566); 3M003 (4-amino-2-(ethoxymethyl)-a,a-dimethyl-617,8,9-tetrahydro-1H-imidazo[4,5] quinoline-1-ethanol hydrate, Mol. Wt. 318 Da from 3M Pharmaceuticals, St. Paul, MN, which is also a source of the related compounds 3M001 and 3M002; Gorden et al., 2005 J. Immunol. 174: 1259) may be a TLR7 agonist (Johansen 2005 Clin. Exp. Allerg. 35:1591) and/or a TLR8 agonist (Johansen 2005); flagellin may be a TLR5 agonist (Feuillet et al., 2006 Proc. Nat. Acad. Sci. USA 103: 12487); and hepatitis C antigens may act as TLR agonists through TLR7 and/or TLR9 (Lee et al., 2006 Proc. Nat. Acad. Sci. USA 103:1828; Horsmans et al., 2005 Hepatol. 42:724). Other TLR agonists are known (e.g., Schirmbeck et al., 2003 J. Immunol. 171:5198) and may be used according to certain of the presently described embodiments.

For example, and by way of background (see, e.g., U.S. Pat. No. 6,544,518) immunostimulatory oligonucleotides containing unmethylated CpG dinucleotides ("CpG") are known as being adjuvants when administered by both systemic and mucosal routes (WO 96/02555, EP 468520, Davis et al., J. Immunol, 1998. 160(2): 870-876; McCluskie and Davis, J. Immunol., 1998, 161(9):4463-6). CpG is an abbreviation for cytosine-guanosine dinucleotide motifs present in DNA. The central role of the CG motif in immunostimulation was elucidated by Krieg, Nature 374, p546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the dinucleotide CG motif is not methylated, but other unmethylated CpG sequences are known to be immunostimulatory and may be used in certain embodiments of the present disclosure. CpG when formulated into vaccines, may be administered in free solution together with free antigen (WO 96/02555; McCluskie and Davis, supra) or covalently conjugated to an antigen (PCT Publication No. WO 98/16247), or formulated with a carrier such as aluminium hydroxide (e.g., Davis et al. supra, Brazolot-Millan et al., Proc.NatLAcad.Sci., USA, 1998, 95(26), 15553-8).

Other illustrative oligonucleotides for use in compositions of the present disclosure will often contain two or more dinucleotide CpG motifs separated by at least three, more preferably at least six or more nucleotides. The oligonucleotides of the present disclosure are typically deoxynucleotides. In one embodiment the internucleotide in the oligonucleotide is phosphorodithioate, or more preferably a phosphorothioate bond, although phosphodiester and other internucleotide bonds are within the scope of the disclosure including oligonucleotides with mixed internucleotide linkages. Methods for producing phosphorothioate oligonucleotides or phosphorodithioate are described in U.S. Pat. Nos. 5,666,153, 5,278,302 and WO95/26204.

Other examples of oligonucleotides have sequences that are disclosed in the following publications; for certain herein disclosed embodiments the sequences preferably contain phosphorothioate modified internucleotide linkages:

CPG 7909: Cooper et al., "CPG 7909 adjuvant improves hepatitis B virus vaccine seroprotection in antiretroviral-treated HIV-infected adults." AIDS, 2005 Sep. 23; 19(14): 1473-9.

CpG 10101: Bayes et al., "Gateways to clinical trials." Methods Find. Exp. Clin. Pharmacol. 2005 April; 27(3): 193-219.

Vollmer J., "Progress in drug development of immunostimula-tory CpG oligodeoxynucleotide ligands for TLR9." Expert Opinion on Biological Therapy. 2005 May; 5(5): 673-682.

Alternative CpG oligonucleotides may comprise variants of the preferred sequences described in the above-cited publications that differ in that they have inconsequential nucleotide sequence substitutions, insertions, deletions and/or additions thereto. The CpG oligonucleotides utilized in certain embodiments of the present disclosure may be synthesized by any method known in the art (e.g., EP 468520). Conveniently, such oligonucleotides may be synthesized utilising an automated synthesizer. The oligonucleotides are typically deoxynucleotides. In a preferred embodiment the internucleotide bond in the oligonucleotide is phosphorodithioate, or more preferably phosphorothioate bond, although phosphodiesters are also within the scope of the presently contemplated embodiments. Oligonucleotides comprising different internucleotide linkages are also contemplated, e.g., mixed phosphorothioate phophodiesters. Other internucleotide bonds which stabilize the oligonucleotide may also be used.

In certain more specific embodiments the TLR agonist is selected from lipopolysaccharide, peptidoglycan, polyI: C, CpG, 3M003, flagellin, M. leprae homolog of eukaryotic ribosomal elongation and initiation factor 4a (LeIF) and at least one hepatitis C antigen.

Still other illustrative adjuvants include imiquimod, gardiquimod and resiquimod (all available from Invivogen), and related compounds, which are known to act as TLR7/8 agonists. A compendium of adjuvants that may be useful in vaccines is provided by Vogel et al., Pharm Biotechnol 6:141 (1995), which is herein incorporated by reference.

Compositions of the disclosure may also employ adjuvant systems designed to induce an immune response predominantly of the Th1 type. High levels of Th1-type cytokines (e.g., IFN-y, TNF-a, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly of the Th1-type, the level of Th1-type cytokines will increase to a greater extent than the level of Th2-type cytokines. The levels of these cytokines may be readily assessed using standard assays. For a review of the families of cytokines, see Mossman & Coffman, Ann. Rev. Immunol. 7:145-173 (1989).

Certain adjuvants for use in eliciting a predominantly Th1-type response include, for example, a combination of monophosphoryl lipid A, preferably 3-de-O-acylated monophosphoryl lipid A (3D-MPL™), together with an aluminum salt (U.S. Pat. Nos. 4,436,727; 4,877,611; 4,866,034; and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., Science 273:352 (1996). Another illustrative adjuvant comprises a saponin, such as Quil A, or derivatives thereof, including QS21 and QS7 (Aquila Biopharmaceuticals Inc., Framingham, Mass.); Escin; Digitonin; or Gypsophila or Chenopodium quinoa saponins. Other illustrative formulations include more than one saponin in the adjuvant combinations of the present disclosure, for example combinations of at least two of the following group comprising QS21, QS7, Quil A, 0-escin, or digitonin.

In a particular embodiment, the adjuvant system includes the combination of a monophosphoryl lipid A and a saponin derivative, such as the combination of QS21 and 3D-MPL™ adjuvant, as described in WO 94/00153, or a less reactogenic composition where the QS21 is quenched with cholesterol, as described in WO 96/33739. Other formulations comprise an oil-in-water emulsion and tocopherol. Another adjuvant formulation employing QS21, 3D-MPL™ adjuvant and tocopherol in an oil-in-water emulsion is described in WO 95/17210.

In certain preferred embodiments, the adjuvant used in the present disclosure is a glucopyranosyl lipid A (GLA) adjuvant, as described in U.S. Patent Application Publication No. 20080131466, the disclosure of which is incorporated herein by reference in its entirety. In one embodiment, the GLA adjuvant used in the context of the present disclosure has the following structure:

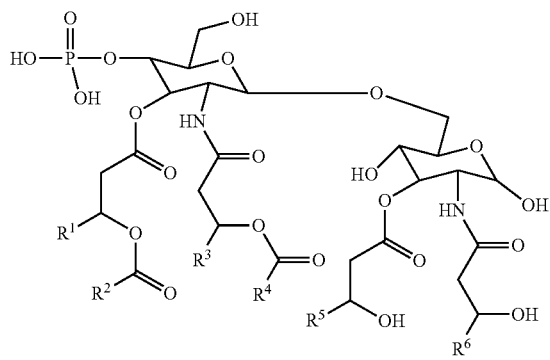

where: $R^1$, $R^3$, $R^5$ and $R^6$ are $C_{11}$-$C_{20}$ alkyl, and $R^2$ and $R^4$ are $C_9$-$C_{20}$ alkyl.

In a more specific embodiment, the GLA has the formula set forth above wherein $R^1$, $R^3$, $R^5$ and $R^6$ are $C_{11-14}$ alkyl, and $R^2$ and $R^4$ are $C_{12-15}$ alkyl.

In a more specific embodiment, the GLA has the formula set forth above wherein $R^1$, $R^3$, $R^5$ and $R^6$ are $C_{11}$ alkyl; and $R^2$ and $R^4$ are C13 alkyl.

In a more specific embodiment, the GLA has the formula set forth above wherein R', $R^3$, $R^5$ and $R^6$ are $C_{11}$ alkyl; and $R^2$ and $R^4$ are $C_9$ alkyl.

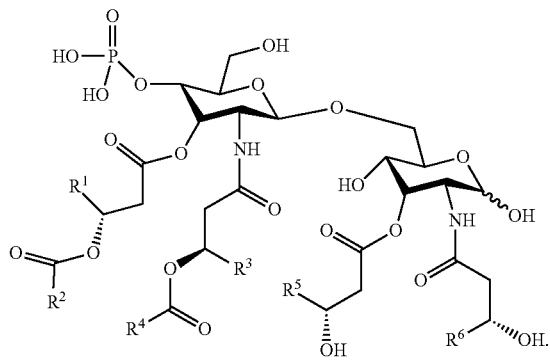

In certain embodiments, the adjuvant is a GLA adjuvant (e.g., synthetic) having the following structure:

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are C9 alkyl.

In certain embodiments, the adjuvant is a synthetic GLA adjuvant having the following structure:

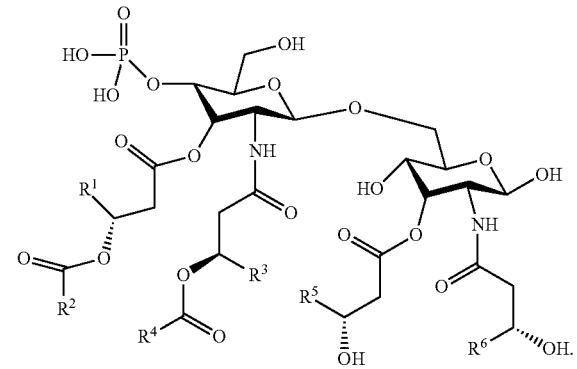

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are C9 alkyl.

In certain embodiments, the adjuvant is a synthetic GLA adjuvant having the following structure:

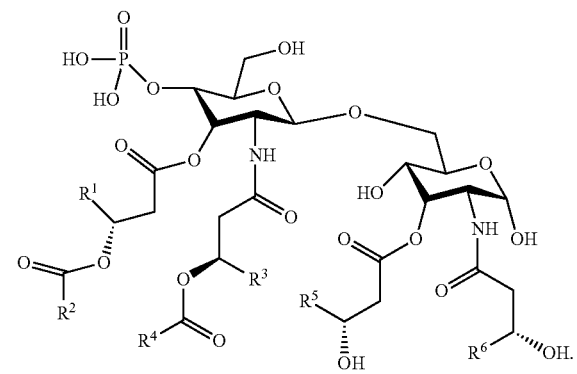

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are C9 alkyl.

In certain embodiments, the adjuvant is a synthetic GLA adjuvant having the following structure:

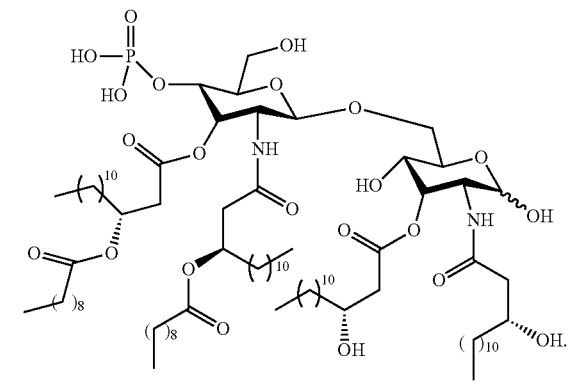

In certain embodiments, the adjuvant is a synthetic GLA adjuvant having the following structure:

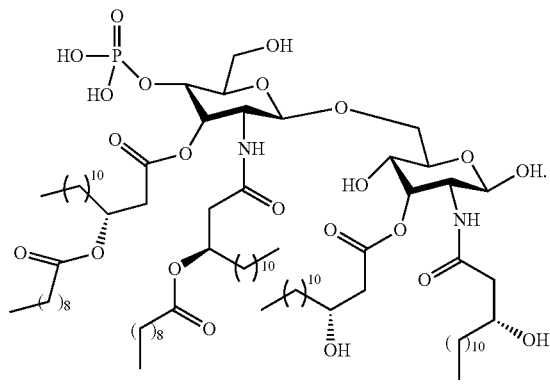

In certain embodiments, the adjuvant is a synthetic GLA adjuvant having the following structure:

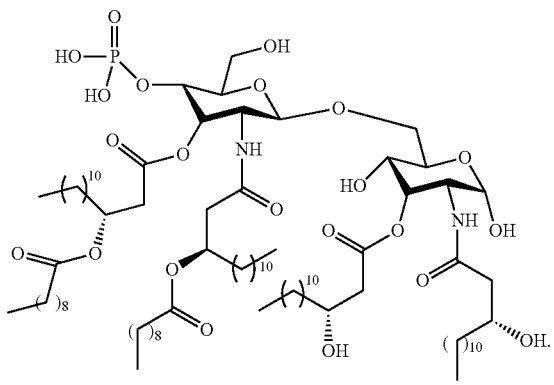

In certain embodiments, the adjuvant is GLA-SE having the following structure:

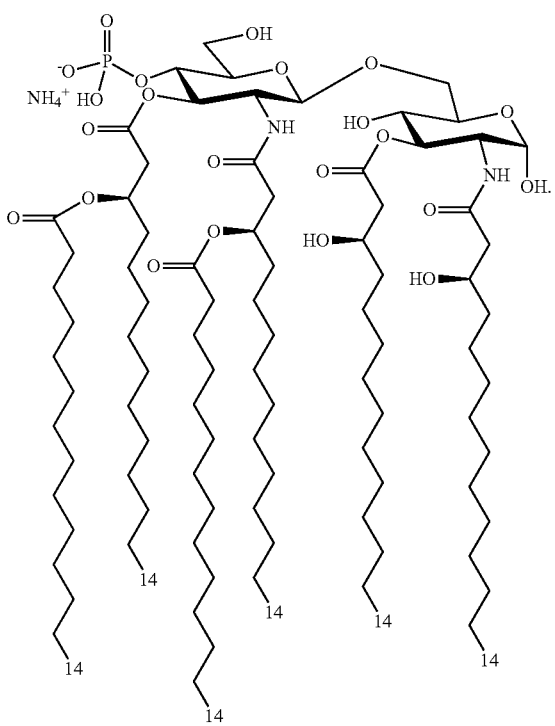

In certain embodiments, the adjuvant is GLA-SE having the following structure:

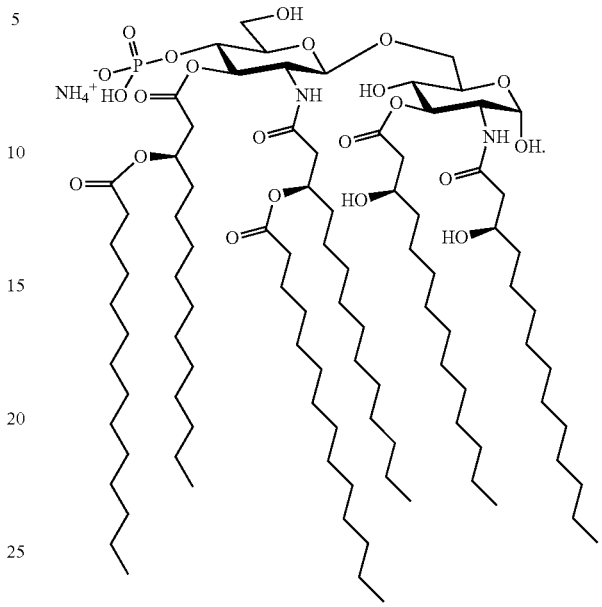

The skilled artisan will understand that, in any of the embodiments described herein, the GLA adjuvant may be in a salt form, e.g., an ammonium salt.

GLA-SE refers to a stable oil-in-water emulsion comprising GLA formulated in squalene oil and other excipients including, for example, dimyristoyl phosphatidyl choline (DPMC). In some preferred embodiments, 20 ug/ml GLA is formulated in 4% squalene oil. Methods of making GLA-SE are known in the art, see for example, Misquith et al., Colloids and Surfaces B: Biointerfaces 113(2014) 312-319; Fox et al., Vaccine 31(2013) 1633-1640, Van Hoeven et al., Nature Scientific Reports 7:46426.

Another enhanced adjuvant system involves the combination of a CpG-containing oligonucleotide and a saponin derivative as disclosed in WO 00/09159.

Other illustrative adjuvants include Montanide ISA 720 (Seppic, France), SAF (Chiron, Calif, United States), ISCOMS (CSL), MF-59 (Chiron), the SBAS series of adjuvants (e.g., SBAS-2, AS2', AS2," SBAS-4, or SBAS6, available from SmithKline Beecham, Rixensart, Belgium), Detox, RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

The vaccine and pharmaceutical compositions of the disclosure may be formulated using any of a variety of well known procedures. In certain embodiments, the vaccine or pharmaceutical compositions are prepared as stable emulsions (e.g., oil-in-water emulsions) or as aqueous solutions.

Compositions of the disclosure may also, or alternatively, comprise T cells specific for fusion polypeptide comprising immunogenic/antigenic portions or fragments of M. leprae antigens or variants thereof, described herein. Such cells may generally be prepared in vitro or ex vivo, using standard procedures. For example, T cells may be isolated from bone marrow, peripheral blood, or a fraction of bone marrow or peripheral blood of a patient. Alternatively, T cells may be derived from related or unrelated humans, non-human mammals, cell lines or cultures.

T cells may be stimulated with a fusion polypeptide comprising M. leprae polypeptides or immunogenic portions or variants thereof, polynucleotide encoding such a fusion polypeptide, and/or an antigen presenting cell (APC) that expresses such a fusion polypeptide. Such stimulation is performed under conditions and for a time sufficient to permit the generation of T cells that are specific for the polypeptide. In certain embodiments, the polypeptide or polynucleotide is present within a delivery vehicle, such as a microsphere, to facilitate the generation of specific T cells.

T cells are considered to be specific for a fusion polypeptide of the disclosure if the T cells specifically proliferate, secrete cytokines or kill target cells coated with the fusion polypeptide or expressing a gene encoding the fusion polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065-1070 (1994)).

Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a polypeptide of the disclosure (100 ng/ml-100 1.1 g/ml, preferably 200 ng/ml-25 1.1 g/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-y) is indicative of T cell activation (see Coligan et al., Current Protocols in Immunology, vol. 1 (1998)). T cells that have been activated in response to a polypeptide, polynucleotide or polypeptide-expressing APC may be CD4+ and/or CD8+. Protein-specific T cells may be expanded using standard techniques. Within preferred embodiments, the T cells are derived from a patient, a related donor or an unrelated donor, and are administered to the patient following stimulation and expansion.

In the compositions of the disclosure, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intradermal, subcutaneous and intramuscular administration and formulation.

In certain applications, the compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the compositions disclosed herein parenterally, intravenously, intramuscularly, or even intraperitoneally as described, for example, in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington's Pharmaceutical Sciences, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologies standards.

Sterile injectable solutions are prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxy groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective for treatment of leprosy. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known to one of ordinary skill in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood to one of ordinary skill in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the compositions of the present disclosure may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of compositions comprising a fusion polypeptide as describe herein into suitable host cells. In particular, the compositions of the present disclosure may be formulated for delivery either encapsulated in a lipid particle, a liposome, a vesicle, a nanosphere, a nanoparticle or the like. The formulation and use of such delivery vehicles can be carried out using known and conventional techniques.

A pharmaceutical or immunogenic composition may, alternatively, contain an immunostimulant and a nucleic acid molecule, e.g., a DNA or RNA molecule encoding one or more of the polypeptides or fusion polypeptides as described above, such that a desired polypeptide is generated in situ. In such compositions, the DNA encoding the fusion protein may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface. In a particular embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., Science 259:1745-1749 (1993) and reviewed by Cohen, Science 259: 1691-1692 (1993). The uptake of naked DNA may be increased by coating the DNA onto biodegradable beads, which are efficiently transported into the cells.

The pharmaceutical compositions and vaccines of the disclosure may be used, in certain embodiments, to induce protective immunity against *M. leprae* in a patient, such as a human or an armadillo, to prevent leprosy or diminish its severity. The compositions and vaccines may also be used to stimulate an immune response, which may be cellular and/or humoral, in a patient, for treating an individual already infected. In one embodiment, for *M. Leprae*-infected patients, the immune responses generated include a preferential Th1 immune response (i.e., a response characterized by the production of the cytokines interleukin-1, interleukin-2, interleukin-12 and/or interferon-y, as well as tumor necrosis factor-a). In another embodiment, for uninfected patients, the immune response involves production of interleukin-12 and/or interleukin-2, or the stimulation of gamma delta T-cells. In either category of patient, the response stimulated may include IL-12 production. Such responses may also be elicited in biological samples of PBMC or components thereof derived from *M. leprae*-infected or uninfected individuals. As noted above, assays for any of the above cytokines, as well as other known cytokines, may generally be performed using methods known to those of ordinary skill in the art, such as an enzyme-linked immunosorbent assay (ELISA).

Appropriate doses and methods of fusion polypeptide administration for these purposes can be readily determined by a skilled artisan using available knowledge in the art and/or routine techniques. Routes and frequency of administration, as well as dosage, for the above aspects of the present disclosure may vary from individual to individual and may parallel those currently being used in immunization against other infections, including protozoan, viral and bacterial infections. For example, in one embodiment, between 1 and 12 doses of composition having a fusion polypeptide, which comprises *M. leprae* polypeptides or immunogenic/antigenic portions, fragments or variants thereof, are administered over a 1 year period. Booster vaccinations may be given periodically thereafter as needed or desired. Of course, alternate protocols may be appropriate for individual patients. In a particular embodiment, a suitable dose is an amount of fusion polypeptide or DNA encoding such a peptide that, when administered as described above, is capable of eliciting an immune response in an immunized patient sufficient to protect the patient from leprosy caused by *M. leprae*. In general, the amount of fusion polypeptide present in a dose (or produced in situ by the DNA in a dose) ranges from about 100 ng to about 1 mg per kg of host, typically from about 101. 1 g to about 100 ug. Suitable dose sizes will vary with the size of the patient, but will typically range from about 0.1 mL to about 5 mL. In some aspects, from 1 ug to about 20 ug per dose or from about 1 ug to about 10 ug per dose of a composition of the present invention is administered to a subject in the methods described herein. If so desired, the composition can be, for example, in lyophilized form. In some aspects, the composition is administered in combination with an immunostimulant. The immunostimulant can be, for example, any of the immunostimulants described herein. In some aspects, the immunostimulant is GLA having any one of the structures described herein and is optionally formulated in an oil-in-water emulsion. In some aspects, the GLA is administered at a dose of from 2 ug to 20 ug per dose, or from about 1 ug to about 10 ug per dose or at about 5 ug per dose. The skilled artisan will appreciate that alternative dosage amounts are contemplated herein.

Methods of Stimulating an Immune Response

In another aspect, this disclosure provides methods for stimulating an immune response against *M. leprae* in a mammal including the step of administering to a mammal in need thereof a composition of the present disclosure. In some embodiments, the methods further include a step of administering to the mammal *M. bovis* BCG vaccine. In other embodiments *M. bovis* BCG vaccine was previously administered to the mammal. The method may involve stimulating an immune response in various populations of mammals, including, where the mammal has not been exposed to *M. leprae*, where the mammal has been exposed to *M. leprae*, where the mammal is a human healthy household contact of a human identified as being infected with *M. leprae*, where the mammal has been infected by *M. leprae*, and where the mammal exhibits signs or symptoms of infection by *M. leprae*. The compositions of the present disclosure can be administered, for example, prophylactically, post-exposure but prior to clinical symptoms, or post-exposure and after exhibition of clinical symptoms. In some aspects, it will be unknown whether or not the mammal to be treated has been exposed to *M. leprae* but the mammal will have been in a leprosy endemic region or in contact with a mammal having active leprosy.

In another aspect, the disclosure provides methods for stimulating an immune response against a tuberculosis-causing *mycobacterium* in a mammal comprising administering to a mammal in need thereof a composition of the disclosure.

Methods of Treatment

In another aspect, the disclosure provides methods for treating an *M. leprae* infection in a mammal, including the step of administering to a mammal having an *M. leprae* infection a composition of the disclosure. The method may include multiple subsequent administrations of the composition.

Identifying mammals having an *M. leprae* infection may be carried with methods known in the art. The World Health Organization (WHO) has established diagnostic criteria as the presence of one or more of the following key signs: appearance of hypopigmented or reddish lesion with hypoesthesia, presence of acid fast bacilli in lymph node smears and compatible skin lesion histopathology. Once diagnosed, leprosy is treatable and patients are operationally defined into one of two categories, paucibacillary (PB) or multibacillary (MB) for treatment purposes. The Ridley-Jopling scale characterizes five forms of leprosy through the use of clinical, histopathological, and immunological methods: lepromatous leprosy (LL), borderline lepromatous (BL), mid-borderline (BB), borderline tuberculoid (BT), and tuberculoid leprosy (TT). {Ridley D S et al., *Int J Lepr Other Mycobact Dis* 1966; 34(3): 255-73; Scollard D M Int. *J Lepr Other Mycobact Dis* 2004; 72(2): 166-8.} A pure neural leprosy presentation, which is PB, also exists. PB leprosy patients, encompassing TT and a number of BT forms, are characterized as having one or few skin lesions and granulomatous dermatopathology with a low or absent bacterial index (BI). At the extreme PB pole, TT patients demonstrate a specific cell-mediated immunity against *M. leprae* and have an absent, or low, BI. Control of bacterial growth by PB patients indicates that these individuals mount a strong, but not necessarily curative, immune response against *M. leprae*.

In some embodiments, the methods further include a step of administering to the mammal one or more chemotherapeutic agents. A "chemotherapeutic", "chemotherapeutic agents" or "chemotherapy regime" is a drug or combination of drugs used to treat or in the treatment thereof of patients infected or exposed to *M. leprae* and includes, but is not limited to, amikacin, aminosalicylic acid, capreomycin, clofazimine, cycloserine, dapsone, ethambutol, ethionamide, gatifloxacin, isoniazid (INH), kanamycin, linezolid, minocycline, pyrazinamide, rifamycins (i.e., rifampin, rifampicin, rifapentine and rifabutin), streptomycin, ofloxacin, ciprofloxacin, clarithromycin, azithromycin, PA824, and fluoroquinolones and other derivatives analogs or biosimilars in the art.

In some embodiments, the mammal is first administered one or more chemotherapeutic agents over a period of time and subsequently administered the composition. In other embodiments, the mammal is first administered the composition and subsequently administered one or more chemotherapeutic agents over a period of time. In other embodiments, administration of the one or more chemotherapeutic agents and the composition is concurrent.

In some embodiments, the method includes a step of administering to the mammal *M. bovis* BCG vaccine. In other embodiments, *M. bovis* BCG vaccine was previously administered to the mammal.

The method may be practiced on various groups of mammals. In some embodiments, the mammal does not exhibit signs or symptoms of infection by *M. leprae*. In some embodiments, the mammal has indeterminate or tuberculoid presentation. In some embodiments, the mammal has paucibacillary leprosy. In some embodiments, the mammal has multibacillary leprosy. In some embodiments, the mammal has lepromatous leprosy. In some embodiments, the mammal has borderline lepromatous leprosy. In some embodiments, the mammal has mid-borderline leprosy. In some embodiments, the mammal has borderline tuberculoid leprosy. In some embodiments, the mammal has tuberculoid leprosy. In some embodiments, the mammal is infected with a multidrug resistant *M. leprae*. In some embodiments, the mammal is a human.

In another aspect, a method for reducing the time course of chemotherapy against an *M. leprae* infection is provided.

The time course of chemotherapy is shortened, for example, to no more than about 3 months, about 5 months, or about 7 months.

A "chemotherapeutic", "chemotherapeutic agents" or "chemotherapy regime" is a drug or combination of drugs used to treat or in the treatment thereof of patients infected or exposed to *M. leprae* and includes, but is not limited to, amikacin, aminosalicylic acid, capreomycin, clofazimine, cycloserine, dapsone, ethambutol, ethionamide, gatifloxacin, isoniazid (INH), kanamycin, linezolid, minocycline, pyrazinamide, rifamycins (i.e., rifampin, rifampicin, rifapentine and rifabutin), streptomycin, ofloxacin, ciprofloxacin, clarithromycin, azithromycin, PA824, and fluoroquinolones and other derivatives analogs or biosimilars in the art.

In another aspect, the disclosure provides methods for preventing an *M. leprae* infection in a mammal, or preventing onset of clinical symptoms in a mammal that has been exposed to *M. leprae* or has been diagnosed with *M. leprae* but does not yet exhibit symptoms thereof, including the step of administering to a mammal having an *M. leprae* infection a composition of the disclosure. The method may include multiple subsequent administrations of the composition.

It will also be understood that the methods of treatment of the present disclosure may include the administration of the compositions of the disclosure either alone or in conjunction with other agents and, as such, the therapeutic vaccine may be one of a plurality of treatment components as part of a broader therapeutic treatment regime. Accordingly, the methods of the present disclosure advantageously improve the efficacy of a chemotherapy treatment regime for the treatment of *M. leprae* infection.

In another aspect, the present disclosure provides kits for treatment of an *M. leprae* infection including a composition of the disclosure.

Diagnostic Compositions, Methods and Kits

In another aspect, this disclosure provides compounds and methods for detecting leprosy in individuals and in blood supplies. In particular embodiments, the individual is a mammal. In more particular embodiments, the mammal is a human or armadillo.

For example, the fusion polypeptides, polypeptides, and antigens of the present disclosure can be used as effective diagnostic reagents for detecting and/or monitoring *M. leprae* infection in a patient. For example, the compositions, fusion polypeptides, and polynucleotides of the disclosure may be used in in vitro and in vivo assays for detecting humoral antibodies or cell-mediated immunity against *M. leprae* for diagnosis of infection, monitoring of disease progression or test-of-cure evaluation. In particular embodiments, the fusion polypeptides and polynucleotides are useful diagnostic reagents for serodiagnosis and whole blood assay in patients having leprosy or in individuals exposed to *M. leprae*.

In one aspect, the diagnostic methods and kits preferably employ a composition or fusion polypeptide as described herein, repeats of polypeptide fragments, or multimeric polypeptide fragments, including antigenic/immunogenic fragments. In another more specific aspect, fusion polypeptides of the present disclosure may comprise two or more *M. leprae* antigen fragments. In a more particular embodiment, an illustrative fusion polypeptide comprises the amino acid sequence set forth in SEQ ID NO: 12. In another embodiment, the diagnostic methods and kits preferably employ a fusion polypeptide comprising at least 1, at least 2, at least 3, or at least 4 immunogenic/antigenic portions or fragments of *M. leprae* polypeptides, variants or the like, optionally in combination with one or more other *M. leprae* antigens or non-*M. leprae* sequences, as described herein or obtainable in the art.

The antigens or polypeptides may be used in essentially any assay format desired, e.g., as individual antigens assayed separately, as multiple antigens assays simultaneously (e.g., a fusion polypeptide), as antigens immobilized on a solid support such as an array, or the like.

In one embodiment, there are provided diagnostic kits for detecting *M. leprae* infection in a biological sample, comprising (a) a polypeptide or a fusion polypeptide described herein or variants thereof as described herein, and (b) a detection reagent.

In another embodiment, there are provided diagnostic kits for detecting *M. leprae* infection in a biological sample, comprising (a) antibodies or antigen binding fragments thereof that are specific for a polypeptide or a fusion polypeptides described herein or variants thereof as described herein, and (b) a detection reagent.

In another embodiment, methods are provided for detecting the presence of *M. leprae* infection in a biological sample, comprising (a) contacting a biological sample with a polypeptide or a fusion polypeptide described herein or variants thereof described herein; and (b) detecting in the biological sample the presence of antibodies that bind to the fusion polypeptide.

In another embodiment, methods are provided for detecting the presence of *M. leprae* infection in a biological sample, comprising (a) contacting a biological sample with at least 2 monoclonal antibodies that bind to a polypeptide or a polypeptide described herein or variants thereof described herein; and (b) detecting in the biological sample the presence of *M. leprae* proteins that bind to the monoclonal antibody.

One of ordinary skill in the art would recognize that the methods and kits described herein may be used to detect all types of leprosy, depending on the particular combination of immunogenic portions of *M. leprae* antigens present in the fusion polypeptide.

There are a variety of assay formats known to those of ordinary skill in the art for using a fusion polypeptide to detect antibodies in a sample. See, e.g., Harlow and Lane, Antibodies. A Laboratory Manual, Cold Spring Harbor Laboratory Press, 1988, which is incorporated herein by reference. In one embodiment, the assay involves the use of fusion polypeptide immobilized on a solid support to bind to and remove the antibody from the sample. The bound antibody may then be detected using a detection reagent that binds to the antibody/peptide complex and contains a detectable reporter group. Suitable detection reagents are well known and include, for example, antibodies that bind to the antibody/polypeptide complex and free polypeptide labeled with a reporter group (e.g., in a semi-competitive assay). Suitable reporter groups are also well known and include, for example, fluorescent labels, enzyme labels, radioisotopes, chemiluminescent labels, electrochemiluminescent labels, bioluminescent labels, polymers, polymer particles, metal particles, haptens, and dyes. Alternatively, a competitive assay may be utilized, in which an antibody that binds to a fusion polypeptide of the present disclosure labeled with a reporter group and allowed to bind to the immobilized fusion polypeptide after incubation of the fusion polypeptide with the sample. The extent to which components of the sample inhibit the binding of the labeled antibody to the fusion polypeptide is indicative of the reactivity of the sample with the immobilized fusion polypeptide.

The solid support may be any material known to those of ordinary skill in the art to which the fusion polypeptide may be attached. For example, the support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The fusion polypeptide may be bound to the solid support using a variety of techniques known to those in the art, which are amply described in the patent and scientific literature. In the context of the present disclosure, the term "bound" refers to both non-covalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of fusion polypeptide ranging from about 10 ng to about 1 pg, and preferably about 100 ng, is sufficient to bind an adequate amount of antigen. Nitrocellulose will bind approximately 100 pg of protein per 3 cm.

Covalent attachment of fusion polypeptide to a solid support may generally be achieved by first reacting the support with a bifunctional reagent that will react with both the support and a functional group, such as a hydroxyl or amino group, on the fusion polypeptide. For example, the fusion polypeptide may be bound to a support having an appropriate polymer coating using benzoquinone or by condensation of an aldehyde group on the support with an amine and an active hydrogen on the polypeptide (see, e.g., Pierce Immunotechnology Catalog and Handbook (1991) at A12-A13).

In certain embodiments, the assay is an enzyme linked immunosorbent assay (ELISA). This assay may be performed by first contacting a fusion polypeptide of the present disclosure that has been immobilized on a solid support, commonly the well of a microtiter plate, with the sample, such that antibodies to the *M. leprae* antigens of the fusion polypeptide within the sample are allowed to bind to the immobilized fusion polypeptide. Unbound sample is then removed from the immobilized fusion polypeptide and a detection reagent capable of binding to the immobilized antibody-polypeptide complex is added. The amount of detection reagent that remains bound to the solid support is then determined using a method appropriate for the specific detection reagent.

Once the fusion polypeptide is immobilized on the support, the remaining protein binding sites on the support are typically blocked. Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody (if present in the sample) is allowed to bind to the antigen. The sample may be diluted with a suitable diluent, such as phosphate-buffered saline (PBS) prior to incubation. In general, an appropriate contact time (i.e., incubation time) is that period of time that is sufficient to permit detection of the presence of antibody within a *M. leprae*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups, colloidal gold and biotin. The conjugation of binding agent to reporter group may be achieved using standard methods known to those of ordinary skill in the art. Common binding agents may also be purchased conjugated to a variety of reporter groups from many sources (e.g., Zymed Laboratories, San Francisco, Calif, and Pierce, Rockford, Ill.).

The detection reagent is then incubated with the immobilized antibody polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-*M. leprae* antibodies in the sample, the signal detected from the reporter group that remains bound to the solid support is generally compared to a signal that corresponds to a predetermined cut-off value. In one embodiment, the cut-off value is preferably the average mean signal obtained when the immobilized polypeptide is incubated with samples from an uninfected patient. In general, a sample generating a signal that is three standard deviations above the predetermined cut-off value is considered positive (i.e., reactive with the polypeptide). In an alternate embodiment, the cut-off value is determined using a Receiver Operator Curve, according to the method of Sackett et al., Clinical Epidemiology: A Basic Science for Clinical Medicine, p. 106-7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper lefthand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate.

In other embodiments, an assay is performed in a flow-through assay format, wherein the antigen is immobilized on a membrane such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above.

In other embodiments, an assay if performed in a strip test format, also known as a lateral flow format. Here, one end of the membrane to which polypeptide is bound is immersed in a solution containing the sample. The sample migrates along the membrane through a region containing detection reagent and to the area of immobilized fusion polypeptide. Concentration of detection reagent at the fusion polypeptide indicates the presence of *M. leprae* antibodies in the sample. Typically, the concentration of detection reagent at that site generates a pattern, such as a line, that can be read visually. The absence of such a pattern indicates a negative result. In general, the amount of fusion polypeptide immobilized on the membrane is selected to generate a visually discernible pattern when the biological sample contains a level of antibodies that would be sufficient to generate a positive signal in an ELISA, as discussed above. Preferably, the amount of fusion polypeptide immobilized on the membrane ranges from about 25 ng to about 1 fag, and more preferably from about 50 ng to about 500 ng. Such tests can typically be performed with a very small amount (e.g., one drop) of patient serum or blood. Lateral flow tests can operate as either competitive or sandwich assays.

In still other embodiments, a fusion polypeptide of the disclosure is adapted for use in a dual path platform (DPP) assay. Such assays are described, for example, in U.S. Pat. No. 7,189,522, the contents of which are incorporated herein by reference.

Of course, numerous other assay protocols exist that are suitable for use with the fusion polypeptides of the present disclosure. It will be understood that the above descriptions are intended to be exemplary only.

The assays discussed above may be used, in certain aspects of the disclosure, to specifically detect visceral leprosy. In this aspect, antibodies in the sample may be detected using a fusion polypeptide of the present disclosure, e.g., comprising an amino acid sequence of antigenic/immunogenic fragments or epitopes of *M. leprae* antigens. Preferably, the *M. leprae* antigens are immobilized by adsorption to a solid support such as a well of a microtiter plate or a membrane, as described above, in roughly similar amounts such that the total amount of fusion polypeptide in contact with the support ranges from about 10 ng to about 100 pg. The remainder of the steps in the assay may generally be performed as described above. It will be readily apparent to those of ordinary skill in the art that, by combining polypeptides described herein with other polypeptides that can detect cutaneous and mucosal leprosy, the polypeptides disclosed herein may be used in methods that detect all types of leprosy.

In another aspect of this disclosure, immobilized fusion polypeptides may be used to purify antibodies that bind thereto. Such antibodies may be prepared by any of a variety of techniques known to those of ordinary skill in the art. See, e.g., Harlow and Land, Antibodies. A Laboratory Manual, Cold Spring Harbor Laboratory Press, 1988. In one such technique, an immunogen comprising a fusion polypeptide of the present disclosure is initially injected into any of a wide variety of mammals (e.g., mice, rats, rabbits, sheep and goats). In this step, the polypeptide may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic fusion polypeptide of interest may be prepared, for example, using the technique of Kohler and Milstein, Eur. J. Immunol. 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In this process, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. One or more polypeptides may be used in the purification process in, for example, an affinity chromatography step.

Monospecific antibodies that bind to a fusion polypeptide comprising two or more immunogenic portions of *M. leprae* antigens may be used, for example, to detect *M. leprae* infection in a biological sample using one of a variety of immunoassays, which may be direct or competitive. Briefly, in one direct assay format, a monospecific antibody may be immobilized on a solid support (as described above) and contacted with the sample to be tested. After removal of the unbound sample, a second monospecific antibody, which has been labeled with a reporter group, may be added and used to detect bound antigen. In an exemplary competitive assay, the sample may be combined with the monoclonal or polyclonal antibody, which has been labeled with a suitable reporter group. The mixture of sample and antibody may then be combined with polypeptide antigen immobilized on a suitable solid support. Antibody that has not bound to an antigen in the sample is allowed to bind to the immobilized antigen and the remainder of the sample and antibody is removed. The level of antibody bound to the solid support is inversely related to the level of antigen in the sample. Thus, a lower level of antibody bound to the solid support indicates the presence of M. leprae in the sample. Other formats for using monospecific antibodies to detect M. leprae in a sample will be apparent to those of ordinary skill in the art, and the above formats are provided solely for exemplary purposes.

As used in this specification and the appended claims, the singular forms "a", "an" and "the" include plural referents unless the content clearly dictates otherwise. Thus, for example, reference to "a polypeptide" optionally includes two or more polypeptides, and the like.

It is understood that aspect and embodiments of the disclosure described herein include "comprising," "consisting," and "consisting essentially of aspects and embodiments.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

EXAMPLES

Example 1

Antigen Recognition in Leprosy Patient Samples.

Subjects and samples. Recently diagnosed and previously untreated leprosy patients and endemic controls (EC) were recruited at Centra de Referencia em Diagnostico e Terapeutica and Hospital Anuar Auad, Goiania, Goias State, Brazil. Leprosy patients were categorized as paucibacillary (PB) by clinical, bacilloscopic and histological observations (bacterial index, skin lesions, nerve involvement and histopathology) carried out by qualified personnel. Blood was obtained from tuberculosis patients (*Mycobacterium tuberculosis* sputum-positive, HIV-negative individuals with clinically confirmed pulmonary tuberculosis) who were undergoing treatment. EC were healthy individuals who had never had tuberculosis, had no history of leprosy in the family, and were living in the leprosy endemic area. All donors had previously been immunized with BCG and all blood samples were obtained after informed consent and after local ethics committee approval.

Determining reactivity by 24 hour whole blood assay (WBA). WBA were performed with venous undiluted heparinized whole blood (Greiner). Within 2 hours of collection, blood was added to each well of a 24-well plate (450 μl/well; Sigma, St. Louis, MO) and incubated with antigens at 37° C., 5% CO2. For each assay, stimulations were conducted with 10 μg/ml of recombinant protein and 1 μg/ml PHA (Sigma). After 24 hours, plasma was collected and stored at −20° C. IFNγ content within the plasma was determined by ELISA, used according to the manufacturer’s instructions (QuantiFERON CMI Cellestis, Carnegie, Australia). The detection limit of the test was 0.05 IU/ml. For data interpretation, a positive result was assigned as a concentration above an arbitrary cut-off point of 0.5 IU/ml. Spontaneous IFNγ secretion was observed in WBA only for some TB patients, and in those cases, was subtracted to provide antigen-induced values.

Antigen recognition by leprosy-affected individuals. Replication and dissemination of *M. leprae* is limited in PB leprosy patients and most HHC, suggesting the potent cellular immune response they develop is associated with limited or localized disease. Antigens that are recognized by PB patients or HHC are potentially targets of an effective immune response against *M. leprae*. To further the antigen selection scheme, the analyses was expanded to include ethnically and geographically distinct populations (Table 1). While each of the individual antigens ML2028, ML2055 and ML2380 were recognized by over 50% PB patients and HHC, the combination of these antigens pushed the theoretical recognition to over 80%.

Table 1. Percent responders above 50 pg/ml IFNγ in WBA. Whole blood from PB and HHC was cultured for 24 hours in the presence of antigen and IFNγ content in the plasma was measured by ELISA. Data were generated with cohorts from Brazil and the Philippines.

TABLE 1

Percent responders above 50 pg/ml IFNγ in WBA

| | Antigens | Total # | # Positive Responders | # Negative Responders | % Positive Responders |
|---|---|---|---|---|---|
| observed | ML2028 | 129 | 77 | 52 | 59.7 |
| | ML2055 | 130 | 90 | 40 | 69.2 |
| | ML2380 | 68 | 45 | 23 | 66.2 |
| theoretical | ML2028 + ML2055 | 70 | 51 | 19 | 72.9 |
| | ML2028 + ML2380 | 32 | 26 | 6 | 81.3 |
| | ML2055 + ML2380 | 32 | 27 | 5 | 84.4 |
| | ML2028 + ML2055 + ML2380 | 32 | 27 | 5 | 84.4 |

Mice and immunizations. Wild type C57BL/6 (B6) mice were purchased from Charles River Laboratories (Wilmington, MA). Mice were immunized with recombinant protein formulated with saline, stable emulsion (SE), or glucopyranosyl lipid adjuvant (GLA)-SE, to provide a final protein concentration of 10 μg antigen and 20 μg GLA-SE. Mice were immunized up to 3 times by subcutaneous (s.c) injection of 0.1 ml volume at the base of the tail at 2 week intervals. Mice were maintained in specific pathogen-free conditions and all procedures were approved by the pertinent institutional animal care and use committees.

Immunization with Select Antigens Reduces *M. Leprae* Infection.

Determination of bacterial burden. To assess *M. leprae* growth, live *M. leprae* bacilli (Thai-53 strain) were purified from the footpads of nu/nu mice at National Institute of Infectious Diseases. Mice were inoculated with 1×104 bacilli by s.c. injection into each foot pad. Foot pads were harvested 12 months later and the bacilli were enumerated by direct microscopic counting of acid-fast bacilli according to the method of Shepard and McRae or by RT-PCR of the *M. leprae* specific repetitive element (RLEP).

Immunization with select antigens reduces *M. leprae* infection. To investigate if immunization with the recognized antigens could limit *M. leprae* infection, mice were immunized with single antigens, or combinations of antigens, before infection with *M. leprae*. Immunization significantly decreased bacterial numbers (FIGS. 1A and 1B; p-values <0.05). These data indicate that immunization with the selected antigens elicits protective responses in mice and warrant inclusion within a defined sub-unit vaccine against leprosy.

Generation of ML89 Fusion Protein A single 89 kD fusion protein, designated ML89, was generated from the ML2028, ML2055 and ML2380 antigens, with the addition of ML2531 to stabilize expression.

Immune Recognition of Chimeric Fusion Protein ML89.

Antibody responses. Mouse sera were prepared following collection of retro-orbital blood into microtainer serum collection tubes (VWR International, West Chester, PA) followed by centrifugation at 1200 rpm for 5 minutes. Each serum was then analyzed by antibody capture ELISA. Briefly, ELISA plates (Nunc, Rochester, NY) were coated with 1 μg/ml recombinant antigen in 0.1 M bicarbonate buffer and blocked with 1% BSA-PBS. Then, in consecutive order and following washes in PBS/Tween®20, serially diluted serum samples, anti-mouse IgG, IgG1 or IgG2c-HRP (all Southern Biotech, Birmingham, AL) and ABTS-H2O2 (Kirkegaard and Perry Laboratories, Gaithersburg, MD) were added to the plates. Plates were analyzed at 405 nm (ELX808, Bio-Tek Instruments Inc, Winooski, VT). Endpoint titer was determined as the last dilution to render a positive response, determined as 2 times the mean optical density of the replicates derived from sera from unimmunized mice in Prism software (GraphPad Software, La Jolla, CA).

Antigen stimulation and cytokine responses. Single cell suspensions were prepared by disrupting spleens between frosted slides. Red blood cells were removed by lysis in 1.66% NH4CI solution, then mononuclear cells enumerated by Via Count assay with a PCA system (Guava Technologies, Hayward, CA). Single cell suspensions were cultured at 2×105 cells per well in duplicate in a 96-well plate (Corning Incorporated, Corning, NY) in RPMI-1640 supplemented with 5% heat-inactivated FCS and 50,000 Units penicillin/streptomycin (Invitrogen). Cells were cultured in the presence of 10 μg/ml antigen for 72-96 hours, after which culture supernatants were harvested and cytokine content assessed. Cytokine concentrations within culture supernatants were determined by single cytokine ELISA or multiple cytokine luminex assays. ELIS A kits for determination of mouse IFNγ, IL-5, IL-13 and TNF-α were performed according to manufacturer's instructions (eBioscience, San Diego, CA) and optical density was determined using an ELx808 plate reader.

Immune recognition of chimeric fusion protein ML89. Combining multiple antigens into a single fusion protein is now commonly used to provide a more consistent production process whilst also increasing the proportion of the population that is likely to respond. We therefore created a single 89 kD fusion protein, designated ML89, consisting of the ML2028, ML2055 and ML2380 antigens, with the addition of ML2531 to stabilize expression. When mice were immunized with the ML89 they raised antibodies against each individual component (FIGS. 2B-2D), indicating that antigenicity was retained. Given that the *M. bovis* BCG vaccine is routinely used in leprosy-affected regions, we also examined the interplay of ML89 and BCG vaccination and determined if prior BCG immunization led to any interactions upon ML89 immunization. Mice were either primed with BCG or not, then immunized with ML89/GLA-SE. Subsequent analyses of the IFNγ recall response to ML89 indicated similar responses in both immunization strategies (FIG. 3A). Furthermore, mice immunized with ML89 also responded to lysate of BCG and, most importantly, to crude *M. leprae* antigens (FIGS. 3B and 3D). These data indicate that recognition of ML89 raises responses that recognize *M. leprae* that are not adversely affected by prior BCG immunization.

Immunization with ML89/GLA-SE Reduces *M. leprae* Burdens.

Determination of bacterial burden. To assess *M. leprae* growth, live *M. leprae* bacilli (Thai-53 strain) were purified from the footpads of nu/nu mice at National Institute of Infectious Diseases. Mice were inoculated with 1×104 bacilli by s.c. injection into each foot pad. Foot pads were harvested 12 months later and the bacilli were enumerated by direct microscopic counting of acid-fast bacilli according to the method of Shepard and McRae or by RT-PCR of the *M. leprae* specific repetitive element (RLEP).

Immunization with ML89/GLA-SE reduces *M. leprae* burdens. We hypothesized that immunization with the ML89 antigen would limit bacterial growth, and evaluated the ability of the ML89/GLA-SE vaccine candidate to protect against experimental *M. leprae* infection using the BALB/c mouse footpad model. Immunized mice were infected with *M. leprae* in the footpad and bacilli numbers assessed months later. The vaccine decreased bacterial numbers by 85% when compared with mice injected with GLA-SE adjuvant alone (FIG. 4A; p-values <0.05). Immunization with ML89/GLA-SE elicited protection equivalent to the mixture of its individual components, and could provide protection when injected 2 or 3 times (FIG. 4B; p-values <0.05). Taken together, the data indicated that the defined subunit ML89/GLA-SE vaccine induces responses that control of *M. leprae* infection.

Immunization with ML89/GLA-SE reduced lymphadenopathy induced by *M. leprae* infection. Mice were injected s.c. with ML89/GLA-SE at biweekly intervals, for a total of 3 immunizations. One month after the last immunization mice were infected with 1×106 *M. leprae* in each ear, and DLN cell numbers determined 16 weeks later. Results are shown as mean and SE (n=5 per group). Student's t-test was used to calculate p-values between each group.

ML89-specific T cells reduced *M. leprae* viability during experimental infection. Mice were injected s.c. with ML89/GLA-SE at biweekly intervals, for a total of 3 immunizations. One month after the last immunization T cells were purified from the spleens of immunized mice and transferred by i.v. injection into athymic recipient mice. Recipient mice were infected with 1×104 *M. leprae* in each foot, and bacilli numbers and viability determined 1 month later. Results are shown as mean and SE. Mann-Whitney test was used to calculate p-values between each group; n=6 per group.

Immunization with ML89/GLA-SE Delays Motor Nerve Function Impairment

The manifestation of leprosy in nine-banded armadillo (*Dasypus novemcinctus*), the only other natural host of *M. leprae*, is strikingly similar to humans. Most significantly, armadillos develop extensive nerve involvement during experimental *M. leprae* infection and can exhibit many classic clinical signs such as foot ulcers, skin lesions and even blindness. Armadillos are an abundant source of leprotic neurologic fibers and they have already provided some important insights into the demyelinating neuropathy involved in leprosy. Marked inflammation can be observed on histopathological inspection of infected armadillo nerves and a functional deficit can be demonstrated in leprotic nerves using electrophysiology. Importantly, among the unique attributes of experimental infection in armadillos are a controlled and known infection status, and functional recapitulation of leprosy as seen in humans but with a compressed time until disease emergence.

Figure 5A:
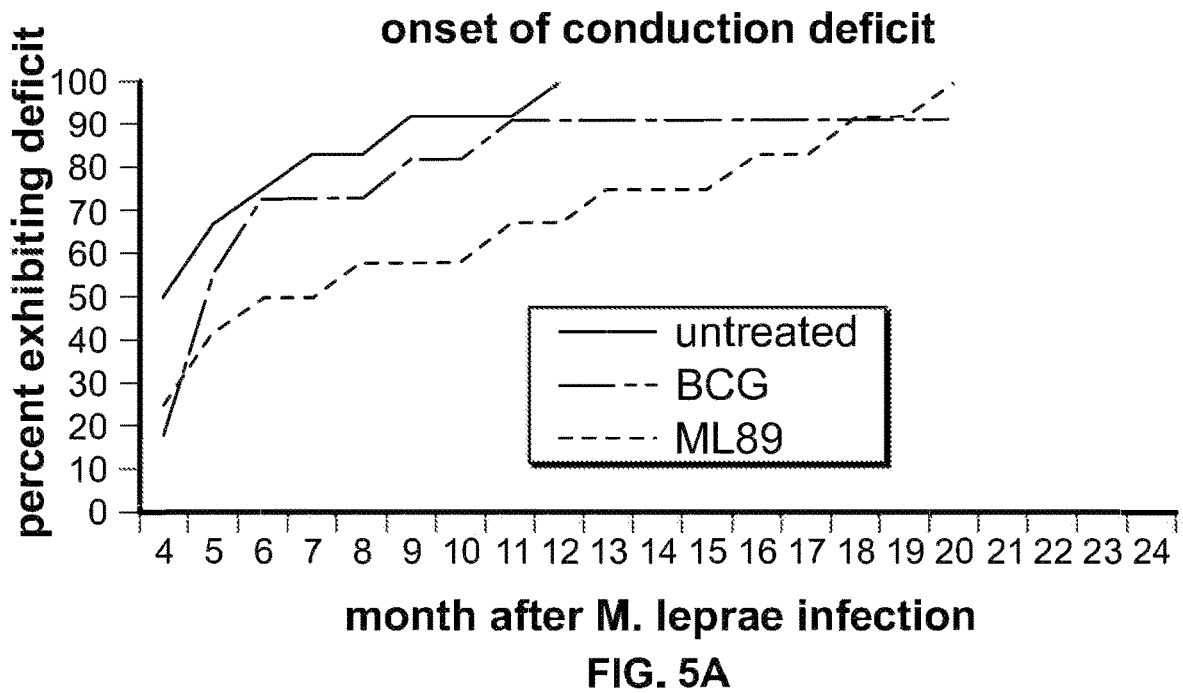
Figure 5B:
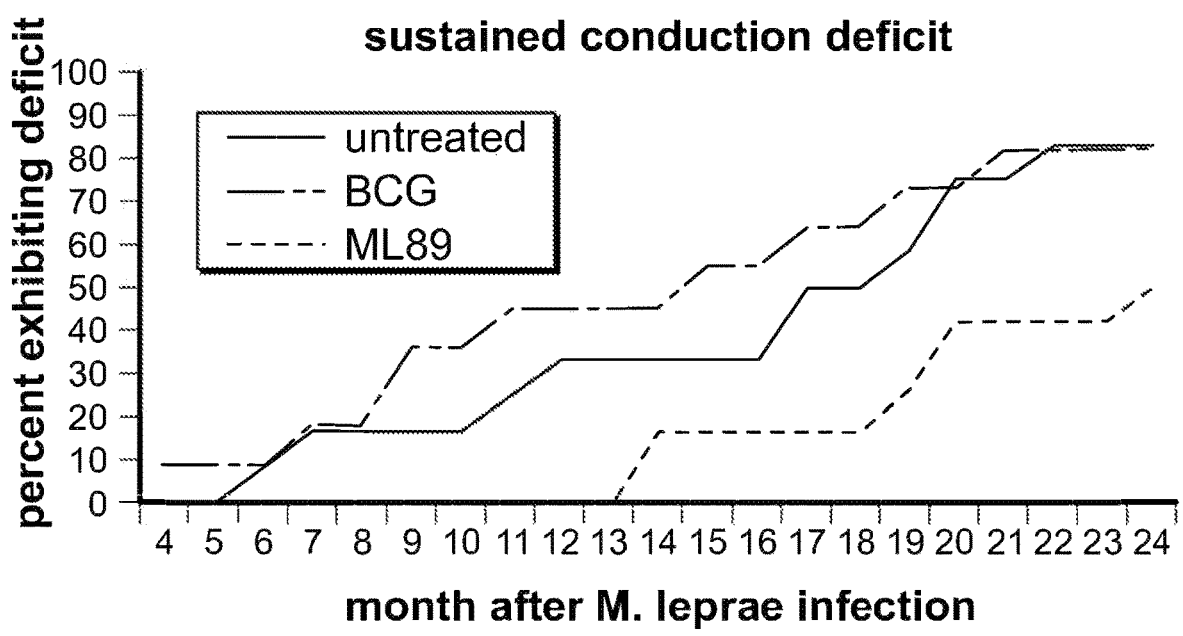
Figure 5C:
Figure 5C:
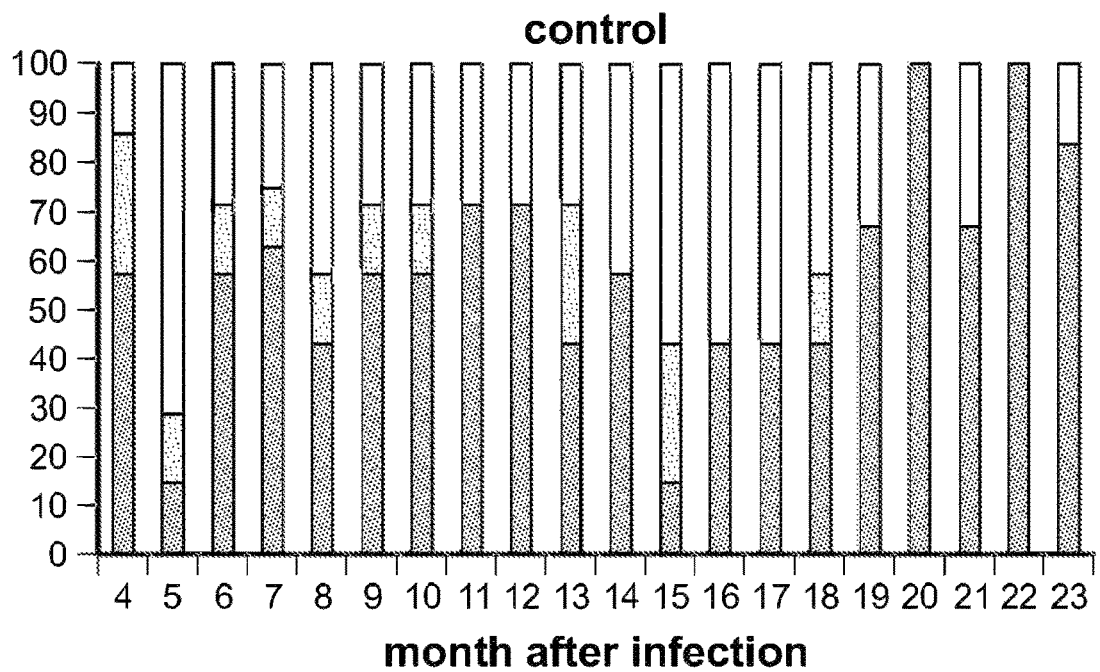
Figure 5C:
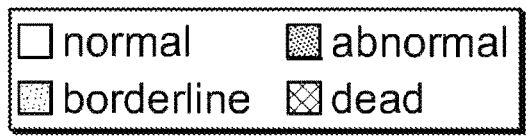
Figure 5C:
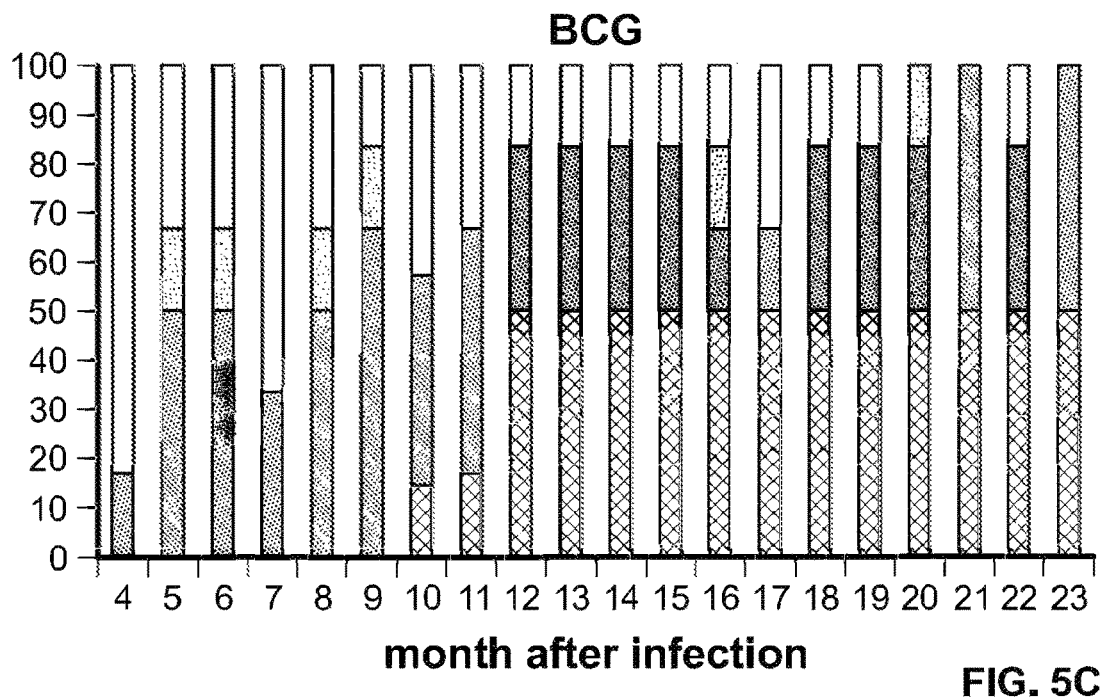
Figure 5C:
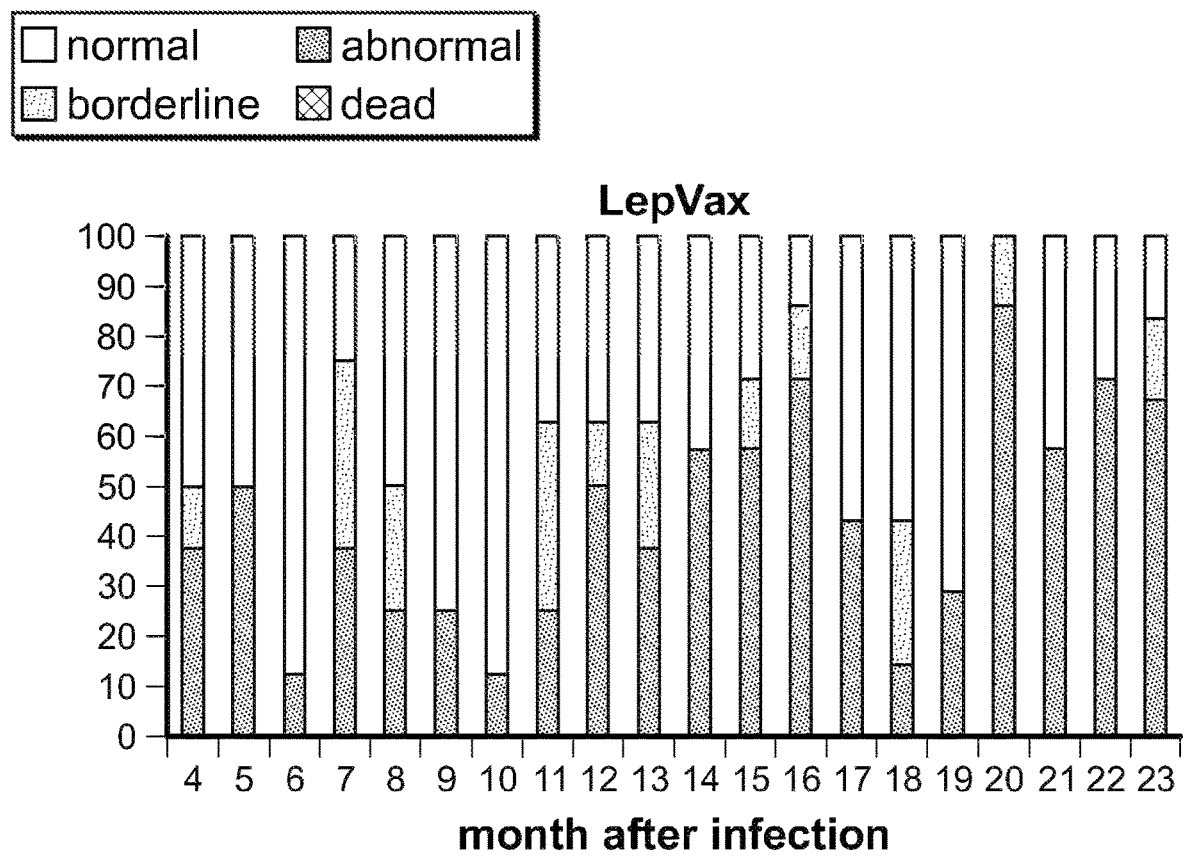

Immunization with ML89/GLA-SE delays motor nerve function impairment. Given that the hallmark of leprosy is nerve damage, the vaccine was evaluated in nine-banded armadillos that develop the nerve involvement and functional perturbations seen in humans. To mimic a situation that may commonly arise in leprosy hyper-endemic regions, namely asymptomatic *M. leprae* infection, armadillos were infected prior to immunization then monitored for motor nerve conduction abnormality. Untreated armadillos began to show nerve conduction deficits as early as 4 months after inoculation, and all armadillos had had at least some measurable deficit by 12 months (FIG. 5A). Many animals that exhibited conduction deficits one month demonstrated a return to normal measurements the next. To account for these fluctuations, an animal demonstrating 3 consecutive months with abnormal readings was defined as exhibiting a sustained deficit. The variable nature of *M. leprae* infection in these outbred animals became apparent using this parameter, with sustained nerve conduction deficits occurring 6-22 months after infection and 2 of 12 (17%) infected armadillos not actually demonstrating persistent alterations (FIG. 5B). Interestingly, BCG immunization of already infected animals led to precipitation of nerve damage. While onset of conduction deficits in BCG vaccinated armadillos occurred at the same time as control untreated animals (FIG. 5a), sustained conduction deficits were more rapidly observed in BCG vaccinated armadillos than control untreated animals (FIG. 5b). The extent of the dissemination was significant enough that 27% (3 of 11) of the BCG immunized armadillos had to be removed from the study. Sustained conduction deficits were also more rapidly observed in BCG vaccinated armadillos than control untreated animals. In stark contrast, LEP-F1/GLA-SE immunization delayed the onset of motor nerve conduction abnormality among animals already incubating leprosy (FIG. 5B). It is highly pertinent that LEP-F1/GLA-SE immunization, at a minimum, appears to be safe and induces no further neurological injury in armadillos.

| GROUP | ID | Time of Sacrifice | Comment |
|---|---|---|---|
| BCG | 11I203 | 12 months | |
|  | 11I302 | 12 months | |
|  | 11I903 | 10 months | |
|  | 12M41 | 19 months | |
| ID93 | 11J201 | 32 months | Not sure dissemination |
|  | 11J301 | 23 months | |
|  | 11J901 | 13 months | |
|  | 12O68 | 23 months | |

Statistics. For human data, the Mann Whitney U test was applied for comparison between two groups. The nonparametric Kruskal-Wallis analysis of variance test was used to compare the IFNγ levels among all groups. The p-values for mouse studies resulting in normally distributed data including 2 groups were determined using the Student's t-test. Where more than 2 groups were compared, p-values were attained by ANOVA analyses. Data were log-transformed for non-normal data sets prior to analysis. Statistics were generated using MS Excel (Microsoft Corporation, Redmond, WA) or Prism software (GraphPad Software, Inc., La Jolla, CA). Statistical significance was considered as p-values were <0.05.

DISCUSSION

Despite the positive impact that WHO-MDT has had on the global prevalence of leprosy, there are many indications that further efforts are required to prevent the re-emergence of leprosy and continue efforts toward eradication. Targeting vaccination to at-risk populations, amongst which many individuals may already be infected with *M. leprae*, appears a tenable long lasting strategy. Many countries re-immunize leprosy patients and their close contacts with the *Mycobacterium bovis* BCG vaccine developed against tuberculosis. Immunization with BCG does afford some protection, although meta-analyses of clinical trials estimated its ability to prevent leprosy to be modest (26% and 41%, respectively) (Setia et al., Lancet Infect. Dt. 2006; 6(3): 162-170; Merle et al. Expert Review of Vaccines. 2010; 9(2):209-22.)

The persistence of leprosy in regions with good BCG coverage indicates that additional strategies are required.

Although *M. leprae* is killed by MDT, neurological injury continues to occur in patients and can be exacerbated during inflammatory reactional episodes. Some clinicians/researchers fear that immunization to boost inflammatory T cell responses will induce nerve-damaging reversal reactions. Live attenuated or killed mycobacteria vaccines have generally been well tolerated in patients and the incidence of reactions has not been dramatically altered versus unvaccinated groups, while more rapid bacterial clearance has occurred and has been accompanied by distinct signs of clinical improvement. Anecdotal reports, and now clinical evidence, indicate that BCG immunization may however precipitate the onset of PB disease in some individuals, with speculation that infected but asymptomatic *M. leprae*-infected individuals are at greatest risk. To date, however, the effect of vaccination on *M. leprae*-associated neuropathy has not been investigated in a controlled system. The data demonstrated that BCG vaccination precipitates nerve damage in *M. leprae*-infected armadillos, supporting that hypothesis that infected individuals are at risk of disease precipitation if vaccinated with BCG.

Thus, it was surprising that the data indicated that LEP-F1/GLA-SE immunization was safe but also delayed nerve damage in animals infected with high doses of *M. leprae*.

As would be recognized by the skilled artisan, these and other changes can be made to the embodiments of the disclosure in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

Example 2

GLP Repeated Dose Toxicity Study in Rabbits

A study to determine the potential toxicity of LEP-F1+GLA-SE in New Zealand White rabbits when given every 14 days via IM injection for 6 weeks as well as to determine if delayed toxicity and/or recovery occurred after a 4 week recovery period was performed. Systemic exposure was evaluated by anti-LEP-F1 antibody analysis. Forty animals were divided into two groups and received either saline or LEP-F1 (20 ug)+GLA-SE (20 ug). The animals were dosed by IM Injection on Days 1, 15, 29 and 43. None of the findings were considered to be highly toxicologically significant and all had resolved by the end of the recovery period.

Example 3

Phase I Open Label Antigen Dose-Escalation Clinical Trial to Evaluate the Safety, Tolerability, and Immunogenicity of LEP-F1+GLA-SE in Healthy Adult Subjects To evaluate the safety and tolerability of 2 ug LEP-F1+5 ug GLA-SE and 10 ug LEP-F1+5 ug GLA-SE following 1M administration on study days 0, 28, and 56 and to assess the immunogenicity of 2 ug LEP-F1+5 ug GLA-SE and 10 ug LEP-F1+5 ug GLA-SE by evaluating T cell responses to LEP-F1 at specified time points, a Phase I clinical trial will be performed. The proposed clinical trial is a first-in-man trial to establish an initial safety profile in mycobacterially naive healthy adults. The evaluation of vaccine-induced immunity will be based on the development of circulating antibody and T cell responses directed against the LEP-F1 antigen. Primary response will be assessed at Day 63. Responses at baseline and Day 35 will also be assessed. Each participant will be on study for 14 months. Serum will be collected on days 0, 35, and 63. These samples will be used to determine by IgG ELISA whether subjects have antibody responses to the LEP-F1 antigen at each of these time points. Measured antibody responses to LEP-F11 will be reported as normalized titers. Cellular immune response analysis of selected Th1 and Th2 cytokines specific to LEP-F1 will be assayed on days 0, 35, and 63 by whole blood assay. Cytokine concentrations will be quantified by ELISA or multiplex bead array.

It is anticipated that adverse events will be generally mild, transient and typical of immunizations given by the IM. route. It is expected that subjects receiving LEP-F1+GLA-SE will have robust levels of antigen specific IgG antibodies and will display antigen-specific CD4+ T cell responses.

---

SEQUENCES

Polynucleotide Encoding ML2028 Antigen
SEQ ID NO: 1

ATGATTGACGTGAGCGGGAAGATCCGAGCCTGGGGCGCTGGCTTTTGGTGGGTGCAGCTGCGACTCTGCCGAGCCT

AATCAGCCTTGCTGGCGGAGCGGGCGACCGCAAGCGCGTTCTCACGACCAGGCCTACCCGTCGAGTACCTACAGGTG

CCGTCGGAGGCGATGGGGCGCAGCACAAGGTGCAGTTTCAAAACGGCGGAAACGGCTCTCCGGCGGTGTATCTGCTG

GATGGTTTGCGTGCGCAGGACGACTATAACGGCTGGGACATCAACACCTCCGCATTCGAGTGGTACTATCAGTCGGG

ACTCTCGGTCGTGATGCCGGTCGGTGGGCAATCCAGCTTCTACAGCGACTGGTACAGCCCAGCGTGCGGCAAGGCAG

GTTGCACGACCTACAAGTGGGAAACATTCCTTACTAGCGAGCTGCCTAAATGGCTATCCGCCAATAGGAGTGTCAAA

TCCACCGGCAGCGCCGTGGTCGGCCTCTCGATGGCCGGTTCCTCGGCCCTAATACTGGCAGCTTATCACCCCGATCA

GTTCATCTATGCTGGCTCGTTGTCGGCGCTGATGGACTCCTCCCAGGGGATAGAACCCCAGCTAATCGGCTTGGCGA

TGGGTGATGCTGGTGGCTACAAGGCCGCGGACATGTGGGGGACCACCAATGACCCGGCCTGGCAACGAAACGACCCC

ATTCTGCAGGCTGGGAAGCTGGTCGCCAACAACACCCACCTATGGGTTTACTGTGGTAACGGCACACCGTCAGAGTT

GGGTGGAACCAACGTACCCGCGGAATTCCTGGAGAACTTCGTGCACGGCAGCAACCTAAAGTTCCAGGACGCCTACA

ACGGTGCTGGTGGCCACAACGCTGTGTTCAACCTCAATGCCGACGGAACGCACAGCTGGGAGTACTGGGGAGCCCAG

CTCAACGCCATGAAGCCCGACCTACAGAACACCTTGATGGCTGTACCCCGCAGCGGT

Amino Acid Sequence of ML2028 Antigen from *Mycobacterium leprae*
(diacylglycerol acyltransferase; NCBI Reference Sequence: WP 010908679.1)
SEQ ID NO: 2

MIDVSGKIRAWGRWLLVGAAATLPSLISLAGGAATASAFSRPGLPVEYLQVSPSEAMGRSIKQFQNGGNGSPAVYLL

DGLRAQDDYNGWDINTSAFEWYYQSGLSVVMPVGGQSSFYSDWYSPACGKAGCTTYKWETFLTSELPKWLSANRSVK

STGSAVVGLSMAGSSALILAAYHPDQFIYAGSLSALMDSSQGIEPQLIGLAMGDAGGYKAADMWGPPNDPAWQRNDP

ILQAGKLVANNTHLWVYCGNGTPSELGGTNVPAEFLENFVHGSNLKFQDAYNGAGGHNAVFNLNADGTHSWEYWGAQ

LNAMKPDLQNTLMAVPRSG

Polynucleotide Encoding ML28028$_{39-327}$
SEQ ID NO: 3

TTCTCACGACCAGGCCTACCCGTCGAGTACCTACAGGTGCCGTCGGAGGCGATGGGGCGCAGCATCAAGGTGCAGTT

TCAAAACGGCGGAAACGGCTCTCCGGCGGTGTATCTGCTGGATGGTTTGCGTGCGCAGGACGACTATAACGGCTGGG

| SEQUENCES |
|---|
| ACATCAACACCTCCGCATTCGAGTGGTACTATCAGTCGGGACTCTCGGTCGTGATGCCGGTCGGTGGGCAATCCAGC |
| TTCTACAGCGACTGGTACAGCCCAGCGTGCGGCAAGGCAGGTTGCACGACCTACAAGTGGGAAACATTCCTTACTAG |
| CGAGCTGCCTAAATGGCTATCCGCCAATAGGAGTGTCTCAAATCCACCGGCAGCGCCGTGGTCGGCCTCTGATGGCC |
| GTTCCTCGGCCCTAAATATACTGGCAGCTTATCACGATCAGTTCATCTATGCTGGCTCGTTCTCGGCGCTGATGGAC |
| TCCTCCCAGGGGATAGAACCCCAGCTAATCGGCTTGGCGATGGGTGATGCTGGTGGCTACAAGGCCGCGGACATGTG |
| GGGACCACCAAATGACCCGGCCTGGCAACGAAACGACCCCATTCTGCAGGCTGGGAAGCTGGTCGCCAACAACACCC |
| ACCTATGGGTTTACTGTGGTAACGGCACACCGTCAGAGTTGGGTGGAACCAACGTACCCGCGGAATTCCTGGAGAAC |
| TTCGTGCACGGGAGCAACCTAAAGTTCCAGGACGCCCAGCTCAACGCCATGAAGCCGACCTACAGAACACACCTTGA |
| TGCCGACGGAACGCACAGCTGGGAGTACTGGGGAGCCCAGCTCAACGCCATGAAGCCCGACCTACAGAACACCTTGA |
| TGGCTGTACCCCGCAGCGGT |
| Amino Acid Sequence of Residues 39-327 of ML2028 antigen (ML2028$_{39-327}$)<br>SEQ ID NO: 4 |
| FSRPGLPVEYLQVPSEAMGRSIKVQFQNGGNGSPAVYLLDGLRAQDDYNGWDINTSAFEWYYQSGLSVVMPVGGQSS |
| FYSDWYSPACGKAGCTTYKWETFLTSELPKWLSANRSVKSTGSAVVGLSMAGSSALILAAYHPDQFIYAGSLSALMD |
| SSQGIEPQLIGLAMGDAGGYKAADMWGPPNDPAWQRNDPILQAGKLVANNTHLWVYCGNGTPSELGGTNVPAEFLEN |
| FVHGSNLKFQDAYNGAGGHNAVFNLNADGTHSWEYWGAQLNAMKPDLQNTLMAVPRSG |
| Polynucleotide Encoding ML2055 Antigen<br>SEQ ID NO: 5 |
| ATGAATCAGGTTGACCTGGACTCGACACATCGCAAAGGATTGTGGGCGATACTGGCGATTGCCGTGGTGGCCAGCGC |
| CAGTGCCTTTACGATGCCGTTGCCTGCGGCCGCCAACGCCGATCCCGCGCCCCTGCCGCCATCGACGGCTACGGCAG |
| CTCCCTCACCTGCGCAGGAGATCATTACACCCCTTCCAGGCGCCCCTGTCTCGTCCGAAGCCCAACCGGGTGATCCC |
| AATGCGCCGTCGCTCGATCCGAATGCACCATACCCACTTGCAGTCGATCCCAACGCCGGCCGAATCACCAACGCTGT |
| CGGTGGATTTAGCTTCGTCCTTCCTGCCGGTTGGGTGGAGTCAGAGGCTTCACATCTTGACTACGGTTCGGTGCTGC |
| TCAGCAAAGCCATCGAGCAGCCGCCCGTGCTTGGTCAGCCGACGGTGGTCGCTACCGACACCCGTATAGTGCTCGGC |
| CGGCTGGACCAAAAGCTCTACGCCAGTGCCGAAGCCGACAACATTAAGGCCGCGGTCCGACTGGGCTCGGATATGGG |
| TGAGTTCTACCTGCCATACCCCGGTACGCGGATCAACCAAGAAACCATTCCGCTCCACGCCAACGGGATAGCTGGAA |
| GCGCCTCCTACTACGAGGTCAAATTCAGCGATCCCAATAAGCCAATTGGCCAAATATGTACGAGCGTAGTCGGCTCG |
| CCAGCGGCGAGTACCCCTGACGTGGGGCCCTCGCAGCGTTGGTTTGTGGTATGGCTCGGAACCTCGAATAACCCGGT |
| GGACAAGGGCGCAGCCAAAGAGCTGGCTGAGTCTATCCGGTCAGAGATGGCTCCGATCCCGAGCGTCGGTTCCGCTC |
| CGGCACCTGTTGGA |
| Amino Acid Sequence of ML2055 Antigen from *Mycobacterium leprae*<br>(alanine and proline-rich secreted protein Apa; NCBI Reference Sequence:<br>WP_010908692.1)<br>SEQ ID NO:6 |
| MNQVDLDSTHRKGLWAILAIAVVASASAFTMPLPAAANADPAPLPPSTATAAPSPAQEIITPLPGAPVSSEAQPGDP |
| NAPSLDPNAPYLAVDPNAGRITNAVGGFSFVLPAGWVSESEASHLDYGSVLLSKAIEQPPVLGQPTVVATDTRIVLG |
| RLDQKLYRASAEADNIKAAVRLGSDMGEFYLPYGTRINQETIPLHANGIAGSASYYEVKFSDPNKPIGQICTSVVGS |
| PAASTPDVGPSQRWFVVWLGTSNNPVDKGAAKELAESIRSEMAPIPASVSAPAPVG |
| Polynucleotide Encoding ML2380 Antigen<br>SEQ ID NO: 7 |
| ATGTCTCGGCTGAGCACCAGCCTATGTAAAGGTGCTGTTTTCTCGTTTTCGGTATCATTCCTGTGGCATTTCCGAC |
| GACCGCCGTTGCCGATGGTTCCACGGAGGATTTTCCGATCCCCGCAGGCAAATCGCCACCACCTGTGATGCAGAGC |
| AGTATTTGGCGGCCGTCAGGGATAACCAGCCCCATACTACCAGCGGTACATGATCGATATGCACAACAAGCCCGAGT |
| GACATCCAGCAGGCCGCGGTCAATCGTATCCATTGGTTCTATTCCTTGAGCCCCACCGACCGTAGGCAGTATTCCGA |

| SEQUENCES |
| --- |

GGACACCGCTACAAACGTCTACTACGAGCAGATGCGGCCACGCATTGGGAAACTGGGCGAAGATTTCTTCAATAACA

AGGGCGTTGTTGTCGCCAAAGCCACCGAGGTTTGCAACCAGTACCAGGCCGGAGACATGTCGGTGTGGAACTGGCCG

Amino Acid Sequence of ML2380 Antigen from *Mycobacteriun leprae*
(Hypothetical protein; NCBI Reference Sequence: WP_010908863.1)

SEQ ID NO: 8

MSRLSTSLCKGAVFLVFGIIPVAFPTTAVADGSTEDFPIPRRQIATTCDAEQYLAAVRDTSPIYYQRYMIDMHNKPT

DIQQAAVNRIHWFYSLSPTDRRQYSEDTATNVYYEQMATHWGNWAKIFFNNKGVVAKATEVCNQYQAGDMSVWNWP

Polynucleotide Encoding ML2531 Antigen

SEQ ID NO: 9

ATCACACAGATTATGTACAACTACCCGGCAATGTTGGACCACGCCGGGAATATGTCAGCCTGCGCCGGCGCTTTGCA

GGGGGTGGGCATCGACATCGCTGCCGAGCAAGCTGCGTTGCAAGCTTGCTGGGGGGGCGATACTGGGATTAGTTATC

AGGCCTGGCAGGTGCAGTGGAACCAGGCCACGGAAGAGATGGTGCGTGCCTACCATGCAATGGCCAACACTCACCAA

ACAACACTTTGGCTATGCTCACCCGCGACCAAGCTGAAGCCGCCAAATGGGGCGGC

Amino Acid Sequence of ML2531 Antigen from *Mycobacterium leprae*
(ESAT-6-like protein EsxR; NCBI Reference Sequence: WP_010908945.1)

SEQ ID NO: 10

MTQIMYNYPAMLDHAGNMSACAGALQGVGIDIAAEQAALQACWGGDTGISYQAWQVQWNQATEEMVRAYHAMANTHQ

NNTLAMLTRDQAEAAKWGG

Polynucleotide Encoding the LEP-F1 Fusion Polypeptide

SEQ ID NO: 11

ATGACACAGATTATGTACAACTACCCGGCAATGTTGGACCACGCCCGGGAATATGTCAGCCTGCGCGGCGCTTTGCA

GGGGGTGGGCATCGACATCGCTGCCGAGCAAGCTGCGTTGCAAGCTTGCTGGGGGGGCGATACTGGGATTAGTTATC

AGGCCTGGCAGGTGCAGTGGAACCAGGCCACGGAAGAGATGGTGCGTGCCTACCATGCAATGGCCAACACTCACCAA

ACAACACTTTGGCTATGCTCACCCGCGACCAAGCTGAAGCCGCCAAATGGGGCGGCGGATCCATGTCTCGGCTGAG

CACCAGCCTATGTAAAGGTGCTGTTTTTCTCGTTTTCGGTATCATTCCTGTGGCATTTCCGACGACCGCCGTTGCCG

ATGGTTCCACGGAGGATTTTCCGATCCCCCGCAGGCAAATCGCCACCACCTGTGATGCAGAGCAGTATTTGGCGGCC

GTCGGGATACCAGCCCGATCTACTACCAGCGAGTACATGATCGATATGCACAACAAGCCGACTGACATCCAGCAGGC

CGCGGTCAATCGTATCCATTGGTTCTATTCCTTGAGCCCCACCGACCGTAGGCAGTATTCCGAGGACACCGGTACAA

ACGTCTACTACGAGCAGATGGCCACGCATTGGGGAAACTGGGCGAAGATTTTCTCCAATAACAAGGGCGTTGTCGCC

AAAGCCACCGAGGTTTGCAACCAGTACCAGGCCGGAGACATGTCGGTGTGGAACTGGCCGGAGCTCATGAATCAGGT

TGAAAACCTGGACTCGACACATCGAAAGGATTGTGGGCGATACTGGCGATTGCTGGTGGCCAGCGCCAGTGCCTTTA

CGATGCCGTTGCCTGCGGCCGCCAACGCCCGATCCCGCGCCCTGCCGCCATCGACGGCTACGGCAGCTCCCTCACCT

GCGCAGGAGATCATTACACCCCTTCCAGGCGCCCCTGTCTCGTCCGAAGCCCAACCGGGTGATCCCAATGCGCCGTC

GCTCGATCCGAATGCACCATACCCACTTGCAGTCGATCCCAACGCCGGCCGAATCACCAACGCTGTCGGTGGATTTA

GCTTCGTCCTTCCTGCCGGTTGGGTGGAGTCAGAGGCTTCACATCTTGACTACGGTTCGGTGCTGCTCAGGAAAGCC

ATCGAGCAGCCGCCCGTGCTTGGTCAGCCGACGGTGGTCGCTACCGACACCCGTATAGTGCTCGGCCGGCTGGACCA

AAAGCTCTACGCCAGTGCCGAAGGCGACAACATTAAGGCCGCGGTCCGACTGGGCTCGGATATGGGTGAGTTCTACC

TGCCATACCCCGGTACGCGGATCAACCAAGAAACCATTCCGCTCCACGCCAACGGGATAGCTGGAAGCGCCTCCTAC

TACGAGGTCAAATTCAGCGATCCCAATAAGCCAATTGGCCAAATATGTACGAGCGTAGTCGGCTCGCCAGCGGGGAG

TACCCCTGACGTGGGGCCCCTCGCAGCGTTGGTTTGTGGTATGGCTCGGAACCTCGAATAACCGGTGGACAAGGGCG

CAGCCAAAGAGCTGGCTGAGTCTATCCGGTCAGAGATGGCTCCGATCCCGGCGTCGGTTTCCGCTCCGGCACCTGTT

GGAGTCGACTTCTCACGACCAGGCCTACCCGTCGAGTACCTACAGGTGCCGTCGGAGGCGATGGGGCGCAGCATCAA

GGTGCAGTTTCAAAACGGCGGAAACGGCTCTCCGGCGGTGTATCTGCTGGATGGTTTGCGTGCGCAGGACGACTATA

| SEQUENCES |
|---|
| ACGGCTGGGACATCAACACCTCCGCATTCGAGTGGTACTATGAGTCGGGACTCTCGGTCGTGATGCCGGTCGGTGGG |
| CAATCCAGCTTCTACAGCGACTGGTACAGCCCAGCGTGCGGCAAGGCAGGTTGCACGACCTACAAGTGGGAAACATT |
| CCTTACTAGCGAGCTGCCTAAATGGCTATCCGCCAATAGGAGTGTCAAATCCACCGGCAGCGCCGTGGTCGGCCTCT |
| CGATGGCCGGTTCCTCGGCCCTAATACTGGCAGCTTATCACCCCGATCAGTTCATCTATGCTGGCTCGTTGTCGGCG |
| CTGATGGACTCCTCCCAGGGGATAGAACCCCAGCTAATCGGCTTGGCGATGGGTGATGCTGGTGGCTACAAGGCCGC |
| GGACATGTGGGGACCACCAAATGACCCGGCCTGGCAACGAAACGACCCCATTCTGCAGGCTGGGAAGCTGGTCGCCA |
| ACAACACCCACCTATGGGTTTACTGTGGTAACGGCACACCGTCAGAGTTGGGTGGAACCAACGTACCCGCGGAATTC |
| CTGGAGAACTTCGTGCACGGCAGCAACCTAAAGTTCCAGGACGCCTACAACGGTGCTGGTGGCCACAACGCTGTGTT |
| CAACCTCAATGCCGACGGAACGCACAGCTGGGAGTACTGGGGAGCCCAGCTCAACGCCATGAAGCCCGACCTACAGA |
| ACACCTTGATGGCTGTACCCCGCAGCGGT |
| Amino Acid Sequence of the LEP-F1 Fusion Polypeptide SEQ ID NO: 12 |
| MTQIMYNYPAMLDHAGNMSACAGALQGVGIDIAAEQAALQACWGGDTGISYQAWQVQWNQATEEMVRAYHAMANTHQ |
| NNTLAMLTRDQAEAAKWGGGSMSRLSTSLCKGAVFLVFIIPVAFPTTTAVADGSTEDFPIPRRQIATTCDAEQYLAA |
| VRDTSRIYYQRYMIDMHNKPTDIQQAAVNRIHWFYSLSPTDRRQYSEDTATNVYYEQMATHWGNWAKIFFNNKGVVA |
| KATEVCNQYQAGDMSVWVWPELMNQVDLDSTHRKGLWAILAIAVVASASAFTMPLPAAANADPAPLPPSTATAAPSP |
| AQEIITPLPGAPVSSEAQPGDPNAPSLDPNAPYPLAVDPNAGPITNAVGGFSFVLPAGWVESEASHLDYGSVLLSKA |
| IEQPPVLGQPTVVATDTRIVLGRLDQKLYASAEADNIKAAVRLGSDMGEFYLPYPGTRINQETIPLHANGIAGSASY |
| YEVKFSDPNKPIGQICTSVVGSPAASTFDVGPSQRWFVVWLGTSNNPVDKGAAKELAESIRSEMAPIFASVSAPAFV |
| GVDFSRPGLPVEYLQVPSEAMGRSIKVQFQNGGNGSPAVYLLDGLRAQDDYMGWDINTSAFEWYYQSGLSVVMPVGG |
| QSSFYSDWYSPACGKAGCTTYKWETFLTSELPKWLSANRSVKSTGSAVVGLSMAGSSALILAAYHPDQFIYAGSLSA |
| LMDSSQGIEPQLIGLAMGDAGGYKAADMWGPPNDPAWQRNDPILQAGKLVANNTHLWVYCGNGTPSELGGTNVPAEF |
| LENFVHGSNLKFQDAYNGAGGHNAVFNLNADGTHSWEYWGAQLNAMKPDLQNTLMAVPRSG |

TABLE 2

Results of alignment of ML2028 amino acid sequence with other species

| NAME | Cover | Identity | Accession |
|---|---|---|---|
| diacylglycerol acyltransferase [*Mycobacterium lepromatosis*] | 100% | 94% | WP_045843560.1 |
| diacylglycerol acyltransferase/mycolyltransferase Ag85A [*Mycobacterium haemophilum*] | 100% | 88% | WP_047314133.1 |
| diacylglycerol acyltransferase/mycolyltransferase Ag85A [*Mycobacterium* sp. E342] | 100% | 84% | WP_068052084.1 |
| diacylglycerol acyltransferase/mycolyltransferase Ag85A [*Mycobacterium scrofulaceum*] | 100% | 84% | WP_067276075.1 |
| diacylglycerol acyltransferase/mycolyltransferase Ag85A [*Mycobacterium* sp. E1747] | 100% | 83% | WP_068078824.1 |
| diacylglycerol acyltransferase [*Mycobacterium nebraskense*] | 100% | 84% | WP_046185518.1 |
| diacylglycerol acyltransferase/mycolyltransferase Ag85A [*Mycobacterium* sp. E2733] | 96% | 85% | WP_068048723.1 |
| MULTISPECIES: diacylglycerol acyltransferase/mycolyltransferase Ag85A [*Mycobacterium*] | 96% | 85% | WP_067924124.1 |
| Diacylglycerol acyltransferase/mycolyltransferase Ag85B [*Mycobacterium scrofulaceum*] | 100% | 83% | Q50397.1 |
| diacylglycerol acyltransferase/mycolyltransferase Ag85A [*Mycobacterium* sp. 852002-53434_SCH5985345] | 96% | 85% | WP_066954325.1 |
| diacylglycerol acyltransferase/mycolyltransferase Ag85A [*Mycobacterium szulgai*] | 98% | 83% | WP_068023768.1 |

TABLE 2-continued

Results of alignment of ML2028 amino acid sequence with other species

| NAME | Cover | Identity | Accession |
|---|---|---|---|
| diacylglycerol acyltransferase/mycolyltransferase Ag85A [Mycobacterium sp. 852002-40037_SCH5390672] | 100% | 83% | WP_067099382.1 |
| diacylglycerol acyltransferase/mycolyltransferase Ag85A [Mycobacterium asiaticum] | 98% | 84% | WP_065159015.1 |
| diacylglycerol acyltransferase/mycolyltransferase Ag85A [Mycobacterium avium] | 100% | 82% | WP_062899503.1 |
| MULTISPECIES: hypothetical protein [Mycobacterium avium complex (MAC)] | 100% | 82% | WP_003876576.1 |
| diacylglycerol acyltransferase/mycolyltransferase Ag85A [Mycobacterium gordonae] | 98% | 84% | WP_065044249.1 |
| hypothetical protein [Mycobacterium marinum] | 98% | 82% | WP_012394484.1 |
| secreted antigen 85-B [Mycobacterium ulcerans subsp. shinshuense] | 97% | 82% | BAV41604.1 |
| hypothetical protein [Mycobacterium avium] | 100% | 81% | WP_010949276.1 |
| antigen 85-B [Mycobacterium europaeum] | 96% | 83% | CQD16344.1 |
| hypothetical protein [Mycobacterium colombiense] | 98% | 82% | WP_007771267.1 |
| diacylglycerol acyltransferase [Mycobacterium indicus pranii] | 98% | 82% | WP_043954940.1 |
| diacylglycerol acyltransferase/mycolyltransferase Ag85A [Mycobacterium sp. E2462] | 100% | 81% | WP_068288134.1 |
| diacylglycerol acyltransferase [Mycobacterium sp. 012931] | 98% | 81% | WP_036426578.1 |
| 85B protein [Mycobacterium avium subsp. paratuberculosis] | 100% | 81% | AAM21939.1 |
| diacylglycerol acyltransferase/mycolyltransferase Ag85A [Mycobacterium intracellulare] | 96% | 82% | WP_064934819.1 |
| secreted antigen 85-B FbpB [Mycobacterium ulcerans Agy99] | 98% | 81% | ABL05230.1 |
| diacylglycerol acyltransferase [Mycobacterium kansasii] | 98% | 86% | WP_036402954.1 |
| Esterase [Mycobacterium sp. 012931] | 97% | 81% | EPQ47622.1 |
| diacylglycerol acyltransferase/mycolyltransferase Ag85A [Mycobacterium sp. E2479] | 98% | 81% | WP_067934350.1 |
| diacylglycerol acyltransferase [Mycobacterium gastri] | 98% | 85% | WP_036418777.1 |
| diacylglycerol acyltransferase/mycolyltransferase Ag85A [Mycobacterium colombiense] | 98% | 81% | WP_064951422.1 |
| diacylglycerol acyltransferase/mycolyltransferase Ag85A [Mycobacterium tuberculosis] | 98% | 83% | WP_055380413.1 |
| esterase, putative, antigen 85-B [Mycobacterium tuberculosis CDC1551] | 98% | 83% | AAK46207.1 |
| diacylglycerol acyltransferase/mycolyltransferase Ag85A [Mycobacterium interjectum] | 100% | 82% | WP_066912698.1 |
| antigen 85-B [Mycobacterium kansasii 824] | 97% | 86% | ETZ99389.1 |
| antigen 85-B [Mycobacterium bohemicum DSM 44277] | 100% | 81% | CPR05988.1 |
| diacylglycerol acyltransferase/mycolyltransferase Ag85A [Mycobacterium bovis] | 98% | 83% | WP_047713277.1 |

TABLE 3

Results of alignment of ML2055 amino acid sequence with other species

| Name | Cover | Identity | Accession |
|---|---|---|---|
| alanine and proline-rich secreted protein Apa [Mycobacterium lepromatosis] | 96% | 85% | WP_045843569.1 |
| alanine and proline-rich secreted protein Apa [Mycobacterium kansasii 662] | 94% | 61% | AIR16824.1 |
| alanine and proline-rich secreted protein Apa [Mycobacterium haemophilum] | 94% | 74% | WP_047317005.1 |
| hypothetical protein [Mycobacterium asiaticum] | 94% | 63% | WP_065145552.1 |
| alanine and proline-rich secreted protein Apa [Mycobacterium tuberculosis] | 94% | 68% | WP_031695336.1 |
| hypothetical protein [Mycobacterium gordonae] | 94% | 61% | WP_065165242.1 |
| hypothetical protein [Mycobacterium szulgai] | 94% | 62% | WP_068156628.1 |
| hypothetical protein [Mycobacterium tuberculosis] | 94% | 65% | WP_055369424.1 |
| hypothetical protein [Mycobacterium sp. 852014-50255_SCH5639931] | 94% | 66% | WP_067743767.1 |
| alanine and proline rich secreted protein [Mycobacterium ulcerans subsp. shinshuense] | 60% | 80% | BAV41641.1 |
| alanine and proline rich secreted protein Apa [Mycobacterium liflandii] | 60% | 80% | WP_015355514.1 |
| alanine and proline-rich secreted protein Apa [Mycobacterium canettii] | 94% | 64% | WP_044081122.1 |
| alanine and proline rich secreted protein [Mycobacterium marinum] | 60% | 80% | WP_020725275.1 |
| alanine and proline-rich secreted protein Apa [Mycobacterium gastri] | 60% | 79% | WP_036417094.1 |
| hypothetical protein [Mycobacterium sp. 1423905.2] | 94% | 58% | WP_067409357.1 |

TABLE 3-continued

Results of alignment of ML2055 amino acid sequence with other species

| Name | Cover | Identity | Accession |
|---|---|---|---|
| hypothetical protein [*Mycobacterium* sp. 1554424.7] | 94% | 66% | WP_066933007.1 |
| hypothetical protein [*Mycobacterium bovis*] | 94% | 65% | WP_024456921.1 |
| hypothetical protein [*Mycobacterium* sp. E1747] | 94% | 64% | WP_068079301.1 |
| fibronectin attachment protein [*Mycobacterium canettii*] | 94% | 65% | WP_015293251.1 |

TABLE 4

Results of alignment of ML2380 amino acid sequence with other species

| Name | Cover | Identity | Accession |
|---|---|---|---|
| hypothetical protein [*Mycobacterium lepromatosis*] | 100% | 89% | WP_045843787.1 |
| hypothetical protein [*Mycobacterium haemophilum*] | 100% | 87% | WP_047313676.1 |
| hypothetical protein [*Mycobacterium asiaticum*] | 99% | 74% | WP_065144676.1 |
| MULTISPECIES: hypothetical protein [*Mycobacterium*] | 88% | 73% | WP_051128635.1 |
| hypothetical protein [*Mycobacterium mucogenicum*] | 94% | 71% | WP_064985021.1 |
| hypothetical protein TL10_07350 [*Mycobacterium llatzerense*] | 92% | 68% | KIU17456.1 |
| hypothetical protein [*Mycobacterium vaccae*] | 100% | 65% | WP_040542321.1 |
| hypothetical protein [*Mycobacterium aurum*] | 99% | 65% | WP_048631131.1 |
| hypothetical protein [*Mycobacterium mucogenicum*] | 99% | 67% | WP_060999962.1 |
| hypothetical protein [*Mycobacterium* sp. NAZ190054] | 100% | 64% | WP_067953437.1 |
| hypothetical protein MCHLDSM_07340 [*Mycobacterium chlorophenolicum*] | 95% | 68% | KMO66863.1 |
| hypothetical protein [*Mycobacterium chubuense*] | 82% | 75% | WP_048421400.1 |
| hypothetical protein [*Mycobacterium* sp. Soil538] | 82% | 74% | WP_057150842.1 |
| hypothetical protein [*Mycobacterium iranicum*] | 96% | 64% | WP_024447804.1 |
| hypothetical protein [*Mycobacterium* sp. E2462] | 99% | 65% | WP_068289290.1 |
| hypothetical protein [*Mycobacterium gilvum*] | 99% | 61% | WP_011894296.1 |
| hypothetical protein [*Mycobacterium neoaurum*] | 83% | 75% | WP_036470504.1 |
| hypothetical protein BN971_02987 [*Mycobacterium bohemicum* DSM 44277] | 99% | 66% | CPR11699.1 |
| hypothetical protein [*Mycobacterium* sp. URHB0044] | 93% | 65% | WP_029115183.1 |
| hypothetical protein [*Mycobacterium tuberculosis*] | 99% | 66% | WP_031705761.1 |
| hypothetical protein [*Mycobacterium canettii*] | 99% | 66% | WP_015289054.1 |
| hypothetical protein [*Mycobacterium* sp. 852002-10029_SCH5224772] | 99% | 66% | WP_067256445.1 |
| hypothetical protein [*Mycobacterium africanum*] | 99% | 66% | WP_003910126.1 |
| hypothetical protein MT0471 [*Mycobacterium tuberculosis* CDC1551] | 99% | 66% | AAK44694.1 |
| hypothetical protein [*Mycobacterium* sp. 852002-50816_SCH5313054-b] | 99% | 65% | WP_066959997.1 |
| hypothetical protein [*Mycobacterium* sp. 360MFTsu5.1] | 95% | 66% | WP_036421759.1 |
| hypothetical protein [*Mycobacterium* sp. UNCCL9] | 83% | 75% | WP_036462037.1 |
| hypothetical protein BN000_02058 [*Mycobacterium europaeum*] | 99% | 65% | CQD10070.1 |
| hypothetical protein [*Mycobacterium* sp. E2479] | 99% | 66% | WP_067933987.1 |
| hypothetical protein [*Mycobacterium marinum*] | 99% | 66% | WP_036457021.1 |
| hypothetical protein [*Mycobacterium interjectum*] | 99% | 65% | WP_066917676.1 |
| hypothetical protein [*Mycobacterium* sp. E787] | 99% | 65% | WP_068277017.1 |
| hypothetical protein [*Mycobacterium colombiense*] | 99% | 66% | WP_064950639.1 |
| hypothetical protein [*Mycobacterium* sp. YC-RL4] | 82% | 71% | WP_067990334.1 |
| hypothetical protein [*Mycobacterium rufum*] | 79% | 73% | WP_043414089.1 |
| hypothetical protein [*Mycobacterium* sp. 1165549.7] | 99% | 66% | WP_067171319.1 |
| hypothetical protein [*Mycobacterium* sp. 852002-51057_SCH5723018] | 99% | 65% | WP_067109731.1 |
| hypothetical protein [*Mycobacterium* sp. E342] | 99% | 64% | WP_068061777.1 |
| hypothetical protein [*Mycobacterium* sp. 852013-51886_SCH5428379] | 79% | 72% | WP_066835136.1 |
| hypothetical protein [*Mycobacterium* sp. E3078] | 99% | 66% | WP_067837577.1 |
| hypothetical protein [*Mycobacterium* sp. E3198] | 99% | 65% | WP_068227057.1 |
| hypothetical protein [*Mycobacterium* sp. 1081908.1] | 99% | 65% | WP_067009291.1 |
| hypothetical protein SHTP_3308 [*Mycobacterium ulcerans* subsp. *shinshuense*] | 99% | 65% | BAV42346.1 |
| hypothetical protein [*Mycobacterium* sp. 1245852.3] | 99% | 66% | WP_067344501.1 |
| hypothetical protein [*Mycobacterium* sp. E2699] | 99% | 64% | WP_067871707.1 |
| hypothetical protein [*Mycobacterium triplex*] | 99% | 66% | WP_036466491.1 |
| hypothetical protein [*Mycobacterium aromaticivorans*] | 98% | 61% | WP_036340591.1 |
| hypothetical protein [*Mycobacterium* sp. 1245805.9] | 99% | 65% | WP_067151627.1 |
| conserved secreted protein [*Mycobacterium ulcerans* Agy99] | 99% | 66% | ABL03953.1 |
| hypothetical protein [*Mycobacterium vanbaalenii*] | 87% | 65% | WP_011778329.1 |
| hypothetical protein [*Mycobacterium austroafricanum*] | 87% | 64% | WP_036367359.1 |
| hypothetical protein [*Mycobacterium* sp. 1554424.7] | 99% | 65% | WP_066930932.1 |
| hypothetical protein [*Mycobacterium scrofulaceum*] | 99% | 64% | WP_067282166.1 |
| hypothetical protein [*Mycobacterium genavense*] | 99% | 66% | WP_025737008.1 |
| hypothetical protein [*Mycobacterium* sp. 852002-51971_SCH5477799-a] | 99% | 66% | WP_067122709.1 |

TABLE 5

Results of alignment of ML2531 amino acid sequence with other species

| Name | Cover | Identity | Accession |
|---|---|---|---|
| type VII secretion protein EsxH [*Mycobacterium lepromatosis*] | 100% | 88% | WP_045843896.1 |
| type VII secretion protein EsxH [*Mycobacterium haemophilum*] | 100% | 74% | WP_047315908.1 |

TABLE 5-continued

Results of alignment of ML2531 amino acid sequence with other species

| Name | Cover | Identity | Accession |
|---|---|---|---|
| type VII secretion protein EsxH [*Mycobacterium asiaticum*] | 100% | 74% | WP_036351589.1 |
| ESAT-6-like protein EsxH [*Mycobacterium tuberculosis*] | 100% | 72% | WP_003902934.1 |
| type VII secretion protein EsxH [*Mycobacterium gordonae*] | 100% | 73% | WP_055580201.1 |
| type VII secretion protein EsxH [*Mycobacterium celatum*] | 100% | 72% | WP_062541000.1 |
| MULTISPECIES: type VII secretion protein EsxH [*Mycobacterium*] | 100% | 70% | WP_068070284.1 |
| EsaT-6 like protein EsxH [*Mycobacterium sinense*] | 98% | 76% | AEF34288.1 |
| low molecular weight protein antigen 7 esxH [*Mycobacterium tuberculosis* SUMu010] | 100% | 71% | EFP48790.1 |
| type VII secretion protein EsxH [*Mycobacterium kyorinense*] | 100% | 71% | WP_065012511.1 |
| ESAT-6-like protein EsxH [*Mycobacterium africanum*] | 100% | 70% | WP_003910092.1 |
| type VII secretion protein EsxH [*Mycobacterium heraklionense*] | 98% | 73% | WP_047318399.1 |
| ESAT-6-like protein EsxH [*Mycobacterium canettii*] | 100% | 70% | WP_015288927.1 |
| ESAT-6-like protein EsxH [*Mycobacterium marinum*] | 98% | 72% | WP_011740245.1 |
| type VII secretion protein EsxH [*Mycobacterium sp.* 8WA6] | 98% | 72% | WP_067972689.1 |
| type VII secretion protein EsxH [*Mycobacterium sp. djl-10*] | 98% | 74% | WP_068918824.1 |
| 10 kDa antigen [*Mycobacterium sp.* 012931] | 100% | 69% | EPQ44287.1 |
| type VII secretion protein EsxH [*Mycobacterium sp.* E2327] | 100% | 72% | WP_068102777.1 |
| ESAT-6-like protein EsxH [*Mycobacterium gilvum*] | 98% | 71% | WP_011891324.1 |
| type VII secretion protein EsxH [*Mycobacterium simiae*] | 100% | 71% | WP_061558056.1 |
| type VII secretion protein EsxH [*Mycobacterium sp.* 1274756.6] | 98% | 72% | WP_066851115.1 |
| type VII secretion protein EsxH [*Mycobacterium sp. UM_WGJ*] | 98% | 72% | WP_024443849.1 |
| type VII secretion protein EsxH [*Mycobacterium nebraskense*] | 100% | 70% | WP_046187146.1 |
| EsaT-6 like protein EsxH [*Mycobacterium ulcerans* Agy99] | 100% | 68% | ABL03785.1 |
| type VII secretion protein EsxH [*Mycobacterium sp.* 1081908.1] | 100% | 71% | WP_067013661.1 |
| type VII secretion protein EsxH [*Mycobacterium kansasii*] | 100% | 68% | WP_063467440.1 |
| type VII secretion protein EsxH [*Mycobacterium sp.* 852002-40037_SCH5390672] | 100% | 69% | WP_067104747.1 |
| type VII secretion protein EsxH [*Mycobacterium sp.* E796] | 100% | 70% | WP_068138018.1 |
| type VII secretion protein EsxH [*Mycobacterium sp.* E2733] | 100% | 70% | WP_068040952.1 |
| type VII secretion protein EsxH [*Mycobacterium sp.* 1465703.0] | 100% | 68% | WP_066998456.1 |
| type VII secretion protein EsxH [*Mycobacterium sp.* 852002-51057_SCH5723018] | 100% | 71% | WP_067116855.1 |
| type VII secretion protein EsxH [*Mycobacterium sp.* 1423905.2] | 100% | 68% | WP_067413879.1 |
| type VII secretion protein EsxH [*Mycobacterium iranicum*] | 98% | 68% | WP_064281562.1 |
| low molecular weight protein antigen 7 Cfp7 [*Mycobacterium bohemicum* DSM 44277] | 98% | 72% | CPR13219.1 |
| type VII secretion protein EsxH [*Mycobacterium sp.* 1554424.7] | 100% | 70% | WP_066929865.1 |
| type VII secretion protein EsxH [*Mycobacterium heckeshornense*] | 100% | 71% | WP_048893951.1 |
| low molecular weight protein antigen 7 Cfp7 [*Mycobacterium avium* 104] | 100% | 67% | ABK67570.1 |
| hypothetical protein GuangZ0019_4184 [*Mycobacterium tuberculosis* GuangZ0019] | 100% | 67% | EQM16518.1 |
| type VII secretion protein EsxH [*Mycobacterium sp.* 1245111.1] | 100% | 69% | WP_067330420.1 |

We claim:

1. A fusion polypeptide comprising *Mycobacterium leprae* (*M. leprae*) antigens ML2028, ML2055, and ML2380, or *M. leprae* antigens having at least 90% amino acid sequence identity to ML2028, ML2055, and ML2380.

2. The fusion polypeptide of claim 1, wherein ML2028 comprises the sequence of SEQ ID NO: 2, or a sequence having at least 90% amino acid sequence identity thereto.

3. The fusion polypeptide of claim 1, wherein ML2028 comprises the sequence of SEQ ID NO: 4, or a sequence having at least 90% amino acid sequence identity thereto.

4. The fusion polypeptide of claim 1, wherein ML2055 comprises the sequence of SEQ ID NO: 6, or a sequence having at least 90% amino acid sequence identity thereto.

5. The fusion polypeptide of claim 1, wherein ML2380 comprises the sequence of SEQ ID NO: 8, or a sequence having at least 90% amino acid sequence identity thereto.

6. The fusion polypeptide of claim 1, further comprising *M. leprae* antigen ML2531 or an *M. leprae* antigen having at least 90% amino acid sequence identify to ML2531.

7. The fusion polypeptide of claim 6, wherein the fusion polypeptide comprises the sequence of SEQ ID NO: 12, or a sequence having at least 90% amino acid sequence identity thereto.

8. The fusion polypeptide of claim 6, wherein ML2531 comprises the sequence of SEQ ID NO: 10, or a sequence having at least 90% amino acid sequence identity thereto.

9. A composition comprising the fusion polypeptide of claim 1.

10. The composition of claim 9, further comprising an immunostimulant.

11. The composition of claim 10, wherein the immunostimulant is selected from the group consisting of a CpG-containing oligonucleotide, synthetic lipid A, monophosphoryl lipid A (MPL), saponins, saponin mimetics, amino alkyl glucosaminide 4-phosphates (AGPs), Toll-like receptor agonists, or a combination thereof.

12. The composition of claim 10, wherein the immunostimulant is selected from the group consisting of a TLR4 agonist, a TLR7/8 agonist and a TLR9 agonist.

13. The composition of claim 10, wherein the immunostimulant is selected from the group consisting of glucopyranosyl lipid A (GLA), CpG-containing oligonucleotide, imiquimod, gardiquimod and resiquimod.

14. The composition of claim 13, wherein the immunostimulant is GLA, having the following structure:

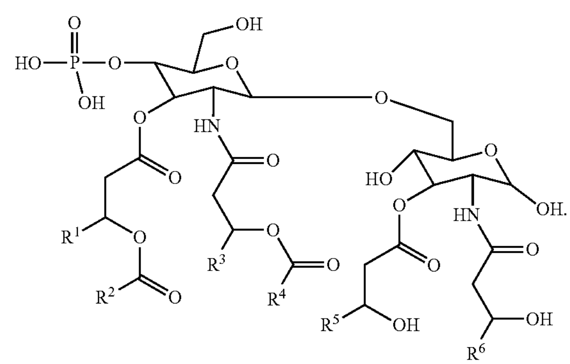

15. The composition of claim 13, wherein the immunostimulant is GLA, having the following structure:

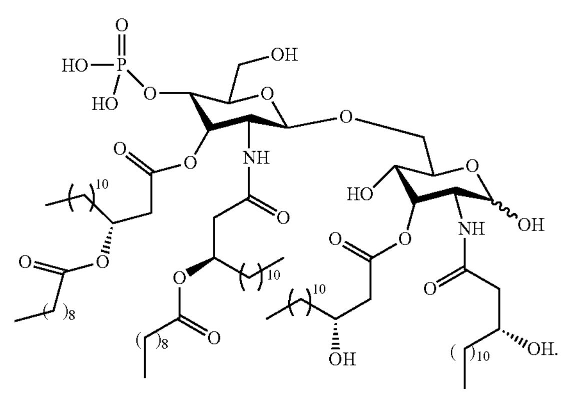

16. The composition of claim 13, wherein the immunostimulant is GLA, having the following structure:

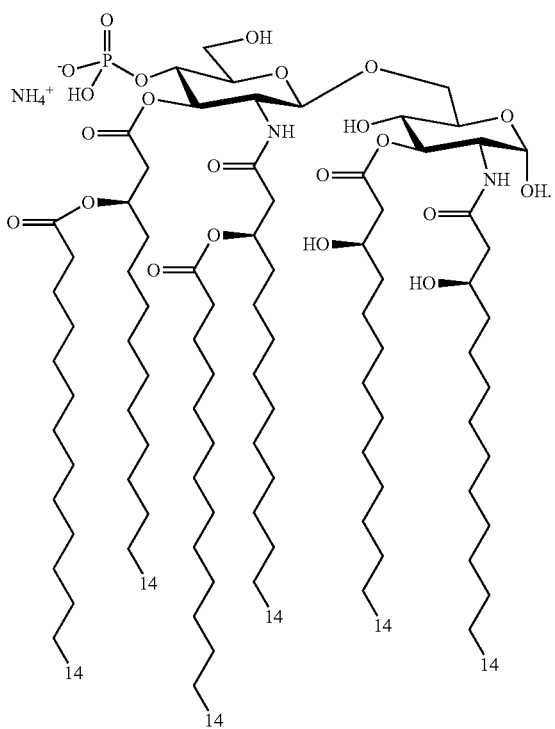

17. The composition of any one of claims 15-16 wherein the GLA is formulated in an oil-in-water emulsion.

18. The fusion polypeptide of claim 1, wherein ML2028 comprises the sequence of SEQ ID NO: 2 or SEQ ID NO: 4, or a sequence having at least 90% amino acid sequence identity thereto, ML2055 comprises the sequence of SEQ ID NO: 6, or a sequence having at least 90% amino acid sequence identity thereto, and ML2380 comprises the sequence of SEQ ID NO: 8, or a sequence having at least 90% amino acid sequence identity thereto.

19. The fusion polypeptide of claim 18, further comprising *M. leprae* antigen ML2531, wherein ML2531 comprises the sequence of SEQ ID NO: 10, or a sequence having at least 90% amino acid sequence identity thereto.

20. A leprosy vaccine comprising a fusion polypeptide comprising *Mycobacterium leprae* (*M. leprae*) antigens ML2028, ML2055, and ML2380.

21. The leprosy vaccine of claim 20, further comprising an immunostimulant.

22. The leprosy vaccine of claim 20, wherein the immunostimulant is selected from the group consisting of a CpG-containing oligonucleotide, synthetic lipid A, monophosphoryl lipid A (MPL), saponins, saponin mimetics, amino alkyl glucosaminide 4-phosphates (AGPs), Toll-like receptor agonists, or a combination thereof.

23. The leprosy vaccine of claim 20, wherein the immunostimulant is selected from the group consisting of a TLR4 agonist, a TLR7/8 agonist and a TLR9 agonist.

24. The leprosy vaccine of claim 20, wherein the immunostimulant is selected from the group consisting of glucopyranosyl lipid A (GLA), CpG-containing oligonucleotide, imiquimod, gardiquimod and resiquimod.

* * * * *